United States Patent
Li et al.

(10) Patent No.: US 10,206,391 B2
(45) Date of Patent: *Feb. 19, 2019

(54) STROBILURIN FORMULATIONS

(75) Inventors: Fugang Li, Richmond Hill (CA); Hung Hoang Pham, Brampton (CA); Rachel Gong, Mississauga (CA); Henry Galas, Toronto (CA)

(73) Assignee: Vive Crop Protection Inc., Toronto, Ontario (CA)

( * ) Notice: Subject to any disclaimer, the term of this patent is extended or adjusted under 35 U.S.C. 154(b) by 0 days.

This patent is subject to a terminal disclaimer.

(21) Appl. No.: 14/367,473

(22) PCT Filed: Aug. 23, 2012

(86) PCT No.: PCT/IB2012/002118
§ 371 (c)(1),
(2), (4) Date: Jun. 20, 2014

(87) PCT Pub. No.: WO2013/093578
PCT Pub. Date: Jun. 27, 2013

(65) Prior Publication Data
US 2014/0364310 A1 Dec. 11, 2014

Related U.S. Application Data

(60) Provisional application No. 61/578,983, filed on Dec. 22, 2011.

(51) Int. Cl.
| | | |
|---|---|---|
| *A01N 43/54* | (2006.01) | |
| *A01N 37/50* | (2006.01) | |
| *A01N 43/40* | (2006.01) | |
| *A01N 43/88* | (2006.01) | |
| *A01N 47/24* | (2006.01) | |
| *A01N 25/04* | (2006.01) | |
| *A01N 25/10* | (2006.01) | |
| *A01N 25/14* | (2006.01) | |
| *C05G 3/02* | (2006.01) | |
| *A01N 37/10* | (2006.01) | |
| *A01N 43/56* | (2006.01) | |
| *A01N 57/20* | (2006.01) | |

(52) U.S. Cl.
CPC ............ *A01N 25/10* (2013.01); *A01N 25/04* (2013.01); *A01N 25/14* (2013.01); *A01N 37/10* (2013.01); *A01N 37/50* (2013.01); *A01N 43/40* (2013.01); *A01N 43/54* (2013.01); *A01N 43/56* (2013.01); *A01N 43/88* (2013.01); *A01N 47/24* (2013.01); *A01N 57/20* (2013.01); *C05G 3/02* (2013.01)

(58) Field of Classification Search
CPC ........ A01N 43/54; A01N 37/50; A01N 43/40; A01N 43/88; A01N 47/24; A01N 25/04; A01N 25/10; A01N 25/14; C05G 3/02
See application file for complete search history.

(56) References Cited

U.S. PATENT DOCUMENTS

| | | | |
|---|---|---|---|
| 5,292,828 A | 3/1994 | Jenkins et al. | |
| 6,383,500 B1 | 5/2002 | Wooley et al. | |
| 6,383,984 B1 | 5/2002 | Aven | |
| 6,436,421 B1 | 8/2002 | Schindler et al. | |
| 6,616,946 B1 | 9/2003 | Meier et al. | |
| 6,683,129 B1 | 1/2004 | Eknoian | |
| 6,897,253 B2 | 5/2005 | Schmucker-Castner et al. | |
| 6,916,481 B1 | 7/2005 | Prud'Homme et al. | |
| 7,070,795 B1 | 7/2006 | Botts et al. | |
| 7,189,279 B2 | 3/2007 | Guillet | |
| 7,939,601 B1 | 5/2011 | Bergeron et al. | |
| 7,994,227 B2 | 8/2011 | Koltzenburg et al. | |
| 8,029,827 B2 | 10/2011 | Martin | |
| 8,309,489 B2 | 11/2012 | Roldan Cuenya et al. | |
| 8,372,418 B2 | 2/2013 | Dujardin et al. | |
| 8,974,806 B2 | 3/2015 | Amrhein et al. | |
| 2007/0122436 A1 | 5/2007 | Koltzenburg et al. | |
| 2007/0212321 A1 | 9/2007 | Braig et al. | |
| 2008/0090886 A1 | 4/2008 | Gottsche et al. | |
| 2008/0138371 A1 | 6/2008 | Amrhein et al. | |
| 2008/0171658 A1 | 7/2008 | Dyllick-Brenzinger et al. | |
| 2008/0213326 A1* | 9/2008 | Amrhein ............... | A01N 25/04 424/405 |
| 2008/0318785 A1 | 12/2008 | Koltzenburg et al. | |
| 2009/0053272 A1 | 2/2009 | Wagenblast | |
| 2010/0015236 A1 | 1/2010 | Magdassi et al. | |
| 2010/0179198 A1 | 7/2010 | Mertoglu et al. | |
| 2010/0210465 A1* | 8/2010 | Li et al. ................... | 504/206 |
| 2010/0227761 A1 | 9/2010 | Bruggemann et al. | |
| 2011/0045975 A1 | 2/2011 | Ehr et al. | |
| 2011/0081555 A1 | 4/2011 | Liu et al. | |
| 2011/0189294 A1 | 8/2011 | Keiper et al. | |
| 2012/0035054 A1 | 2/2012 | Ehr et al. | |
| 2012/0184589 A1 | 7/2012 | Gewehr et al. | |
| 2012/0214857 A1 | 8/2012 | Reinhard et al. | |
| 2012/0264603 A1 | 10/2012 | Soane et al. | |
| 2012/0329648 A1 | 12/2012 | Fowler et al. | |

(Continued)

FOREIGN PATENT DOCUMENTS

| | | |
|---|---|---|
| CA | 2203686 A1 | 11/1997 |
| CN | 1491541 A | 4/2004 |

(Continued)

OTHER PUBLICATIONS

International Search Report for PCT/IB2012/002118, dated Feb. 6, 2013.

(Continued)

*Primary Examiner* — John Pak
*Assistant Examiner* — Nathan W Schlientz
(74) *Attorney, Agent, or Firm* — Charles E. Lyon; Su Kyung Suh; Choate, Hall & Stewart LLP

(57) ABSTRACT

The present disclosure describes a formulation including a nanoparticle including a polymer-associated strobilurin compound with an average diameter of between about 1 nm and about 500 nm; wherein the polymer is a polyelectrolyte, and a dispersant or a wetting agent. The disclosure describes various formulations and formulating agents that can be included in the formulations. Additionally, the disclosures describes application to various plants and fungi as well as advantages of the disclosed formulations.

19 Claims, 1 Drawing Sheet

(56) References Cited

U.S. PATENT DOCUMENTS

| | | |
|---|---|---|
| 2013/0034650 A1 | 2/2013 | Li et al. |
| 2013/0338223 A1 | 12/2013 | Reid et al. |
| 2014/0080702 A1 | 3/2014 | Schnabel et al. |
| 2014/0187424 A1* | 7/2014 | Norton et al. ............... 504/101 |
| 2014/0249031 A1 | 9/2014 | Mulqueen et al. |
| 2014/0294968 A1 | 10/2014 | Hofmann et al. |

FOREIGN PATENT DOCUMENTS

| | | |
|---|---|---|
| CN | 101731223 A | 6/2010 |
| CN | 102223790 A | 10/2011 |
| EP | 0183999 A1 | 6/1986 |
| JP | 2007-509869 A | 4/2007 |
| JP | 2007-534679 A | 11/2007 |
| JP | 2008-508344 A | 3/2008 |
| JP | 2008-532965 A | 8/2008 |
| JP | 2008-536840 A | 9/2008 |
| WO | WO-2005/046328 A1 | 5/2005 |
| WO | WO-2005/102044 A1 | 11/2005 |
| WO | WO-2006/015791 A2 | 2/2006 |
| WO | WO-2006/094792 A1 | 9/2006 |
| WO | WO-2006/111327 A2 | 10/2006 |
| WO | WO 2010/035118 A1 | 4/2010 |
| WO | WO-2010/121323 A1 | 10/2010 |
| WO | WO-2011/042495 A2 | 4/2011 |
| WO | WO 2011/117719 A1 | 9/2011 |

OTHER PUBLICATIONS

Written Opinion Report for PCT/IB2012/002118, dated Feb. 6, 2013.

Extended European Search Report for 12859912.3, 6 pages (dated Aug. 5, 2015).

Ng, W.K., et al., Rheological properties of methacrylic acid/ethyl acrylate co-polymer: comparison between an unmodified and hydrophobically modified system, Polymer, 42:249-259 (2001).

* cited by examiner

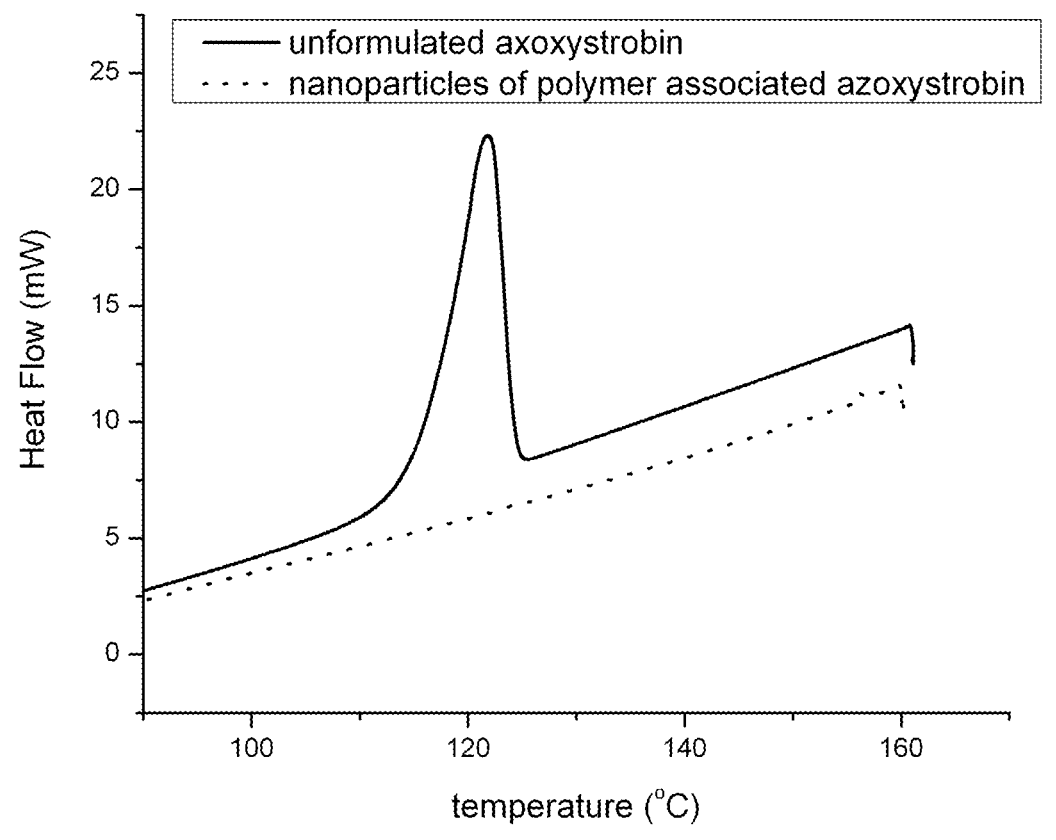

STROBILURIN FORMULATIONS

CROSS REFERENCE TO RELATED APPLICATIONS

This application is a national stage entry of International Application PCT/IB2012/002118 filed Aug. 23, 2012, which claims priority to U.S. Provisional Patent Application Ser. No. 61/578,983, filed on Dec. 22, 2011, the entire contents of each of which are hereby incorporated by reference.

BACKGROUND

Strobilurins are widely used in agriculture as fungicides. They belong to the $Q_oI_{family}$ of fungicides and are used to control a wide array of fungal diseases caused by water moulds, downy mildews, powdery mildews, leaf spotting and blighting fungi, fruit rotters, and rusts. $Q_oI$ fungicides are chemical compounds that act at the Quinol outer binding site of the cytochrome bc1 complex, inhibiting fungal mitochondrial respiration that stops energy production in the fungus and results in its death. The strobilurins are used on a wide variety of crops including cereals, field crops, fruits, tree nuts, vegetables, turfgrass and ornamentals. Most strobilurins show weak systemic activity, and are useful—to varying degrees—as protectant, curative and translaminar fungicides (ref: Balba, H. J. Envi. Sci. Heath. Part B. 2007, 42, 441. As an example, azoxystrobin shows good protective yet mild curative properties due to its weak systemic properties. A useful formulation would mitigate these drawbacks of the fungicide and ideally provide excellent protectant and curative properties, so that it can both protect a crop from fungal infection and eradicate the infection after it is established. Because strobilurins target only a single metabolic pathway in the fungus, there are instances where mutations can occur in certain species that can make them resistant to strobilurins. It is therefore also useful to create strobilurin formulations that can easily be mixed with fungicides that have other modes of action to minimize the spread of strobilurin resistant strains.

Strobilurins are nonpolar compounds, have relatively low water solubility (on the scale of ug/Lg/L), low volatility, and have moderate to low soil mobility. Strobilurins can vary in their stability towards hydrolysis and photolysis under natural environmental conditions where pH and temperature contribute to their chemical degradation. There is further a need to create formulations that can extend the effective lifetime of strobilurins and related compounds by reducing their susceptibly towards chemical degradation both before and after the formulation has been applied in the field.

Strobilurins are currently formulated into various usable forms such as emulsifiable concentrates (ECs), liquid concentrate (SL), and suspension concentrates (SC) that use petroleum or non-petroleum based solvents along with anionic and non-ionic emulsifiers and stabilizers. Strobilurins have also been formulated as water dispersible powders or granules (WPs or WGs) and soluble powders (SP) that use organic or inorganic carriers. These formulations are available as solid or liquid formulations with varying contents of active ingredient (low or high) that can be used as is or after dilution with water. As described below, while these formulations address some of the inherent challenges that are associated with strobilurins there remains a need in the art for improved strobilurin formulations.

SUMMARY OF THE INVENTION

The present disclosure provides formulations of strobilurin compounds including nanoparticles of polymer-associated strobilurin compounds along with various formulating agents. The present disclosure also provides methods for producing and using these formulations.

In various embodiments of the present disclosure presents formulations including a nanoparticle including a polymer-associated strobilurin compound with an average diameter of between about 1 nm and about 500 nm; and the polymer is a polyelectrolyte, and a dispersant or a wetting agent.

In some embodiments, the nanoparticle has a diameter of between about 1 nm and about 100 nm. In some embodiments, the nanoparticle has a diameter of between about 1 nm and about 20 nm.

In some embodiments, the formulation includes a plurality of nanoparticles, wherein the nanoparticles are in an aggregate and the aggregate has a diameter of between about 10 nm and about 5000 nm. In some embodiments, the formulation includes a plurality of nanoparticles, wherein the nanoparticles are in an aggregate and the aggregate has a diameter of between about 100 nm and about 2500 nm. In some embodiments, the formulation includes a plurality of nanoparticles, wherein the nanoparticles are in an aggregate and the aggregate has a diameter of between about 100 nm and about 1000 nm. In some embodiments, the formulation includes a plurality of nanoparticles, wherein the nanoparticles are in an aggregate and the aggregate has a diameter of between about 100 nm and about 300 nm.

In some embodiments the ratio of strobilurin compound to polymer within the nanoparticles is between about 10:1 and about 1:10 on a w/w basis. In some embodiments, the ratio of strobilurin compound to polymer within the nanoparticles is between about 5:1 and about 1:5. In some embodiments, the ratio of strobilurin compound to polymer within the nanoparticles is between about 2:1 and about 1:2. In some embodiments, the ratio of strobilurin compound to polymer within the nanoparticles is about 1:3. In some embodiments, the ratio of strobilurin compound to polymer within the nanoparticles is about 3:2. In some embodiments, the ratio of strobilurin compound to polymer within the nanoparticles is about 1:1. In some embodiments, the ratio of strobilurin compound to polymer within the nanoparticles is about 4:1. In some embodiments, the ratio of strobilurin compound to polymer within the nanoparticles is about 2:1.

In some embodiments, the strobilurin compound is azoxystrobin. In some embodiments, the strobilurin compound is pyraclostrobin. In some embodiments, the strobilurin compound is trifloxystrobin.

In some embodiments, the polymer is selected from the group consisting of poly(methacrylic acid-co-ethyl acrylate); poly(methacrylic acid-co-styrene); poly(methacrylic acid-co-butylmethacrylate); poly[acrylic acid-co-poly(ethylene glycol) methyl ether methacrylate]; poly(n-butylmethacrylcate-co-methacrylic acid). In some embodiments, the polymer is a homopolymer. In some embodiments, the polymer is a copolymer. In some embodiments, the polymer is a random copolymer.

In some embodiments, the dispersant and/or wetting agent is selected from the group consisting of lignosulfonates, organosilicones, methylated or ethylated seed oils, ethoxylates, sulfonates, sulfates and combinations thereof. In some embodiments, the dispersant and/or wetting agent is sodium lignosulfonate. In some embodiments, the dispersant and/or wetting agent is a tristyrylphenol ethoxylate. In some embodiments, the wetting agent and the dispersant are the same compound. In some embodiments, the wetting agent and the dispersant are different compounds.

In some embodiments, the formulation excludes any wetting agent. In some embodiments, the formulation excludes any dispersant. In some embodiments, the wetting agent is less than about 30 weight % of the formulation. In some embodiments, the wetting agent is less than about 5 weight % of the formulation. In some embodiments, the dispersant is less than about 30 weight % of the formulation. In some embodiments, the dispersant is less than about 5 weight % of the formulation.

In some embodiments, the formulation is in the form of a high solids liquid suspension.

In some embodiments, the formulation includes between about 0.05 weight % and about 5 weight % of a thickener. In some embodiments, the thickener is less than about 1 weight % of the formulation. In some embodiments, the thickener is less than about 0.5 weight % of the formulation. In some embodiments, the thickener is less than about 0.1 weight % of the formulation. In some embodiments, the thickener is selected from the group consisting of guar gum; locust bean gum; xanthan gum; carrageenan; alginates; methyl cellulose; sodium carboxymethyl cellulose; hydroxyethyl cellulose; modified starches; polysaccharides and other modified polysaccharides; polyvinyl alcohol; glycerol alkyd, fumed silica and combinations thereof.

In some embodiments, the formulation includes between about 0.01 weight % and about 0.2 weight % of a preservative. In some embodiments, the preservative is less than about 0.1 weight % of the formulation. In some embodiments, the preservative is less than about 0.05 weight % of the formulation. In some embodiments, the preservative is selected from the group consisting of tocopherol, ascorbyl palmitate, propyl gallate, butylated hydroxyanisole (BHA), butylated hydroxytoluene (BHT), propionic acid and its sodium salt; sorbic acid and its sodium or potassium salts; benzoic acid and its sodium salt; p-hydroxy benzoic acid sodium salt; methyl p-hydroxy benzoate; 1,2-benzisothiazalin-3-one, and combinations thereof.

In some embodiments, the formulation includes between about 0.05 weight % and about 10 weight % of an anti-freezing agent. In some embodiments, the anti-freezing agent is less than about 5 weight % of the formulation. In some embodiments, the anti-freezing agent is less than about 1 weight % of the formulation. In some embodiments, the anti-freezing agent is selected from the group consisting of ethylene glycol; propylene glycol; urea and combinations thereof.

In some embodiments, the formulation includes water or PBS buffer. In some embodiments, the water or PBS buffer is less than about 50 weight % of the formulation. In some embodiments, the water or PBS buffer is less than about 25 weight % of the formulation. In some embodiments, the water or PBS buffer is less than about 10 weight % of the formulation.

In some embodiments, the polymer-encapsulated strobilurin compound is less than about 80 weight % of the formulation. In some embodiments, the nanoparticles of polymer-associated strobilurin comprise between about 20 weight % and about 80 weight % of the formulation. In some embodiments, the nanoparticles of polymer-associated strobilurin comprise between about 20 weight % and about 60 weight % of the formulation. In some embodiments, the nanoparticles of polymer-associated strobilurin comprise about 20 weight % and about 50 weight % of the formulation. In some embodiments, the nanoparticles of polymer-associated strobilurin comprise between about 25 weight % and about 50 weight % of the formulation. In some embodiments, the nanoparticles of polymer-associated strobilurin comprise about 30 weight % and about 40 weight % of the formulation.

In some embodiments, the polymer-associated strobilurin compound is between about 5 weight % and about 40 weight % of the formulation. In some embodiments, wherein the polymer-associated strobilurin compound is between about 5 weight % and about 25 weight % of the formulation. In some embodiments, the polymer-associated strobilurin compound is between about 10 weight % and about 25 weight % of the formulation. In some embodiments, the polymer-associated strobilurin compound is between about 15 weight % and about 25 weight % of the formulation.

In various embodiments of the present disclosure presents formulations including a nanoparticle including a polymer-associated strobilurin compound with an average diameter of between about 1 nm and about 500 nm; and the polymer is a polyelectrolyte, a dispersant or a wetting agent, a thickener, a preservative, an anti-freezing agent; and water or PBS buffer.

In various embodiments of the present disclosure presents formulations including a nanoparticle including a polymer-associated strobilurin compound with an average diameter of between about 1 nm and about 500 nm; and the polymer is a polyelectrolyte, between about 1 weight % and about 30 weight % of a dispersant or a wetting agent, between about 0.05 weight % and about 5 weight % of a thickener, between about 0.01 weight % and about 0.2 weight % of a preservative, between about 0.05 weight % and about 10 weight % of an anti-freezing agent; and water or PBS buffer.

In some embodiments, the nanoparticles of polymer-associated strobilurin comprise between about 20 weight % and about 80 weight % of the specific formulation described above. In some embodiments, the polymer-associated strobilurin compound is between about 5 weight % and about 25 weight % of the specific formulation described above.

In some embodiments, the formulation is in the form of a wettable granule.

In some embodiments, the formulation includes an inert filler. In some embodiments, the inert filler makes up less than about 90 weight % of the formulation. In some embodiments, the inert filler makes up less than about 40 weight % of the formulation. In some embodiments, the inert filler makes up less than about 5 weight % of the formulation. In some embodiments, the inert filler is selected from the group consisting of saccharides, celluloses, starches, carbohydrates, vegetable oils, protein inert fillers, polymers and combinations thereof.

In some embodiments, the formulation includes water. In some embodiments, the water is less than about 50 weight % of the formulation. In some embodiments, the water is less than about 25 weight % of the formulation. In some embodiments, the water is less than about 10 weight % of the formulation.

In some embodiments, the formulation includes between about 1 weight % and about 20 weight % of a disintegrant. In some embodiments, the disintegrant is selected from the group consisting of polyvinyl pyrrolidone, modified cellulose gum, pregelatinized starch, cornstarch, modified corn starch, sodium carboxymethyl starch, microcrystalline cellulose, sodium starch glycolate, sodium carboxymethyl cellulose, carmellose, carmellose calcium, carmellose sodium, croscarmellose sodium, carmellose calcium, carboxymethylstarch sodium, low-substituted hydroxypropyl cellulose, hydroxypropyl methylcellulose, hydroxypropyl cellulose, soy polysaccharides, alkylcelullose, hydroxyalkylcellulose, alginates, dextrans and poly(alkylene oxide), a combination of citric acid or bicarbonate, a combination of ascorbic acid and bicarbonate, lactose, anhydrous dibasic calcium phosphate, dibasic calcium phosphate, magnesium aluminometasilicate, synthesized hydrotalcite, silicic anhydride synthesized aluminum silicate and combinations thereof.

In some embodiments, the polymer-associated strobilurin compound has a melting point of less than 100° C. In some embodiments, the polymer-associated strobilurin compound has a melting point of less than 80° C. In some embodiments, polymer-associated strobilurin compound is selected from the group consisting of the following picoxystrobin, pyraclostrobin, orysastrobin, metominostrobin and trifloxystrobin.

In some embodiments, the formulation excludes a UV-blocker. In some embodiments, the formulation excludes a thickener.

In some embodiments, the formulation includes between about 1 weight % and about 20 weight % of a non-ionic surfactant. In some embodiments, the non-ionic surfactant is less than about 1 weight % of the formulation. In some embodiments, the non-ionic surfactant is less than about 0.5 weight % of the formulation. In some embodiments, the non-ionic surfactant is selected from the group consisting of alkylphenol ethoxylates, tristyrylphenol ethoxylates, aliphatic alcohol ethoxylates, aliphatic alkylamine ethoxylates, sorbitan esters and their ethoxylates, castor oil ethoxylates, ethylene oxide/propylene oxide copolymers, polymeric surfactants and combinations thereof.

In some embodiments, the formulation includes between about 0.1 weight % and about 90 weight % of a solvent. In some embodiments, the solvent is less than about 20 weight % of the formulation. In some embodiments, the solvent is less than about 10 weight % of the formulation. In some embodiments, the solvent is selected from the group consisting of alcohols, alkenes, alkanes, alkynes, phenols, hydrocarbons, chlorinated hydrocarbons, ketones, water, ethers and combinations thereof.

In some embodiments, the formulation includes between about 0.05 weight % and about 5 weight % of an anti-foaming agent. In some embodiments, the anti-foaming agent is less than about 1 weight % of the formulation. In some embodiments, the anti-foaming agent is selected from the group consisting of sodium or ammonium phosphates, sodium carbonate or bicarbonate, sodium acetate, sodium metasilicate, magnesium or zinc sulfates, magnesium hydroxide hydrates of any of the forgoing, sodium alkylsulfosuccinates, silicious compounds, magnesium compounds, C10-C22 fatty acids, polyvalent metal salt compounds and combinations thereof.

In some embodiments, the formulation includes between about 0.05 weight % and about 3 weight % of an anti-caking agent. In some embodiments, the anti-caking agent is less than about 1 weight % of the formulation. In some embodiments, the anti-caking agent is selected from the group consisting of attapulgite clay, kieselguhr, silica aerogel, silica xerogel, perlite, talc, vermiculite, sodium aluminosilicate, zirconium oxychloride, starch, sodium or potassium phthalate, calcium silicate, calcium phosphate, calcium nitride, aluminum nitride, copper oxide, magnesium carbonate, magnesium silicate, magnesium nitride, magnesium phosphate, magnesium oxide, magnesium nitrate, magnesium sulfate, magnesium chloride, and the magnesium and aluminum salts of C10-C22 fatty acids, refined kaolin clay, amorphous precipitated silica dioxide, refined clay, fumed silica, and combinations thereof.

In some embodiments, the formulation is diluted so that the concentration of the polymer-associated strobilurin compound is between about 0.1 to about 1000 ppm. In some embodiments, the formulation is diluted so that the concentration of the polymer-associated strobilurin compound is between about 10 to about 1000 ppm. In some embodiments, the formulation is diluted so that the concentration of the polymer-associated strobilurin compound is between about 10 to about 500 ppm. In some embodiments, the formulation is diluted so that the concentration of the polymer-associated strobilurin compound is between about 10 to about 100 ppm.

In some embodiments, the formulation is in an aqueous dispersion. In some embodiments, the formulation is the concentration of the strobilurin in the dispersion is less than solubility limit of the strobilurin in water. In some embodiments, the strobilurin is associated with the polymer in the dispersion.

In some embodiments, the water used to form the dispersion has an ionic strength of between about 0 to about 8000 ppm calcium +2 equivalent. In some embodiments, the water used to form the dispersion has an ionic strength of between about 100 to about 2000 ppm calcium +2 equivalent. In some embodiments, the water used to form the dispersion has an ionic strength of between about 100 to about 400 ppm calcium +2 equivalent. In some embodiments, the water used to form the dispersion has an ionic strength of between about 50 to about 400 ppm calcium +2 equivalent. In some embodiments, the water used to form the dispersion has an ionic strength of between about 1000 to about 4000 ppm calcium +2 equivalent.

In some embodiments, the aqueous dispersion further contains an herbicide. In some embodiments, the herbicide is glyphosate.

In some embodiments, the formulation further includes a fertilizer. In some embodiments, the fertilizer is a liquid fertilizer. In some embodiments, the fertilizer comprises at least one of the elements selected from the group consisting of the following: boron, copper, manganese, iron, chorine, molybdenum, zinc sulfur, nitrogen, phosphorus and potassium.

In some embodiments, the dispersion further includes between about 0.1 weight % and about 20 weight % of a non-ionic surfactant. In some embodiments, the non-ionic surfactant is less than about 1 weight % of the formulation. In some embodiments, the non-ionic surfactant is less than about 0.5 weight % of the formulation. In some embodiments, the non-ionic surfactant is selected from the group consisting of alkylphenol ethoxylates, tristyrylphenol ethoxylates, aliphatic alcohol ethoxylates, aliphatic alkylamine ethoxylates, sorbitan esters and their ethoxylates, castor oil ethoxylates, ethylene oxide/propylene oxide copolymers, polymeric surfactants and combinations thereof.

In various aspect the present disclosure provides a method of using any of the formulations described herein by applying the formulation to a plant.

In various embodiments of the present disclosure presents a method of using any of the formulations described above by applying the formulation to the root zone of a plant.

In various embodiments of the present disclosure presents a method of using any of the formulations described above by applying the formulation to one part of a plant and the strobilurin translocates to an unapplied part of the plant.

In some embodiments, the unapplied part of the plant includes new plant growth since the application.

In various embodiments of the present disclosure presents a method of inoculating a plant with a strobilurin against fungi by applying any of the formulations described above to the plant's roots.

In some embodiments, the present disclosure provides a method of treating a fungal infection of a plant with a strobilurin by applying any formulation described herein to the plant.

In various embodiments of the present disclosure presents a method of increasing a plant's fungus resistance by applying any of the formulations described above to the plant's roots.

In some embodiments, the plant is selected from the classes fabaceaae, brassicaceae, rosaceae, solanaceae, convolvulaceae, poaceae, amaranthaceae, laminaceae and apiaceae.

In some embodiments, the plant is selected from oil crops, cereals, pasture, turf, ornamentals, fruit, legume vegetables, bulb vegetables, cole crops, tobacco, soybeans, cotton, sweet corn, field corn, potatoes and greenhouse crops.

In some embodiments, the fungi are selected from the classes ascomycota, basidiomycota, deuteromycota, blastocladiomycota, chytridiomycota, glomeromycota and combinations thereof.

In various embodiments of the present disclosure presents a method of using any of the formulations described above including the steps of applying any of the formulations described above to a crop field so that the concentration of the strobilurin is about at 0.35 grams per hectare.

In various embodiments of the present disclosure presents a method of any of the formulations described above including the steps of applying any of the formulations described above to trees, bushes or shrubs.

In some embodiments, the present disclosure provides a method of using any of the formulations described herein by applying the formulation to trees, bushes or shrubs.

In various aspects the present disclosure provides a method of using any formulation as described above to cure or prevent a fungal infection, and the formulation is applied to a soybean plant at a concentration of between about 11 and about 109 grams of strobilurin compound per hectare and the fungus is selected from the group consisting of Aerial blight (*Rhizoctonia solani*), Anthracnose (*Colletotrichum truncatum*), *Alternaria* leaf spot (*Alternaria* spp.), Brown spot (*Septoria glycines*) *Cercospora* blight and leaf spot (*Cercospora kikuchii*), Frogeye leaf spot (*Cercospora sojina*), Pod and stem blight (*Diaporthe phaseolorum*). In some embodiments, the strobilurin compound is azoxystrobin or pyraclostrobin.

In various aspects the present disclosure provides a method of using any formulation as described above to cure or prevent a fungal infection, and the formulation is applied to a corn plant at a concentration of between about 11 and about 109 grams of strobilurin compound per hectare and the fungus is selected from the group consisting of Rust (*Puccinia sorghi*), anthracnose leaf blight (*Colletotrichum graminicola*), Gray leaf spot (*Cercospora sorghi*), Northern corn leaf blight (*Setosphaeria turcica*), Northern corn leaf spot (*Cochliobolus carbonum*), Southern corn leaf blight (*Cochliobolus heterostrophus*) and Eye spot (*Aureobasidium zeae*). In some embodiments, the strobilurin compound is azoxystrobin or pyraclostrobin.

In various aspects the present disclosure provides a method of using any formulation as described above to cure or prevent a fungal infection, and the formulation is applied to a rice plant at a concentration of between about 22 and about 228 grams of azoxystrobin per hectare and the fungus is selected from the group consisting of Aggregate sheath spot (*Ceratobasidium oryzae-sativae, Rhizoctonia oryzae-sativae*), Black sheath rot (*Gaeumannomyces graminis* var. *graminis*), Sheath spot (*Rhizoctonia oryzae*), Stem rot (*Magnaporthe salvinii*=*Sclerotium oryzae*=*Nakateae sigmoidea*), Brown leaf spot (*Cochliobolus miyabeanus*), Leaf smut (*Entyloma oryzae*), Narrow brown leaf spot (*Cercospora janseana*=*Cercospora oryzae*), Kernel smut (*Tilletia barclayana, Neovossia barclayana*) and Panicle blast (*Pyricularia grisea*).

In various aspects the present disclosure provides a method of using any formulation as described above to cure or prevent a fungal infection, and the formulation is applied to a wheat plant at a concentration of between about 5 and about 50 grams of azoxystrobin per hectare and the fungus is selected from the group consisting of *Bipolaris sorokiniana, Drechslera tritici-repentis*, and *Puccinia triticina*.

In various aspects the present disclosure provides a method of using any formulation as described above to cure or prevent a fungal infection, and the formulation is applied to a wheat plant at a concentration of between about 11 and about 110 grams of pyraclostrobin per hectare and the fungus is selected from the group consisting of Black Spot, Leaf Rust, Powdery Mildew, *Septoria* Leaf And Glume Blotch, Spot Blotch, Stem Rust, Stripe Rust, and Tan Spot (Yellow Leaf Spot).

In various aspects the present disclosure provides a method of using any formulation as described above to cure or prevent a fungal infection, and the formulation is applied to a wheat plant at a concentration of between about 15 and about 150 grams of pyraclostrobin per hectare and the fungus is selected from the group consisting of *Drecheslera tritici-repentis, Pucciniatriticina, Bipolaris sorokiniana, Leptosphaeria nodorum*, and *Septoria tritici*.

In various aspects the present disclosure provides a method of using any formulation as described above to cure or prevent a fungal infection, and the formulation is applied to a rice plant at a concentration of between about 11 and about 139 grams of trifloxystrobilurin per hectare and the fungus is sheath blight (*rhizoctonia solani*).

In various aspects the present disclosure provides a method of making a high solids liquid suspension formulation including the steps of milling nanoparticles of a polymer-associated strobilurin compound with, a dispersant and/or wetting agent; and water.

In various aspects the present disclosure provides a method of making a high solids liquid suspension formulation including the steps of milling polyelectrolyte nanoparticles with, a strobilurin compound, a dispersant and/or wetting agent; and water.

In various aspects the present disclosure provides a method of making a wettable granule formulation including the steps of mixing dried nanoparticles of a polymer-associated strobilurin compound with water, extruding the mixture through an orifice; and dividing the extruded material into granules.

In some embodiments, the strobilurin compound used in the method of making described above has a melting point below 100° C. In some embodiments, the strobilurin compound used in the method of making described above has a melting point below 80° C.

In some embodiments, the strobilurin compound used in the method of making described above is selected from the group consisting of the following picoxystrobin, pyraclostrobin, orysastrobin, metominostrobin and trifloxystrobin.

In some embodiments, the strobilurin compound used in the method of making described above is between about 5 weight % and about 25 weight % of the formulation.

In some embodiments, the strobilurin compound used in the method of making described above is between about 10 weight % and about 25 weight % of the formulation.

In some embodiments, the strobilurin compound used in the method of making described above is between about 15 weight % and about 25 weight % of the formulation.

In some embodiments, the polymer nanoparticles and the strobilurin compound used in the method of making described above is between about 20 weight % and about 80 weight % of the formulation. In some embodiments, the polymer nanoparticles and the strobilurin compound used in the method of making described above is between about 20 weight % and about 60 weight % of the formulation. In some embodiments, the polymer nanoparticles and the strobilurin compound used in the method of making described above is between about 20 weight % and about 50 weight % of the formulation. In some embodiments, the polymer nanoparticles and the strobilurin compound used in the method of making described above is between about 30 weight % and about 50 weight % of the formulation.

In some embodiments, the ratio of strobilurin compound to polymer within the nanoparticles used in the methods of making described above is between about 5:1 and about 1:5.

In some embodiments, the method of making described above includes one or more of the following formulating agents: an anti-freeze, a anti-foaming agent, a thickener, a preservative.

BRIEF DESCRIPTION OF THE DRAWING

FIG. 1 shows the results of Differential Scanning calorimetry (DSC) analysis of unformulated azoxystrobin and nanoparticles of polymer associated azoxystrobin.

DEFINITIONS

As used herein, the term "inoculation" refers to a method used to administer or apply a formulation of the present disclosure to a target area of a plant or fungus. The inoculation method can be, but is not limited to, aerosol spray, pressure spray, direct watering, and dipping. Target areas of a plant could include, but are not limited to, the leaves, roots, stems, buds, flowers, fruit, and seed. Target areas of the fungus could include, but are not limited to, the hyphae and mycelium, inoculating reproductive spores (conidia or ascospores) and the haustoria. Inoculation can include a method wherein a plant is treated in one area (e.g., the root zone or foliage) and another area of the plant becomes protected (e.g., foliage when applied in the root zone or new growth when applied to foliage). Inoculation can also include a method wherein a plant is treated in one area (e.g., the foliar surface) and fungal infection in the interior of the plant is cured.

As used herein, the term "wettable granule" also referred to herein as "WG", "wettable granule", and "soluble granule" refers to a solid granular formulation that is prepared by a granulation process and that contains nanoparticles of polymer-associated active ingredient, (includes potentially aggregates of the same), a wetting agent and/or a dispersant, and optionally an inert filler. Wettable granules can be stored as a formulation, and can be provided to the market and/or end user without further processing. In some embodiments, they can be placed in a water-soluble bag for ease of use by the end user. In most practical applications, wettable granules are prepared for application by the end user. The wettable granules are mixed with water in the end user's spray tank to the proper dilution for the particular application. Dilution can vary by crop, fungus, time of year, geography, local regulations, and intensity of infestation among other factors. Once properly diluted, the solution can be applied by e.g., spraying.

As used herein, the term "wettable powder" also referred to herein as "WP", "water dispersible powder" and "soluble powder", refers to a solid powdered formulation that contains nanoparticles of polymer-associated active ingredient (includes potentially aggregates of the same), and optionally one or more of a dispersant, a wetting agent, and an inert filler. Wettable powders can be stored as a formulation, and can be provided to the market and/or end user without further processing. In some embodiments, they can be placed in a water-soluble bag for ease of use by the end user. In practical applications, a wettable powder is prepared for application by the end user. The wettable powder is mixed with water in the end user's spray tank to the proper dilution for the particular application. Dilution can vary by crop, fungus, time of year, geography, local regulations, and intensity of infestation among other factors. Once properly diluted, the solution can be applied by e.g., spraying.

As used herein, the term "high solids liquid suspension" also referred to herein as "HSLS" refers to a liquid formulation that contains nanoparticles of polymer nanoparticles associated with active ingredient (includes potentially aggregates of the same), a wetting agent and/or a dispersant, an anti-freezing agent, optionally an anti-settling agent or thickener, optionally a preservative, and water. High solids liquid suspensions can be stored as a formulation, and can be provided to the market and/or end user without further processing. In most practical applications, high solids liquid suspensions are prepared for application by the end user. The high solids liquid suspensions are mixed with water in the end user's spray tank to the proper dilution for the particular application. Dilution can vary by crop, fungus, time of year, geography, local regulations, and intensity of infestation among other factors. Once properly diluted, the solution can be applied by e.g., spraying.

DESCRIPTION OF VARIOUS EMBODIMENTS OF THE INVENTION

Strobilurins represent a very important class of fungicide globally. Strobilurins are primarily used in agriculture to protect crops such as cereals, field crops, fruits, tree nuts, vegetables, turfgrass and ornamentals because of their broad spectrum activity as well as (to varying degrees) their activity against all three major groups of plant pathogenic fungi: Ascomycetes, Basidiomycetes, and Deuteromycetes. Strobilurins have found limited use outside agricultural applications (such as human and veterinary antifungal formulations).

Strobilurins as a chemical class are based on natural substances isolated from wood-rotting mushroom fungi from the genera *Strobilurus*. Natural strobilurins break down rapidly in light and upon exposure to $H_2O$ and are thus not reliable for disease control. They can also break down rapidly in the soil due to bacterial degradation (*Biocatalysis and Biotransformation*, V29 (4), 119-129). While synthetic analogs of natural strobilurins have been developed and have resulted in compounds that are less subject to breakdown, most of the synthetic strobilurins still undergo photolysis and degradation upon direct exposure to sunlight and/or soil. Strobilurins, whether naturally occurring or synthesized, suffer from several major problems that make them challenging to use as fungicides. In particular, in addition to being potentially degraded under aqueous conditions, strobilurins also have limited water solubility, exhibit low soil mobility and show weak to moderate systemic and curative activity in plants without the addition of adjuvants. In this context, curative activity refers to the ability for the strobilurin to treat fungal infection that has already been established in the plant. This typically requires the strobilurin to be at least moderately systemic, as it needs to penetrate through the plant cuticle and into the plant to the infected tissue. Furthermore, because of strobilurins have a very specific mode of action, targeted fungi can become resistant. Different formulation techniques have therefore been developed in an attempt to address these deficiencies. An ideal formulation would have adequate loading of the active ingredient, be non-odorous, non-caking, non-foaming, stable under extreme conditions for extended periods of time, disperse rapidly upon addition to a spray tank, be compatible with a range of secondary additives and other agricultural products (fertilizer, pesticide, herbicide and other formulations) added to a spray tank, pourable or flowable, and, for solid formulations, be non-dusty (for solid formulations), and have sufficient/superior rainfast properties after application.

UV Stability

Current strobilurins vary in their susceptibility to sunlight and exhibit a wide range of half lives as shown in Table 1.

TABLE 1

Photolytic stability of some Strobilurins

| Strobilurin | Photolytic stability |
|---|---|
| Fluxastrobin | $DT_{50}$ 3.8-4.1 days in sterile aqueous phosphate buffer, pH 7; 19- 22 days under solar summer conditions, Phoenix AZ, USA in June.[+] |
| Fenamidone | Readily photodegraded under aqueous conditions. $DT_{50}$ 5.9 days (lab., aerobic)[+] |
| Azoxystrobin | $DT_{50}$ for aqueous photolysis 8.7 days, pH7 |
| Picoxystrobin | $DT_{50}$ for aqueous photolysis 21 days, pH7 |
| Enestroburin | — |
| Pyraclostrobin | Photolysis $DT_{50}$ in water 1.7 days, pH7 |
| Famoxadone | $DT_{50}$ 4.6 days (pH5), 1.9 days in water (pH7) |
| Dimoxystrobin | $DT_{50}$ for aqueous photolysis 30 days, pH7 |
| Metominostrobin | Slightly unstable to light |
| Orysastrobin | Photolysis $DT_{50}$ 0.8 days, pH7 |
| Kresoxim-methyl | Photolysis $DT_{50}$ 18.2 days, pH7 |
| Trifloxystrobin | Aqueous photolysis $DT_{50}$ 2.7 days (pH 7), 1.1 days (pH 5) |
| — | — |

[+]The e-pesticide manual, Ver. 5. British Crop Protection Council

Due to the tendency of some strobilurins to degrade in sunlight, most strobilurin formulations can include inorganic UV-blockers like zinc, tin or iron oxides or an organic UV blocker such as 1,2-dihydroxybenzophenone (European Patent EP1755841, WIPO Patent Application WO/2010/115720, European Patent EP1697578). The addition of UV-blockers into a formulation can complicate formulations, as UV-blockers need to be soluble or dispersible in the matrix in which the product is formulated. It would therefore be desirable to provide formulations that do not require UV-blockers and can prevent formulated actives to a certain degree from being degraded by UV irradiation.

Hydrolysis/Stability

Strobilurins vary widely in their stability in different media. Most are quite stable in neutral to slightly basic/acidic conditions but become increasingly susceptible to hydrolysis/degradation under alkaline conditions. Stability data for some strobilurins are provided in Table 2 (taken from the e-pesticide manual, Ver. 5. British Crop Protection Council). Most strobilurins are degraded in the plant tissues, and only four strobilurins (azoxystrobin, fluxastrobin, picoxystrobin, dimoxystrobin) are metabolically sufficiently stable in plants and show a pronounced xylem systemicity (Zelená V., Veverka K., 2007, Plant Protect. Sci. V 43, 151-156). Therefore it would be desirable to have formulations that provide protection to the formulated actives from being degraded or hydrolyzed in aqueous conditions.

TABLE 2

Stability data of some strobilurins in different media

| Strobilurin | Stability data |
|---|---|
| Fluxastrobin | Hydrolysis $DT_{50}$ >1 y (pH 4, 7 and 9, 50° C.); |
| Fenamidone | Hydrolysis $DT_{50}$ (25° C., sterile conditions) 41.7 d (pH 4), 411 d (pH 7), 27.6 d (pH 9). |
| Azoxystrobin | Stable to hydrolysis at pH 5-7 and room temperature. |
| Picoxystrobin | Stable at pH 5 and pH 7; $DT_{50}$ c. 15 d (pH 9, 50° C.) |
| Enestroburin | — |
| Pyraclostrobin | Stable >30 d (pH 5-7, 25° C.). |
| Famoxadone | In water with no light, $DT_{50}$ 41 d (pH 5), 2 d (pH 7), 0.0646 d (pH 9) (25° C.); in water with light, $DT_{50}$ 4.6 d (pH 5, 25° C.). |
| Dimoxystrobin | Stable >30 d in aqueous solution at pH 4-9, 50° C. |
| Metominostrobin | Stable to heat, and to acidic and alkaline media. |
| Orysastrobin | Hydrolysis $DT_{50}$ >365 d |
| Kresoxim-methyl | Hydrolysis $\overline{DT_{50}}$ 34 d (pH 7), 7 h (pH 9); relatively stable at pH 5. |
| Trifloxystrobin | Hydrolysis $DT_{50}$ 27.1 h (pH 9), 11.4 w (pH 7); stable at pH 5 (all 20° C.) |

Solubility

Strobilurins are typically very poorly soluble in water, usually with parts per million (ppm) or lower level solubility. They have higher solubility in polar organic solvents such as acetone, methanol, or acetonitrile. See Table 3 for a list of typical strobilurins and their solubility in different common solvents (taken from the e-pesticide manual, Ver. 5. British Crop Protection Council).

TABLE 3

Solubility of some exemplary strobilurins in common solvents and octanol-water partition coefficients and melting temperatures

| Strobilurin | Solubility | $K_{OW}$ | $T_{melting}$ (° C.) |
|---|---|---|---|
| Fluxastrobin | water 2.56 (unbuffered), 2.29 (pH 7) mg/l (20° C.). In dichloromethane >250, xylene 38.1, isopropanol 6.7, n-heptane 0.04 (all in g/l, 20° C.). | logP = 2.86 (20° C.) | 103-108° C. |
| Fenamidone | water 7.8 mg/l (20° C.). In acetone 250, acetonitrile 86.1, dichloromethane 330, methanol 43, n-octanol 9.7 (all in g/l, 20° C.). | logP = 2.8 (20° C.) | 136.8° C. |

TABLE 3-continued

Solubility of some exemplary strobilurins in common solvents and
octanol-water partition coefficients and melting temperatures

| Strobilurin | Solubility | $K_{OW}$ | $T_{melting}$ (° C.) |
|---|---|---|---|
| Azoxystrobin | water 6 mg/l (20° C.). In hexane 0.057, n-octanol 1.4, methanol 20, toluene 55, acetone 86, ethyl acetate 130, acetonitrile 340, dichloromethane 400 (all in g/l, 20° C.). | logP = 2.5 (20° C.) | 116° C.; (tech., 114-116° C.) |
| Picoxystrobin | water 3.1 mg/l (20° C.). In methanol 96, 1,2-dichloroethane, acetone, xylene and ethyl acetate >250 (all in g/l, 20° C.). | logP = 3.6 (20° C.) | 75° C. |
| Enestroburin | Insoluble in water. Very soluble in acetone, ether and chloroform. | — | — |
| Pyraclostrobin | water 1.9 mg/l (20° C.). In n-heptane 3.7, isopropanol 30.0, octanol 24.2, olive oil 28.0, methanol 100.8, acetone, ethyl acetate, acetonitrile, dichloromethane and toluene >500 (all in g/l, 20° C.). | logP = 3.99 (20° C.) | 63.7-65.2° C. |
| Famoxadone | water 52 (unbuffered water, pH 7.8-8.9), 243 (pH 5), 111 (pH 7), 38 (pH 9) (all in µg/l, 20° C.). In acetone 274, toluene 13.3, dichloromethane 239, hexane 0.048, methanol 10, ethyl acetate 125.0, n-octanol 1.78, acetonitrile 125 (all in g/l, 25° C.). | logP = 4.65 (pH 7) | 141.3-142.3° C. |
| Dimoxystrobin | water 4.3 (pH 5.7), 3.5 (pH 8.0) (both in mg/l, 20° C.). In dichloromethane >250, DMF 200-250, acetone 67-80, acetonitrile 50-57, ethyl acetate 33-40, toluene 20-25, methanol 20-25, isopropanol, n-heptane, n-octanol and olive oil all <10 (all in g/l, 20° C.). | logP = 3.59 (pH 6.5) | 138.1-139.7° C. |
| Metominostrobin | water 0.128 g/l (20° C.). In dichloromethane 1380, chloroform 1280, DMSO 940 (all in g/l, 25° C.). | logP = 2.32 (20° C.) | 87-89° C. |
| Orysastrobin | water 80.6 mg/l (20° C.). | logP = 2.36 (20° C.) | 98.4-99.0° C. |
| Kresoxim-methyl | water 2 mg/l (20° C.). In n-heptane 1.72, methanol 14.9, acetone 217, ethyl acetate 123, dichloromethane 939 (all in g/l solvent, 20° C.). | logP = 3.4 (pH 7, 25° C.) | 101.6-102.5° C. |
| Trifloxystrobin | water 610 µg/l (25° C.). In acetone, dichloromethane and ethyl acetate >500, hexane 11, methanol 76, octanol 18, toluene 500 (all in g/l, 25° C.). | logP = 4.5 (25° C.) | 72.9° C. |

Because strobilurins have such low water solubility they need to be formulated to disperse in water before they can be applied to a plant or fungus.

Soil Mobility

Most strobilurins are substantially immobile in soil and are unlikely to move via leaching. It has been shown that for some strobilurins, close to 85% of the fungicide actually remains in the application zone itself even after several hundred millimeters of rainfall (ref: Pest. Manag. Sci. 2009, 65: 1009-1014); however, although some of the degradation products (from hydrolysis, photolysis or microbial degradation) show increased mobility, these are typically less toxic or effective at controlling fungi than the parent compound. Without wishing to be bound by any theory, the low soil mobility is thought to be primarily due to the strobilurin's non-polar nature and lack of water solubility. When strobilurins are dispersed in water they therefore have a tendency to associate with natural organic matter found in soils and, once bound to the top soil's organic matter, exhibit low mobility within the surrounding soil matrix.

General information about specific strobilurin soil persistence and soil mobility can be found in literature (Pest. Manag. Sci (2009) 65: 1009-1014; Environ. Monit. Assess (2010)162: 219-224). This lack of soil mobility limits the fungi that can be targeted with strobilurins, especially some soil-borne fungi that may reside beneath the top soil area such as R. solanyi for sugar beets (Journal of Sugar Beet Research, V41 (1-2), 17-36), M. poae and other patch-causing fungi in turf such as L. korrae and R. cerealis (University of Guelph Pest Diagnostic Clinic Fact Sheet: Necrotic Ring Spot It would therefore be desirable to provide strobilurin formulations that have moderate soil mobility to allow the active to penetrate in the soil matrix.

Plant Uptake and Weak Systemic Effect

Fungicides can either be contact, translaminar or systemic. Contact fungicides are not taken up into the plant tissue, and only protect the plant where the spray is deposited. Translaminar fungicides redistribute the fungicide from the upper, sprayed leaf surface to the lower, unsprayed surface of the same leaf. Systemic fungicides are taken up and redistributed through the xylem vessels to the upper parts of the plant. Systemic activity is necessary to provide curative performance for a fungicide. Most strobilurin compounds are weakly systemic, and thus are mainly used as protectants. Further, some strobilurins are weakly translaminar and to a certain extent, weakly systemic (e.g., curative) fungicides. Strobilurins are known to be highly effective against spore germination and early penetration of the host e.g., show good preventative activity, but once the fungus has started to grow inside the leaf tissue, strobilurins have little (especially for weakly systemic strobilurins) or no effect.

When the strobilurin is applied to the plant, most of the active ingredient is initially held on or within the waxy cuticle of the plant surface. If the strobilurin is showing weak systemic activity, this is because the active ingredient penetrates into the underlying plant cells (translaminar movement) and also moves to local zones above the point of uptake (local systemization via the xylem in the leaf). The uptake of the strobilurin into the cells of the leaf following application is dependent on several factors: the formulation type, active ingredient particle size, the additives/adjuvants used in the formulation, the other active ingredients mixed in or with the formulation, the target crop (leaf type, surface, weathering and plant age) and environmental factors that influence the drying of the spray droplet (Paul Vincelli, 2002. $Q_oI$(Strobilurin) Fungicides: Benefits and Risks. *The Plant Health Instructor.* DOI:10.1094/PHI-1-2002-089-02.)

Strobilurins are also non-systemic from root uptake; that is, they do not get taken up from the root and distributed throughout the plant tissue. This can be problematic, as it means that any plant tissue that needs to be protected by the strobilurin formulation needs to be efficiently covered during the application process (typically spray). Unfortunately, aerial spray or foliar spray is often non-uniform and does not lead to complete coverage of the exterior of the plant (e.g., see Henriet and Baur, *Bayer Crop Science Journal* 62(2): 243, 2009). In addition, as plants grow they develop new foliar tissue that was not treated with the strobilurin and hence will not be protected from fungal infection until the next application. The degree of system activity can be demonstrated by evaluating the performance of the strobilurin for curative activity; improvements in curative activity can be correlated with improvements in systemization.

If a strobilurin could be made more systemic through improvements in formulation it would dramatically improve the impact of strobilurins on target crops because of the potentially reduced application rates and enhanced efficacy of such formulations.

Fungicide Resistance

All strobilurins are site specific fungicides and only block the electron transfer at the site of quinol oxidation in the cytochrome $bc_1$ complex—preventing ATP formation in the fungus which leads to its eventual death. Because the mode of action of strobilurins is highly specific, i.e., it targets only a single metabolic pathway in the fungus, there are instances where mutations can occur in certain fungal species that can make them resistant to strobilurins. If such a resistant strain occurs, repeated application of the strobilurin can lead to a buildup of a strobilurin-resistant subpopulation in an entire crop/plantation. There are two types of fungicide resistance: quantitative and qualitative. Quantitatively resistant pathogens are less sensitive to the fungicide compared to the wild type, but can still be controlled with a higher use rate and/or more frequent applications. On the other hand, qualitatively resistant strains are insensitive/unresponsive to the fungicide and can no longer be controlled at labeled field rates. To slow the rate of proliferation of resistant strains, it is useful to limit the consecutive applications of strobilurin fungicides to the earlier stages of fungal infection as well as applying a second type of fungicide that possesses another mode of action. It is therefore useful to provide strobilurin formulations that can easily be mixed with another type of fungicide that has a different mode of action to help reduce the risk of resistant strains. In addition, improved formulations that are more effective at lower rates, show longer-lasting activity, or can be applied less frequently due to improvements in systemic activity can also decrease issues with resistance due to decreased application intervals.

Plant Health and Hidden Disease

Growers strive to obtain high yielding and high quality plants and crops. Toward this goal, agricultural strategies are utilized to maintain, optimize, and enhance plant health from the time of planting through to harvest. As a descriptive term, plant health refers to the overall condition of a plant, including its size, sturdiness, optimum maturity, consistency in growth pattern and reproductive activity. Growers often also define plant health in terms of measurable outputs, such as enhanced crop yield and economic return on production input.

As the effective control of fungal disease is of central importance in improving and optimizing plant health and crop yield, strobilurin fungicides are often applied as part of regimes directed towards achieving these results. Plant health applications of strobilurins may include preventative inoculations to optimize disease control, inoculations for the purpose of combating hidden disease, inoculations under conditions that are favorable for the development of disease (e.g., favorable weather conditions), insurance applications, and other applications to improve crop yield and quality. For example, preventative applications of strobilurin fungicides, such as azoxystrobin, are often performed on row crops to prevent fungal infections. Furthermore, environmental conditions are closely and constantly monitored by growers, and upon tending towards circumstances that are favorable for fungal infections, strobilurin applications are performed.

Of central importance to the improvement of plant health via the application of strobilurin fungicides is combating hidden or undiagnosed disease. Growers have implicated hidden diseases (i.e., cases in which the crop has below detection limit or non-obvious fungal infection) in reduced and variable crop yields. In response, strobilurin fungicides are often used in plant health applications such as insurance applications (e.g., applications that are made regardless of disease pressure), particularly on high potential crops such as soybean and corn. In many cases these have been found to reverse or dampen the effects of hidden disease on crops and improve yield.

There are, however, persistent challenges related to the use of strobilurins in improving plant health by combating hidden disease, the most problematic of which are related to correct timing of application and low or insufficient levels of curative activity. For example, prior to early strobilurin applications (e.g., the first application of the season), there is often a level of latent infection or hidden disease in the crop. In such cases, commercial formulations that demonstrate preventative activity but that suffer from low or less than adequate levels of curative activity would be ineffective at improving plant health by combating hidden disease. To compensate in part for their low curative activity, commercial formulations are sometimes applied at increased rates. Furthermore, plant physiology and pathology are extremely complex, and there remain unanswered questions surrounding the optimal time points for application of fungicides to improve plant health by combating hidden disease.

It would thus be desirable to develop strobilurin formulations that provide increased levels of curative activity for plant health applications, including the treatment of latent and hidden fungal disease. For example, it would be useful to produce strobilurin formulations that have increased levels of curative activity by imparting systemic properties to a strobilurin or improving the systemic properties of the fungicide. Such formulations would be more effective in plant health applications and could therefore be used at lower effective dose rates than currently available commercial formulations. Furthermore, it would be useful to provide strobilurin formulations that could in part mitigate the difficulties associated with correct timing of fungicide applications directed to improving plant health. For example, formulations that display enhanced residual activity would increase the window of opportunity for successful application timing.

Formulations—Generally

Several synthetic strobilurins (including azoxystrobin, trifloxystrobin, pyraclostrobin, and kresoxim-methyl) formulations are now available commercially, and the bulk of which are used in agricultural applications. Despite a common mode of action, strobilurins exhibit definite practical differences, e.g., different mobility in the plant. As an example, azoxystrobin is weakly systemic; trifloxystrobin is not systemic but can move to the other side of the leaf and can even affect surrounding foliage (i.e., it is translaminar).

The aforementioned limitations of strobilurins, and their formulations, when used as fungicides manifest themselves in (a) how they are currently applied to plants and (b) how they are formulated by manufacturers. As an example, because strobilurins are susceptible to degradation (either from photolysis, hydrolysis or exposure of field conditions) end users (e.g., farmers or golf course maintenance managers) need to apply strobilurins more often than if they were longer lasting. As another example, because strobilurins lack systemic activity (which would help protect new growth of crops), end users need to continually re-apply strobilurins in order to protect crops from fungal infection. Similarly, strobilurins will also need to be re-applied in certain cases because some strobilurin formulations are not rainfast or sufficiently rainfast and may easily get washed off the foliage if heavy rainfall occurs soon after application. Furthermore, because of the inherent threat of forming strobilurin resistant strains, end users need strobilurin formulations that that can easily be mixed with other types of formulated fungicides as well as formulations that have improved residual activity (i.e., would need less applications). These limitations are compounded by increasing pressure on end users who are faced with increasing regulatory and consumer pressure to use fewer pesticides and/or fungicides and in lower quantities.

In order to address these limitations, a variety of complicated formulation techniques and formulation agents have been developed to counter to the UV instability, water insolubility, non-systemic nature, and low soil mobility of strobilurins.

In order for a strobilurin to be efficiently applied to a plant or fungus, the strobilurin product needs to be dispersible in water. The two most common formulation techniques to do this are to produce either an emulsifiable concentrate (EC) or a suspension concentrate (SC). An EC is a formulation where the active ingredient is dissolved in a suitable solvent in the presence of surfactants. When the EC is dispersed into the spray tank and agitated, the surfactants emulsify the solvent into water, and the active ingredient is delivered in the solvent phase to the plant or fungus. A SC is a high-solids concentrate in water. The active ingredient is milled into particles that are 1-10 microns (Alan Knowles, *Agrow Reports: New Developments in Crop Protection Product Formulation*. London: Agrow Reports May 2005). These solid particles are then dispersed into water at high concentration using surfactants. After adding the SC into the spray tank, the surfactant-stabilized particles disperse into water and are applied (still as solid particles) to the leaf surface. Other common formulation techniques used for some crop protection active ingredients include microencapsulations (CS) and emulsions (EW or OW). Solid formulation techniques that are currently used include water-dispersible granules (WG) or powders (WP), where the active ingredient is absorbed to a dispersible carrier that is provided dry to the farmer. When mixed into the spray tank, the carrier disperses into the water, carrying the active ingredient with it. Particle sizes for these carriers can be anywhere in the range of 1-10 microns (Alan Knowles, *Agrow Reports: New Developments in Crop Protection Product Formulation*. London: Agrow Reports May 2005).

As an alternative to these approaches, we have developed new classes strobilurin formulations. As demonstrated in the Examples and as discussed below, in some embodiments these new strobilurin formulations are more dispersible in water, do not have UV blockers, have enhanced stability (i.e., longer lasting), are rainfast and have improved mobility in soil. In some embodiments, these new strobilurin formulations have increased curative (systemic) and preventative performance, are compatible with other agricultural products (surfactants, leaf wetters, fertilizers, etc), and are stable in non-ideal solution conditions such high salt, extreme pH, hard water, elevated temperatures, etc. These enhancements/improvements in the formulation can also help address the resistance of some fungi by being (1) compatible with a second fungicide, either tank-mixed or pre-mixed in the original formulation and (2) requiring less fungicide in each application. In general, these new strobilurin formulations comprise nanoparticles (optionally in aggregate form) of polymer-associated strobilurins along with various formulating agents. Before discussing in detail various embodiments of the chemical and physical characteristics of these nanoparticles and formulating agents we turn to some general considerations of our strobilurin formulations.

First, we note that for many of the aforementioned applications of strobilurins the end user would prefer to receive a dry powder or granulated product containing the strobilurin. Solid products are not only less expensive and easier to store and ship, but, generally, handling and environment risks (e.g., spills) are reduced as compared to liquid formulations. The dry product is typically added to water in the spray tank, agitated, and applied to the plant or fungus. It is useful that the dry product disperse quickly in the spray tank and that there be as little as possible or no non-dispersible fraction (which can sediment or cake and can cause problems with spray equipment). Although granulation formulations are common in the art, it is important to note that individual formulations are not necessarily transferable from one active to another. Each active and application may need a different formulation, which can vary according to the target fungus, the crop to which it is applied, the geography of its application, applicable regulatory structure, and intensity of infestation among other factors. Formulation development, even with well known actives, is a complex and empirical process.

Second, formulation development (e.g., of granulation formulations) using strobilurins and nanoparticles of polymer-associated active ingredient is non-trivial. In particular, traditional granulation processes are not particularly suitable to strobilurins and nanoparticles of polymer-associated active ingredient. For example, traditional granulation of water-insoluble active ingredients normally involves first absorbing the active ingredient to a water-dispersible or water-soluble carrier, followed by addition of the other granulation ingredients and granulating. With our formulations, we do not use a traditional carrier. In addition, active ingredients with low melting points are difficult to granulate because the heat applied or generated during extrusion tends to melt the active ingredient and cause separation during granulation. As shown in Table 3, many strobilurins have low melting points and can therefore suffer from this problem. Using nanoparticles of polymer-associated strobilurin compounds was found to facilitate the granulation of these otherwise difficult to granulate actives ingredients by eliminating the need for low temperature granulation equipment (to prevent melting of the active). It was also found to facilitate the granulation of semi-solid or even liquid active ingredients. Surprisingly, during granulation no phase separation or apparent melting of these active ingredients occurred. In fact, even if the granules were heated to above the melting point of the active ingredient no phase separation or apparent melting of the active ingredient occurred. Without wishing to be bound by theory, it is thought that the presence of the polymer nanoparticles provides a stable environment for the active ingredients (even when the formulation is brought to a temperature above the active's melting point), preventing phase separation.

Third, in some embodiments, in order to make a water-dispersible granulated formulation with nanoparticles of polymer-associated active ingredient it was necessary to add a dispersant and a wetting agent. Although formulation agents, such as dispersants and wetting agents are known in the art, the selection of particular compounds and amounts for nanoparticles of polymer-associated active ingredient is non-trivial. Some dispersants, for example, were found to give rise to a negative effect in our formulations, e.g., dispersants like Soprophor BSU which are known to help decrease the particle size in standard granulated formulations unexpectedly gave rise to larger aggregates in our formulations. Furthermore, the addition of a salt (e.g., phosphate buffered saline solution) was necessary in certain cases to maintain the stability of the formulation. This was surprising since normally, the addition of salt would cause the precipitation of the active ingredient (salting out effect).

Fourth, we have managed to produce high active ingredient (e.g., 20-50 weight %) content solid formulations using the nanoparticles of polymer-associated active ingredient. This is, in general, quite difficult to achieve using traditional solid formulating techniques, particularly if the active ingredient has a low melting point or is not solid at room temperature. Traditionally, in order to have such high active content formulations that have acceptable qualities such as rapid dispersion in water, adequate stability when dispersed, long-term storage stability, etc., a suspension concentrate is needed. Suspension concentrate formulations, though, have several problems ranging from the hydrolysis of the active ingredient, lower shelf life, and temperature sensitivity. Some active ingredients cannot be produced as suspension concentrates, because of the low melting point of the active ingredient. Low-melting active ingredients tend to be less stable over long term storage. Additionally, active ingredients with moderate or high water solubility are difficult to formulate as suspension concentrates because they have a tendency to recrystallize and increase in particle size over time, causing stability problems. Solid formulations do not suffer from hydrolysis issues because the formulation is nearly devoid of water. As shown in the Examples, our solid formulations are stable to temperature cycling and do not show any recrystallization or phase separation of the active ingredient even after repeated temperature cycling. In light of these results our solid formulations are expected to have a long shelf life.

Fifth, as an alternative to the aforementioned solid formulations we have also prepared high-concentration liquid suspensions (HSLS). These high-concentration liquid suspensions contain a significant amount of active ingredient associated with polymer nanoparticles and are added to water in a spray tank, agitated, and applied to the plant or fungus. These formulations look like the traditional suspension concentrates that are discussed above and available from many manufacturers. However, because the nanoparticles of polymer-associated active ingredient, the formulations are prepared in different ways, described below, as compared to the traditional methods. Traditional suspension concentrates are milled surfactant-stabilized formulations of hard solid crystalline particles. In our case, because the polymer is a compressible, solvent-swellable solid, traditional methods would not work. Instead, we typically first manufacture the polymer nanoparticles, load them with active ingredient, and form the high-concentration liquid suspension either by drying the loaded polymer nanoparticles (with formulation agents if necessary) and re-suspending at the desired concentration. Alternatively, high concentration liquid suspensions with our polymer nanoparticles can be made by using water as the solvent during the loading process and removing water until the loaded polymer nanoparticles are at the desired concentration. Traditional suspension concentrates also require an anti-settling agent or thickener such as xanthan gum. The gum provides a polymer network that helps stabilize the micron-sized particles of active ingredient and prevent settling and coalescence. In our formulations, this is not required, because our particle size is smaller (nano vs. micro size) and hence settling and coalescence is less of a problem. In addition, without wishing to be limited by any theory, it is thought that the polymer nanoparticles themselves can help stabilize the formulation when dispersed at high concentration in water.

Sixth, because our formulations are based around nanoparticles of polymer-associated active ingredients, we can help improve the skin sensitization or irritation issue for some strobilurins as mentioned above. Indeed, we have found that if skin exposure occurs they can be rinsed off more effectively than with traditional formulations such as EC formulations.

Seventh, because our formulations are based around nanoparticles of polymer-associated active ingredients, they are stable to relatively high salt conditions. Stability in high salt conditions is required especially when the formulation is to be mixed with other secondary agricultural products such as a concentrated fertilizer mix, exposed to high salt conditions (e.g., used in or with hard waters) mixed with other formulations (other pesticides, fungicides, and herbicides) or mixed with other tank-mix adjuvants. The ability to mix our formulations with other products can be beneficial to the end user because simultaneous agricultural products can be applied in a single application.

Eighth, our formulations are rainfast. Without wishing to be bound by theory, polymer-associated active ingredients have an enhanced affinity to the target areas of the plant (and fungus). When the formulation is applied to a plant/fungus and then exposed to rain, the enhanced affinity can prevent washing off due to rain.

Formulations—Components

In various aspects, the present disclosure provides formulations that comprise nanoparticles (optionally in aggregate form) of polymer-associated active ingredient along with various formulating agents.

Active Ingredient

As used herein, the term "active ingredient" ("ai", "AI") refers to strobilurin compounds (i.e., strobilurins). Strobilurins are natural substances isolated mainly from mushrooms of the genera *strobilurus*. Structurally, the basic common feature in this family is the presence of (E)-β-methoxyacrylate group. Many strobilurins have the following general structure:

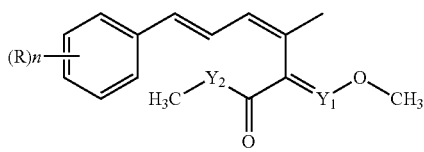

where R, n, Y1 and Y2 all vary depending on the strobilurin (see Balba, H. J Envi. Sci. Heath. Part B. 2007, 42, 441.) Some synthetic strobilurin analogs feature the replacement of the (E)-β-methoxyacrylate group with a methoxyimino-acetate group as shown below:

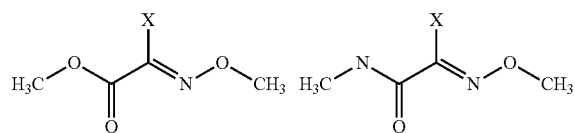

Where X is typically n aromatic ring with varying substituents (see Balba, H. J Envi. Sci. Heath. Part B. 2007, 42, 441).

Azoxystrobin has the following structure:

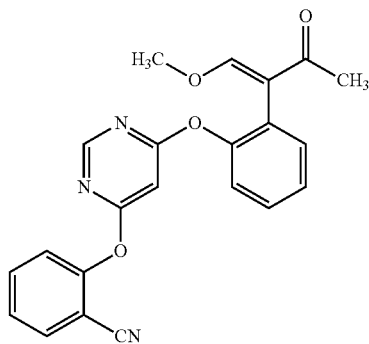 [SMILES: CO/C=C(/C(C)=O)c1ccccc1Oc1cc(Oc2ccccc2C#N)ncn1]

Non-limiting examples of strobilurin compounds are: fluoxastrobin, (E)-{2-[6-(2-chlorophenoxy)-5-fluoropyrimidin-4-yloxy]phenyl}(5,6-dihydro-1,4,2-dioxazin-3-yl)methanone O-methyloxime; fenamidone, (S)-1-anilino-4-methyl-2-methylthio-4-phenylimidazolin-5-one; azoxystrobin, methyl(E)-2-{2-[6-(2-cyanophenoxy)pyrimidin-4-yloxy]phenyl}-3-methoxyacrylate; picoxystrobin, methyl(E)-3-methoxy-2-[2-(6-trifluoromethyl-2-pyridyloxymethyl)phenyl]acrylate; enestrobin, methyl 2-{2-[3-(4-chlorophenyl)-1-methylallylideneaminooxymethyl]phenyl}-3-methoxyacrylate; pyraclostrobin, methyl N-{2-[1-(4-chlorophenyl)pyrazol-3-yloxymethyl]phenyl}(N-methoxy)carbamate; famoxadone, 3-anilino-5-methyl-5-(4-phenoxyphenyl)-1,3-oxazolidine-2,4-dione; dimoxystrobin, (E)-2-(methoxyimino)-N-methyl-2-[α-(2,5-xylyloxy)-o-tolyl]acetamide; metominostrobin, (E)-2-methoxyimino-N-methyl-2-(2-phenoxyphenyl)acetamide; orysastrobin, 2[(E)-methoxyimino]-2-[(3E,6E)-2-{5-[(E)-methoxyimino]-4,6-dimethyl-2,8-dioxa-3,7-diazanona-3,6-dienyl}phenyl]-N-methylacetamide; kresoxim-methyl, methyl(E)-methoxyimino[2-(o-tolyloxymethyl)phenyl]acetate; trifloxystrobin, and methyl(E)-methoxyimino-{(E)-α-[1-(α,α,α-trifluoro-m-tolyl)ethylideneaminooxy]-o-tolyl}acetate.

Nanoparticles of Polymer-Associated Active Ingredient

As used herein, the terms "nanoparticles of polymer-associated active ingredient", "nanoparticles of polymer-associated strobilurin compound" or "active ingredient associated with polymer nanoparticles" refer to nanoparticles comprising one or more collapsed polymers that are associated with the active ingredient. In some embodiments the collapsed polymers are cross-linked. As discussed below, in some embodiments, our formulations may include aggregates of nanoparticles. Exemplary polymers and methods of preparing nanoparticles of polymer-associated active ingredient are described more fully below.

In some embodiments, the active ingredient is associated with preformed polymer nanoparticles. The associating step may involve dispersing the polymer nanoparticles in a first solvent and then dispersing the active ingredient in a second solvent that is miscible or partially miscible with the first solvent, mixing the two dispersions and then either removing the second or first solvent from the final mixture. In some embodiments, all the solvent is removed by vacuum evaporation, freeze drying or spray drying. The associating step may also involve dispersing both the preformed polymer nanoparticles and active ingredients in a common solvent and removing all or a portion of the common solvent from the final mixture.

In some embodiments, the associating step may involve milling the active ingredient in the presence of pre-formed polymer nanoparticles. It is surprising that if the active ingredient alone is milled under these conditions; the resulting particle size is significantly larger than if it is milled in the presence of pre-formed polymer nanoparticles. In general, size reduction processes such as milling do not enable the production of particle sizes that are produced via milling in the presence of nanoparticles of the current disclosure. Without wishing to be bound by any theory, it is thought that interaction between the active ingredient and the nanoparticles during the milling process facilitates the production of smaller particles than would be formed via milling in the absence of the nanoparticles.

Non-limiting examples of milling methods that may be used for the association step can be found in U.S. Pat. No. 6,604,698 and include ball milling, bead milling, jet milling, media milling, and homogenization, as well as other milling methods known to those of skill in the art. Non-limiting examples of mills that can be for the association step include attritor mills, ball mills, colloid mills, high pressure homogenizers, horizontal mills, jet mills, swinging mills, and vibratory mills. In some embodiments, the associating step may involve milling the active ingredient in the presence of pre-formed polymer nanoparticles and an aqueous phase. In some embodiments, the associating step may involve wet or dry milling of the active ingredient in the presence of pre-formed nanoparticles. In some embodiments, the association step may involve milling the active ingredient and pre-formed polymer nanoparticles in the presence of one or more formulating agents.

In general and without limitation, the active ingredient may be associated with regions of the polymer nanoparticle that elicit a chemical or physical interaction with the active ingredient. Chemical interactions can include hydrophobic interactions, affinity pair interactions, H-bonding, and van der Waals forces. Physical interactions can include entanglement in polymer chains and/or inclusion within the polymer nanoparticle structure. In some embodiments, the active ingredient can be associated in the interior of the polymer nanoparticle, on the surface of the polymer nanoparticle, or both the surface and the interior of the polymer nanoparticle. Furthermore, the type of association interactions between the active ingredient and the polymer nanoparticle can be probed using spectroscopic techniques such as NMR, IR, UV-vis, and emission spectroscopies. For example, in cases where the strobilurin active ingredient is normally crystalline when not associated with the polymer nanoparticles, the nanoparticles of polymer-associated strobilurin compounds typically do not show the endothermic melting peak or show a reduced endothermic melting peak of the pure crystalline active ingredient as seen in differential thermal analysis (DTA) or differential scanning calorimetry (DSC) measurements (see, e.g., FIG. 1 which is discussed in the Examples).

Nanoparticles of polymer-associated active ingredients can be prepared with a range of average diameters, e.g., between about 1 nm and about 500 nm. The size of the nanoparticles can be adjusted in part by varying the size and number of polymers that are included in the nanoparticles. In some embodiments, the average diameter ranges from about 1 nm to about 10 nm, from about 1 nm to about 20 nm, from about 1 nm to about 30 nm, from about 1 nm to about 50 nm, from about 10 nm to about 50 nm, from about 10 nm to about 100 nm, from about 20 nm to about 100 nm, from about 20 nm to about 100 nm, from about 50 nm to about 200 nm, from about 50 nm to about 250 nm, from about 50 nm to about 300 nm, from about 100 nm to about 250 nm, from about 100 nm to about 300 nm, from about 200 nm to about 300 nm, from about 200 nm to about 500 nm, from about 250 nm to about 500 nm, and from about 300 nm to about 500 nm. These and other average diameters described herein are based on volume average particle sizes that were measured in solution by dynamic light scattering on a Malvern Zetasizer ZS in CIPAC D water, 0.1M NaCl, or in deionized water at 200 ppm active concentration. Various forms of microscopies can also be used to visualize the sizes of the nanoparticles such as atomic force microscopy (AFM), transmission electron microscopy (TEM), scanning electron microscopy (SEM) and optical microscopy.

In some embodiments, the aggregates have an average particle size between about 10 nm and about 5,000 nm when dispersed in water under suitable conditions. In some embodiments, the aggregates have an average particle size between about 10 nm and about 1,000 nm. In some embodiments, the aggregates have an average particle size between about 10 nm and about 500 nm. In some embodiments, the aggregates have an average particle size between about 10 nm and about 300 nm. In some embodiments, the aggregates have an average particle size between about 10 nm and about 200 nm. In some embodiments, the aggregates have an average particle size between about 50 nm and about 5,000 nm. In some embodiments, the aggregates have an average particle size between about 50 nm and about 1,000 nm. In some embodiments, the aggregates have an average particle size between about 50 nm and about 500 nm. In some embodiments, the aggregates have an average particle size between about 50 nm and about 300 nm. In some embodiments, the aggregates have an average particle size between about 50 nm and about 200 nm. In some embodiments, the aggregates have an average particle size between about 100 nm and about 5,000 nm. In some embodiments, the aggregates have an average particle size between about 100 nm and about 1,000 nm. In some embodiments, the aggregates have an average particle size between about 100 nm and about 500 nm. In some embodiments, the aggregates have an average particle size between about 100 nm and about 300 nm. In some embodiments, the aggregates have an average particle size between about 100 nm and about 200 nm. In some embodiments, the aggregates have an average particle size between about 500 nm and about 5000 nm. In some embodiments, the aggregates have an average particle size between about 500 nm and about 1000 nm. In some embodiments, the aggregates have an average particle size between about 1000 nm and about 5000 nm. Particle size can be measured by the techniques described above.

As described in detail in the examples, in some embodiments, pre-formed polymer nanoparticles that have been associated with active ingredient to generate nanoparticles or aggregates of nanoparticles of polymer-associated active ingredients (associated nanoparticles) can be recovered after extraction of the active ingredient. In some embodiments, the active ingredient can be extracted from nanoparticles or aggregates of nanoparticles of polymer-associated active ingredient by dispersing the associated nanoparticles in a solvent that dissolves the active ingredient but that is known to disperse the un-associated, preformed nanoparticles poorly or not at all. In some embodiments, after extraction and separation, the insoluble nanoparticles that are recovered have a size that is smaller than the nanoparticles or aggregates of nanoparticles of polymer-associated active ingredients as measured by DLS. In some embodiments, after extraction and separation, the insoluble nanoparticles that are recovered have a size that is similar or substantially the same as the size of original pre-formed polymer nanoparticles (prior to association) as measured by DLS. In some embodiments, the nanoparticles are prepared from poly (methacrylic acid-co-ethyl acrylate). In some embodiments, the active ingredient is azoxystrobin. In some embodiments, the extraction solvent is acetonitrile.

It should be understood that the association step to generate nanoparticles of polymer associated active ingredient need not necessarily lead to association of the entire fraction the active ingredient in the sample with pre-formed polymer nanoparticles (not all molecules of the active ingredient in the sample must be associated with polymer nanoparticles after the association step). Likewise, the association step need not necessarily lead to the association of the entire fraction of the pre-formed nanoparticles in the sample with active ingredient (not all nanoparticle molecules in the sample must be associated with the active ingredient after the association step).

Similarly, in formulations comprising nanoparticles of polymer-associated active, the entire fraction of active ingredient in the formulation need not associated with pre-formed polymer nanoparticles (not all molecules of the active ingredient in the sample must be associated with polymer nanoparticles in the formulation). Likewise, in formulations comprising nanoparticles of polymer-associated active ingredient, the entire fraction of pre-formed polymer nanoparticles in the formulation need not be associated with active ingredient (not all of nanoparticle molecules in the sample must be associated with the active ingredient in the formulation).

In some embodiments, the nanoparticles are prepared using a polymer that is a polyelectrolyte. Polyelectrolytes are polymers that contain monomer units of ionized or ionizable functional groups, they can be linear, branched, hyperbranched or dendrimeric, and they can be synthetic or naturally occurring. Ionizable functional groups are functional groups that can be rendered charged by adjusting solution conditions, while ionized functional group refers to chemical functional groups that are charged regardless of solution conditions. The ionized or ionizable functional group can be cationic or anionic, and can be continuous along the entire polymer chain (e.g., in a homopolymer), or can have different functional groups dispersed along the polymer chain, as in the case of a co-polymer (e.g., a random co-polymer). In some embodiments, the polymer can be made up of monomer units that contain functional groups that are either anionic, cationic, both anionic and cationic, and can also include other monomer units that impart a specific desirable property to the polymer.

In some embodiments, the polyelectrolyte is a homopolymer. Non limiting examples of homopolymer polyelectrolytes include: poly(acrylic acid), poly(methacrylic acid), poly(styrene sulfonate), poly(ethyleneimine), chitosan, poly(dimethylammonium chloride), poly(allylamine hydrochloride), and carboxymethyl cellulose.

In some embodiments, the polyelectrolyte is a co-polymer. Non limiting examples of co-polymer polyelectrolytes include: poly(methacrylic acid co-ethyl acrylate); poly(methacrylic acid-co-styrene); poly(methacrylic acid-co-butylmethacrylate); poly[acrylic acid-co-poly(ethylene glycol) methyl ether methacrylate]; or poly(n-butylmethacrylcate-co-methacrylic acid).

In some embodiments, the polyelectrolyte can be made from one or more monomer units to form homopolymers, copolymers or graft copolymers of: ethylene; ethylene glycol; ethylene oxide; carboxylic acids including acrylic acid, methacrylic acid, itaconic acid, and maleic acid; polyoxyethylenes or polyethyleneoxide; and unsaturated ethylenic mono or dicarboxylic acids; lactic acids; amino acids; amines including dimethlyammonium chloride, allylamine hydrochloride; methacrylic acid; ethyleneimine; acrylates including methyl acrylate, ethyl acrylate, propyl acrylate, n-butyl acrylate ("BA"), isobutyl acrylate, 2-ethyl acrylate, and t-butyl acrylate; methacrylates including ethyl methacrylate, n-butyl methacrylate, and isobutyl methacrylate; acrylonitriles; methacrylonitrile; vinyls including vinyl acetate, vinylversatate, vinylpropionate, vinylformamide, vinylacetamide, vinylpyridines, and vinyllimidazole; vinylnapthalene, vinylnaphthalene sulfonate, vinylpyrrolidone, vinyl alcohol; aminoalkyls including aminoalkylacrylates, aminoalkylsmethacrylates, and aminoalkyl(meth)acrylamides; styrenes including styrene sulfonate; d-glucosamine; glucaronic acid-N-acetylglucosamine; N-isopropylacrylamide; vinyl amine. In some embodiments, the polyelectrolyte polymer can include groups derived from polysaccharides such as dextran, gums, cellulose, or carboxymethyl cellulose.

In some embodiments, the polyelectrolyte comprises poly(methacrylic acid-co-ethyl acrylate) polymer. In some embodiments, the mass ratio of methacrylic acid to ethyl acrylate in the poly(methacrylic acid-co-ethyl acrylate) polymer is between about 50:50 and about 95:5. In some embodiments, the mass ratio of methacrylic acid to ethyl acrylate in the poly(methacrylic acid-co-ethyl acrylate) polymer is between about 70:30 and about 95:5. In some embodiments, the mass ratio of methacrylic acid to ethyl acrylate in the poly(methacrylic acid-co-ethyl acrylate) polymer is between about 80:20 and about 95:5. In some embodiments, the mass ratio of methacrylic acid to ethyl acrylate in the poly(methacrylic acid-co-ethyl acrylate) polymer is between about 85:15 and about 95:5.

In some embodiments, the polyelectrolyte comprises poly(methacrylic acid-co-styrene) polymer. In some embodiments, the mass ratio of methacrylic acid to styrene in the poly(methacrylic acid-co-styrene) polymer is between about 50:50 and about 95:5. In some embodiments, the mass ratio of methacrylic acid to styrene in the poly(methacrylic acid-co-styrene) polymer is between about 70:30 and about 95:5. In some embodiments, the mass ratio of methacrylic acid to styrene in the poly(methacrylic acid-co-styrene) polymer is between about 80:20 and about 95:5. In some embodiments, the mass ratio of methacrylic acid to styrene in the poly(methacrylic acid-co-styrene) polymer is between about 85:15 and about 95:5.

In some embodiments, the mass ratio of methacrylic acid to butyl methacrylate in the poly(methacrylic acid-co-butylmethacrylate) polymer is between about 50:50 and about 95:5. In some embodiments, the mass ratio of methacrylic acid to butyl methacrylate in the poly(methacrylic acid-co-butylmethacrylate) polymer is between about 70:30 and about 95:5. In some embodiments, the mass ratio of methacrylic acid to butyl methacrylate in the poly(methacrylic acid-co-butylmethacrylate) polymer is between about 80:20 and about 95:5. In some embodiments, the mass ratio of methacrylic acid to butyl methacrylate in the poly(methacrylic acid-co-butylmethacrylate) polymer is between about 85:15 and about 95:5.

In some embodiments, the homo or co-polymer is water soluble at pH 7. In some embodiments, the polymer has solubility in water above about 1 weight %. In some embodiments, the polymer has solubility in water above about 2 weight %. In some embodiments, the polymer has solubility in water above about 3 weight %. In some embodiments, the polymer has solubility in water above about 4 weight %. In some embodiments, the polymer has solubility in water above about 5 weight %. In some embodiments, the polymer has solubility in water above about 10 weight %. In some embodiments, the polymer has solubility in water above about 20 weight %. In some embodiments, the polymer has solubility in water above about 30 weight %. In some embodiments, the polymer has solubility in water between about 1 and about 30 weight %. In some embodiments, the polymer has solubility in water between about 1 and about 10 weight %. In some embodiments, the polymer has solubility in water between about 5 and about 10 weight %. In some embodiments, the polymer has solubility in water between about 10 and about 30 weight %. In some embodiments the solubility of the polymer in water can also be adjusted by adjusting pH or other solution conditions in water.

In some embodiments, the polyelectrolyte polymer has a weight average ($M_w$) molecular weight between about 100,000 and about 4,000,000 Daltons. In some embodiments, the polyelectrolyte polymer has a weight average molecular weight between about 100,000 and about 2,000,000 Daltons. In some embodiments, the polyelectrolyte polymer has a weight average molecular weight between about 100,000 and about 1,000,000 Daltons. In some embodiments, the polyelectrolyte polymer has a weight average molecular weight between about 100,000 and about 750,000 Daltons. In some embodiments, the polyelectrolyte polymer has a weight average molecular weight between about 100,000 and about 500,000 Daltons. In some embodiments, the polyelectrolyte polymer has a weight average molecular weight between about 100,000 and about 200,000 Daltons. In some embodiments, the polyelectrolyte polymer has a weight average molecular weight between about 200,000 and about 2,000,000 Daltons. In some embodiments, the polyelectrolyte polymer has a weight average molecular weight between about 200,000 and about 1,000,000 Daltons. In some embodiments, the polyelectrolyte polymer has a weight average molecular weight between about 200,000 and about 500,000 Daltons. In some embodiments, the polyelectrolyte polymer has a weight average molecular weight between about 300,000 and about 2,000,000 Daltons. In some embodiments, the polyelectrolyte polymer has a weight average molecular weight between about 300,000 and about 1,000,000 Daltons. In some embodiments, the polyelectrolyte polymer has a weight average molecular weight between about 300,000 and about 500,000 Daltons.

In some embodiments, the apparent molecular weight of the polyelectrolyte polymer (e.g., the molecular weight determined via certain analytical measurements such as size exclusion chromatography or DLS) is lower than the actual molecular weight of a polymer due to crosslinking within the polymer. In some embodiments, a crosslinked polyelectrolyte polymer of the present disclosure might have a higher actual molecular weight than the experimentally determined apparent molecular weight. In some embodiments, a crosslinked polyelectrolyte polymer of the present disclosure might be a high molecular weight polymer despite having a low apparent molecular weight.

Nanoparticles of polymer-associated active ingredients and/or aggregates of these nanoparticles can be part of a formulation in different amounts. The final amount will depend on many factors including the type of formulation (e.g., liquid or solid, granule or powder, concentrated or not, etc.). In some instances the nanoparticles (including both the polymer and active ingredient components) make up between about 1 and about 98 weight % of the total formulation. In some embodiments, the nanoparticles make up between about 1 and about 90 weight % of the total formulation. In some embodiments, the nanoparticles make up between about 1 and about 75 weight % of the total formulation. In some embodiments, the nanoparticles make up between about 1 and about 50 weight % of the total formulation. In some embodiments, the nanoparticles make up between about 1 and about 30 weight % of the total formulation. In some embodiments, the nanoparticles make up between about 1 and about 25 weight % of the total formulation. In some embodiments, the nanoparticles make up between about 1 and about 10 weight % of the total formulation. In some embodiments, the nanoparticles make up between about 10 and about 25 weight % of the total formulation. In some embodiments, the nanoparticles make up between about 10 and about 30 weight % of the total formulation. In some embodiments, the nanoparticles make up between about 10 and about 50 weight % of the total formulation. In some embodiments, the nanoparticles make up between about 10 and about 75 weight % of the total formulation. In some embodiments, the nanoparticles make up between about 10 and about 90 weight % of the total formulation. In some embodiments, the nanoparticles make up between about 10 and about 98 weight % of the total formulation. In some embodiments, the nanoparticles make up between about 25 and about 50 weight % of the total formulation. In some embodiments, the nanoparticles make up between about 25 and about 75 weight % of the total formulation. In some embodiments, the nanoparticles make up between about 25 and about 90 weight % of the total formulation. In some embodiments, the nanoparticles make up between about 30 and about 98 weight % of the total formulation. In some embodiments, the nanoparticles make up between about 50 and about 90 weight % of the total formulation. In some embodiments, the nanoparticles make up between about 50 and about 98 weight % of the total formulation. In some embodiments, the nanoparticles make up between about 75 and about 90 weight % of the total formulation. In some embodiments, the nanoparticles make up between about 75 and about 98 weight % of the total formulation.

In some embodiments, the nanoparticles of polymer-associated active ingredients are prepared according to a method disclosed in United States Patent Application Publication No. 20100210465, the entire contents of which are incorporated herein by reference. In some embodiments, polymer nanoparticles without active ingredients are made by collapse of a polyelectrolyte with a collapsing agent and then rendering the collapsed conformation permanent by intra-particle cross-linking. The active ingredient is then associated with this pre-formed polymer nanoparticle. In some embodiments, the formulation contains the same amount (by weight) of active ingredient and polymer, while in other embodiments the ratio of active ingredient to polymer (by weight) can be between about 1:10 and about 10:1, between about 1:10 and about 1:5, between about 1:5 and about 1:4, between about 1:4 and about 1:3, between about 1:3 and about 1:2, between about 1:2 and about 1:1, between about 1:5 and about 1:1, between about 5:1 and about 1:1, between about 2:1 and about 1:1, between about 3:1 and about 2:1, between about 4:1 and about 3:1, between about 5:1 and about 4:1, between about 10:1 and about 5:1, between about 1:3 and about 3:1, between about 5:1 and about 1:1, between about 1:5 and about 5:1, or between about 1:2 and about 2:1.

As noted above, in some embodiments, the associating step may involve dispersing the polymer nanoparticles in a first solvent, dispersing the active ingredient in a second solvent that is miscible or partially miscible with the first solvent, mixing the two dispersions and then either removing the second or first solvent from the final mixture.

Alternatively, in some embodiments, the associating step may involve dispersing both the pre-formed polymer nanoparticles and active ingredient in a common solvent and removing all or a portion of the common solvent from the final mixture. The final form of the nanoparticles of polymer-associated active ingredient can be either a dispersion in a common solvent or a dried solid. The common solvent is typically one that is capable of swelling the polymer nanoparticles as well as dissolving the active ingredient at a concentration of at least about 10 mg/mL, e.g., at least about 20 mg/mL. The polymer nanoparticles are typically dispersed in the common solvent at a concentration of at least about 10 mg/mL, e.g., at least about 20 mg/mL. In some embodiments, the common solvent is an alcohol (either long or short chain), preferably methanol or ethanol. In some embodiments the common solvent is selected from alkenes, alkanes, alkynes, phenols, hydrocarbons, chlorinated hydrocarbons, ketones, and ethers. In some embodiments, the common solvent is a mixture of two or more different solvents that are miscible or partially miscible with each other. Some or all of the common solvent is removed from the dispersion of pre-formed polymer nanoparticles and active ingredients by either direct evaporation or evaporation under reduced pressure. The dispersion can be dried by a range of processes known by a practitioner of the art such as lyophilization (freeze-drying), spray-drying, tray-drying, evaporation, jet drying, or other methods to obtain the nanoparticles of polymers-associated with active ingredients. In general, the amount of solvent that is removed from the dispersion described above will depend on the final type of formulation that is desired. This is illustrated further in the Examples and in the general description of specific formulations.

In some instances the solids content (including both the polymer and active ingredient components as well as other solid form formulating agents) of the formulation is between about 1 and about 98 weight % of the total formulation. In some embodiments, the solids content of the formulation is between about 1 and about 90 weight % of the total formulation. In some embodiments, the solids content of the formulation is between about 1 and about 75 weight % of the total formulation. In some embodiments, the solids content of the formulation is between about 1 and about 50 weight % of the total formulation. In some embodiments, the solids content of the formulation is between about 1 and about 30 weight % of the total formulation. In some embodiments, the solids content of the formulation is between about 1 and about 25 weight % of the total formulation. In some embodiments, the solids content of the formulation is between about 1 and about 10 weight % of the total formulation. In some embodiments, the solids content of the formulation is between about 10 and about 25 weight % of the total formulation. In some embodiments, the solids content of the formulation is between about 10 and about 30 weight % of the total formulation. In some embodiments, the solids content of the formulation is between about 10 and about 50 weight % of the total formulation. In some embodiments, the solids content of the formulation is between about 10 and about 75 weight % of the total formulation. In some embodiments, the solids content of the formulation is between about 10 and about 90 weight % of the total formulation. In some embodiments, the solids content of the formulation is between about 10 and about 98 weight % of the total formulation. In some embodiments, the solids content of the formulation is between about 25 and about 50 weight % of the total formulation. In some embodiments, the solids content of the formulation is between about 25 and about 75 weight % of the total formulation. In some embodiments, the solids content of the formulation is between about 25 and about 90 weight % of the total formulation. In some embodiments, the solids content of the formulation is between about 30 and about 98 weight % of the total formulation. In some embodiments, the solids content of the formulation is between about 50 and about 90 weight % of the total formulation. In some embodiments, the solids content of the formulation is between about 50 and about 98 weight % of the total formulation. In some embodiments, the solids content of the formulation is between about 75 and about 90 weight % of the total formulation. In some embodiments, the solids content of the formulation is between about 75 and about 98 weight % of the total formulation.

Formulating Agents

As used herein, the term "formulating agent" refers to any other material used in the formulation other than the nanoparticles of polymer-associated active ingredient. Formulating agents can include, but are not limited to, compounds that can act as a dispersants or wetting agents, inert fillers, solvents, surfactants, anti-freezing agents, anti-settling agents or thickeners, disintegrants, and preservatives.

In some embodiments, a formulation may include a dispersant or wetting agent or both. In some embodiments the same compound may act as both a dispersant and a wetting agent. A dispersant is a compound that helps the nanoparticles (or aggregates of nanoparticles) disperse in water. Without wishing to be bound by any theory, dispersants are thought to achieve this result by absorbing on to the surface of the nanoparticles and thereby limiting re-aggregation. Wetting agents increase the spreading or penetration power of a liquid when placed onto the substrate (e.g., leaf). Without wishing to be bound by any theory, wetting agents are thought to achieve this result by reducing the interfacial tension between the liquid and the substrate surface.

In a similar manner, some formulating agents may demonstrate multiple functionality. The categories and listings of specific agents below are not mutually exclusive. For example, fumed silica, described below in the thickener/anti-settling agent and anti-caking agent sections, is typically used for these functions. In some embodiments, however, fumed silica demonstrates the functionality of a wetting agent and/or dispersant. Specific formulating agents listed below are categorized based on their primary functionality, however, it is to be understood that particular formulating agents may exhibit multiple functions. Certain formulation ingredients display multiple functionalities and synergies with other formulating agents and may demonstrate superior properties in a particular formulation but not in another formulation.

In some embodiments, a dispersant or wetting agent is selected from organosilicones (e.g., SYLGARD 309 from Dow Corning Corporation or SILWET L77 from Union Carbide Corporation) including polyalkylene oxide modified polydimethylsiloxane (SILWET L7607 from Union Carbide Corporation), methylated seed oil, and ethylated seed oil (e.g., SCOIL from Agsco or HASTEN from Wilfarm), alkylpolyoxyethylene ethers (e.g., ACTIVATOR 90), alkylarylalolates (e.g., APSA 20), alkylphenol ethoxylate and alcohol alkoxylate surfactants (e.g., products sold by Huntsman), fatty acid, fatty ester and fatty amine ethoxylates (e.g., products sold by Huntsman), products sold by Cognis such as sorbitan and ethoxylated sorbitan esters, ethoxylated vegetable oils, alkyl, glycol and glycerol esters and glycol ethers, tristyrylphenol ethoxylates, anionic surfactants such as sulfonates, such as sulfosuccinates, alkylaryl sulphonates, alkyl napthalene sulfonates (e.g., products sold by Adjuvants Unlimited), calcium alkyl benzene sulphonates, and phosphate esters (e.g., products sold by Huntsman Chemical or BASF), as salts of sodium, potassium, ammonium, magnesium, triethanolamine (TEA), etc.

Other specific examples of the above sulfates include ammonium lauryl sulfate, magnesium lauryl sulfate, sodium 2-ethyl-hexyl sulfate, sodium actyl sulfate, sodium oleyl sulfate, sodium tridecyl sulfate, triethanolamine lauryl sulfate, ammonium linear alcohol, ether sulfate ammonium nonylphenol ether sulfate, and ammonium monoxynol-4-sulfate. Other examples of dispersants and wetting agents include, sulfo succinamates, disodium N-octadecylsulfo-succinamate; tetrasodium N-(1,2-dicarboxyethyl)-N-octadecylsulfo-succinamate; diamyl ester of sodium sulfosuccinic acid; dihexyl ester of sodium sulfosuccinic acid; and dioctyl esters of sodium sulfosuccinic acid; dihexyl ester of sodium sulfosuccinic acid; and dioctyl esters of sodium sulfosuccinic acid; castor oil and fatty amine ethoxylates, including sodium, potassium, magnesium or ammonium salts thereof. Dispersants and wetting agents also include natural emulsifiers, such as lecithin, fatty acids (including sodium, potassium or ammonium salts thereof) and ethanolamides and glycerides of fatty acids, such as coconut diethanolamide and coconut mono- and diglycerides. Dispersants and wetting agents also include sodium polycarboxylate (commercially available as Geropon TA/72); sodium salt of naphthalene sulfonate condensate (commercially available as Morwet (D425, D809, D390, EFW); calcium naphthalene sulfonates (commercially available as DAXAD 19LCAD); sodium lignosulfonates and modified sodium lignosulfonates; aliphatic alcohol ethoxylates; ethoxylated tridecyl alcohols (commercially available as Rhodasurf (BC420, BC610, BC720, BC 840); Ethoxylated tristeryl phenols (commercially available as Soprophor BSU); sodium methyl oleyl taurate (commercially available as Geropon T77); tristyrylphenol ethoxylates and esters; ethylene oxide-propylene oxide block copolymers; non-ionic block copolymers (commercially available as Atlox (4912). Examples of dispersants and wetting agents include, but are not limited to, sodium dodecylbenzene sulfonate; N-oleyl N-methyl taurate; 1,4-dioctoxy-1,4-dioxo-butane-2-sulfonic acid; sodium lauryl sulphate; sodium dioctyl sulphosuccinate; aliphatic alcohol ethoxylates; nonylphenol ethoxylates. Dispersants and wetting agents also include sodium taurates; and sodium or ammonium salts of maleic anhydride copolymers, ligno-sulfonic acid formulations or condensed sulfonate sodium, potassium, magnesium or ammonium salts, polyvinylpyrrolidone (available commercially as POLYPLASDONE XL-10 from International Specialty Products or as KOLLIDON Cl M-10 from BASF Corporation), polyvinyl alcohols, modified or unmodified starches, methylcellulose, hydroxyethyl or hydroxypropyl methylcellulose, carboxymethyl methylcellulose, or combinations, such as a mixture of either lignosulfonic acid formulations or condensed sulfonate sodium, potassium, magnesium or ammonium salts with polyvinylpyrrolidone (PVP).

In some embodiments, the dispersants and wetting agents can combine to make up between about 1 and about 30 weight % of the formulation. For example, dispersants and wetting agents can make up between about 1 and about 20 weight %, about 1 and about 10 weight %, between about 1 and about 5 weight %, between about 1 and about 3 weight %, between about 2 and about 30 weight %, between about 2 and about 20 weight %, between about 2 and about 10 weight %, between about 3 and about 30 weight %, between about 3 and about 20 weight %, between about 3 and about 10 weight %, between about 3 and about 5 weight %, between about 5 and about 30 weight %, between about 5 and about 20 weight %, between about 5 and about 10 weight % of the formulation. In some embodiments, dispersants or wetting agents can make up between about 0.1 and 1 weight % of the formulation.

In some embodiments, a formulation may include an inert filler. For example, an inert filler may be included to produce or promote cohesion in forming a wettable granule formulation. An inert filler may also be included to give the formulation a certain active loading, density, or other similar physical properties. Non limiting examples of inert fillers that may be used in a formulation include bentonite clay, carbohydrates, proteins, lipids synthetic polymers, glycolipids, glycoproteins, lipoproteins, lignin, lignin derivatives, and combinations thereof. In a preferred embodiment the inert filler is a lignin derivative and is optionally calcium lignosulfonate. In some embodiments, the inert filler is selected from the group consisting of: monosaccharides, disaccharides, oligosaccharides, polysaccharides and combinations thereof. Specific carbohydrate inert fillers illustratively include glucose, mannose, fructose, galactose, sucrose, lactose, maltose, xylose, arabinose, trehalose and mixtures thereof such as corn syrup; sugar alcohols including: sorbitol, xylitol, ribitol, mannitol, galactitol, fucitol, iditol, inositol, volemitol, isomalt, maltitol, lactitol, polyglycitol; celluloses such as carboxymethylcellulose, ethylcellulose, hydroxyethylcellulose, hydroxy-methylethylcellulose, hydroxyethylpropylcellulose, methylhydroxyethylcellulose, methylcellulose; starches such as amylose, seagel, starch acetates, starch hydroxyethyl ethers, ionic starches, long-chain alkyl starches, dextrins, amine starches, phosphates starches, and dialdehyde starches; plant starches such as corn starch and potato starch; other carbohydrates such as pectin, amylopectin, xylan, glycogen, agar, alginic acid, phycocolloids, chitin, gum arabic, guar gum, gum karaya, gum tragacanth and locust bean gum; vegetable oils such as corn, soybean, peanut, canola, olive and cotton seed; complex organic substances such as lignin and nitrolignin; derivatives of lignin such as lignosulfonate salts illustratively including calcium lignosulfonate and sodium lignosulfonate and complex carbohydrate-based formulations containing organic and inorganic ingredients such as molasses. Suitable protein inert fillers illustratively include soy extract, zein, protamine, collagen, and casein. Inert fillers operative herein also include synthetic organic polymers capable of promoting or producing cohesion of particle components and such inert fillers illustratively include ethylene oxide polymers, polyacrylamides, polyacrylates, polyvinyl pyrrolidone, polyethylene glycol, polyvinyl alcohol, polyvinylmethyl ether, polyvinyl acrylates, polylactic acid, and latex.

In some embodiments, a formulation contains between about 1 and about 90 weight % inert filler, e.g., between about 1 and about 80 weight %, between about 1 and about 60 weight %, between about 1 and about 40 weight %, between about 1 and about 25 weight %, between about 1 and about 10 weight %, between about 10 and about 90 weight %, between about 10 and about 80 weight %, between about 10 and about 60 weight %, between about 10 and about 40 weight %, between about 10 and about 25 weight %, between about 25 and about 90 weight %, between about 25 and about 80 weight %, between about 25 and about 60 weight %, between about 25 and about 40 weight %, between about 40 and about 90 weight %, between about 40 and about 80 weight %, or between about 60 and about 90 weight %.

In some embodiments, a formulation may include a solvent or a mixture of solvents that can be used to assist in controlling the solubility of the active ingredient itself, the nanoparticles of polymer-associated active ingredients, or other components of the formulation. For example, the solvent can be chosen from water, alcohols, alkenes, alkanes, alkynes, phenols, hydrocarbons, chlorinated hydrocarbons, ketones, ethers, and mixtures thereof. In some embodiments, the formulation contains a solvent or a mixture of solvents that makes up about 0.1 to about 90 weight % of the formulation. In some embodiments, a formulation contains between about 0.1 and about 90 weight % solvent, e.g., between about 1 and about 80 weight %, between about 1 and about 60 weight %, between about 1 and about 40 weight %, between about 1 and about 25 weight %, between about 1 and about 10 weight %, between about 10 and about 90 weight %, between about 10 and about 80 weight %, between about 10 and about 60 weight %, between about 10 and about 40 weight %, between about 10 and about 25 weight %, between about 25 and about 90 weight %, between about 25 and about 80 weight %, between about 25 and about 60 weight %, between about 25 and about 40 weight %, between about 40 and about 90 weight %, between about 40 and about 80 weight %, between about 60 and about 90 weight %, between about 0.1 and about 10 weight %, between about 0.1 and about 5 weight %, between about 0.1 and about 3 weight %, between about 0.1 and about 1 weight %, between about 0.5 and about 20 weight %, 0 between about. 5 and about 10 weight %, between about 0.5 and about 5 weight %, between about 0.5 and about 3 weight %, between about 0.5 and about 1 weight %, between about 1 and about 20 weight %, between about 1 and about 10 weight %, between about 1 and about 5 weight %, between about 1 and about 3 weight %, between about 5 and about 20 weight %, between about 5 and about 10 weight %, between about 10 or about 20 weight %.

In some embodiments, a formulation may include a surfactant. When included in formulations, surfactants can function as wetting agents, dispersants, emulsifying agents, solubilizing agents and bioenhancing agents. Without limitation, particular surfactants may be anionic surfactants, cationic surfactants, nonionic surfactants, amphoteric surfactants, silicone surfactants (e.g., Silwet L77), and fluorosurfactants. Exemplary anionic surfactants include alkylbenzene sulfonates, alkyl sulfonates and ethoxylates, sulfosuccinates, phosphate esters, taurates, alkylnaphthalene sulfonates and polymers lignosulfonates. Exemplary nonionic surfactants include alkylphenol ethoxylates, aliphatic alcohol ethoxylates, aliphatic alkylamine ethoxylates, amine alkoxylates, sorbitan esters and their ethoxylates, castor oil ethoxylates, ethylene oxide/propylene oxide copolymers and polymeric surfactants. In some embodiments, surfactants can make up between about 1 about 20 weight % of the formulation, e.g., between about 1-15 weight %, b54etween about 1 and about 10 weight %, between about 1 and about 8 weight %, between about 1 and about 6 weight %, between about 1 and about 4 weight %, between about 3 and about 20 weight %, between about 3 and about 15 weight %, between about 3 and about 10 weight %, between about 3 and about 8 weight %, between about 3 and about 6 weight %, between about 5 and about 15 weight %, between about 5 and about 10 weight %, between about 5 and about 8 weight %, or between about 10 and about 15 weight %. In some embodiments, a surfactant (e.g., a non-ionic surfactant) may be added to a formulation by the end user, e.g., in a spray tank. Indeed, when a formulation is added to the spray tank it becomes diluted and, in some embodiments, it may be advantageous to add additional surfactant in order to maintain the nanoparticles in dispersed form.

In some embodiments, a formulation may include an anti-settling agent or thickener that can help provide stability to a liquid formulation or modify the rheology of the formulation. Examples of anti-settling agents or thickeners include, but are not limited to, guar gum; locust bean gum; xanthan gum; carrageenan; alginates; methyl cellulose; sodium carboxymethyl cellulose; hydroxyethyl cellulose; modified starches; polysaccharides and other modified polysaccharides; polyvinyl alcohol; glycerol alkyd resins such as Latron B-1956 from Rohm & Haas Co., plant oil based materials (e.g., cocodithalymide) with emulsifiers; polymeric terpenes; microcrystalline cellulose; methacrylates; poly(vinylpyrrolidone), syrups, polyethylene oxide, and fumed silica (e.g., Aerosil 380). In some embodiments, anti-settling agents or thickeners can make up between about 0.05 and about 10 weight % of the formulation, e.g., about 0.05 to about 5 weight %, about 0.05 to about 3 weight %, about 0.05 to about 1 weight %, about 0.05 to about 0.5 weight %, about 0.05 to about 0.1 weight %, about 0.1 to about 5 weight %, about 0.1 to about 3 weight %, about 0.1 to about 1 weight %, about 0.1 to about 0.5 weight %, about 0.5 to about 5 weight %, about 0.5 to about 3 weight %, about 0.5 to about 1 weight %, about 1 to about 10 weight %, about 1 to about 5 weight %, or about 1 to about 3 weight %. In some embodiments, it is explicitly contemplated that a formulation of the present disclosure does not include a compound whose primary function is to act as an anti-settling or thickener. In some embodiments, compounds included in a formulation may have some anti-settling or thickening functionality, in addition to other, primary functionality, so anti-settling or thickening functionality is not a necessary condition for exclusion, however, formulation agents used primarily or exclusively as anti-settling agents or thickeners may be expressly omitted from the formulations.

In some embodiments, a formulation may include one or more preservatives that prevent microbial or fungal degradation of the product during storage. Examples of preservatives include but are not limited to, tocopherol, ascorbyl palmitate, propyl gallate, butylated hydroxyanisole (BHA), butylated hydroxytoluene (BHT), propionic acid and its sodium salt; sorbic acid and its sodium or potassium salts; benzoic acid and its sodium salt; p-hydroxy benzoic acid sodium salt; methyl p-hydroxy benzoate; 1,2-benzisothiazalin-3-one, and combinations thereof. In some embodiments, preservatives can make up about 0.01 to about 0.2 weight % of the formulation, e.g., between about 0.01 and about 0.1 weight %, between about 0.01 and about 0.05 weight %, between about 0.01 and about 0.02 weight %, between about 0.02 and about 0.2 weight %, between about 0.02 and about 0.1 weight %, between about 0.02 and about 0.05 weight %, between about 0.05 and about 0.2 weight %, between about 0.05 and about 0.1 weight %, or between about 0.1 and about 0.2 weight %.

In some embodiments, a formulation may include anti-freezing agents, anti-foaming agents, and/or anti-caking agents that help stabilize the formulation against freezing during storage, foaming during use, or caking during storage. Examples of anti-freezing agents include, but are not limited to, ethylene glycol, propylene glycol, and urea. In certain embodiment a formulation may include between about 0.5 and about 10 weight % anti-freezing agents, e.g., between about 0.5 and about 5 weight %, between about 0.5 and about 3 weight %, between about 0.5 and about 2 weight %, between about 0.5 and about 1 weight %, between about 1 and about 10 weight %, between about 1 and about 5 weight %, between about 1 and about 3 weight %, between about 1 and about 2 weight %, between about 2 and about 10 weight %, between about 3 and about 10 weight %, or between about 5 and about 10 weight %.

Examples of anti-foaming agents include, but are not limited to, silicone based anti-foaming agents (e.g., aqueous emulsions of dimethyl polysiloxane, FG-10 from Dow-Corning®, Trans 10A from Trans-Chemo Inc.), and non-silicone based anti-foaming agents such as octanol, nonanol, and silica. In some embodiments a formulation may include between about 0.05 and about 5 weight % of anti-foaming agents, e.g., between about 0.05 and about 0.5 weight %, between about 0.05 and about 1 weight %, between about 0.05 and about 0.2 weight %, between about 0.1 and about 0.2 weight %, between about 0.1 and about 0.5 weight %, between about 0.1 and about 1 weight %, or between about 0.2 and about 1 weight %.

Examples of anti-caking agents include sodium or ammonium phosphates, sodium carbonate or bicarbonate, sodium acetate, sodium metasilicate, magnesium or zinc sulfates, magnesium hydroxide (all optionally as hydrates), sodium alkylsulfosuccinates, silicious compounds, magnesium compounds, C10-C22 fatty acid polyvalent metal salt compounds, and the like. Illustrative of anti-caking ingredients are attapulgite clay, kieselguhr, silica aerogel, silica xerogel, perlite, talc, vermiculite, sodium aluminosilicate, zirconium oxychloride, starch, sodium or potassium phthalate, calcium silicate, calcium phosphate, calcium nitride, aluminum nitride, copper oxide, magnesium carbonate, magnesium silicate, magnesium nitride, magnesium phosphate, magnesium oxide, magnesium nitrate, magnesium sulfate, magnesium chloride, and the magnesium and aluminum salts of C10-C22 fatty acids such as palmitic acid, stearic acid and oleic acid. Anti-caking agents also include refined kaolin clay, amorphous precipitated silica dioxide, such as HI SIL 233 available from PPG Industries, refined clay, such as HUBERSIL available from Huber Chemical Company, or fumed silica (e.g., Aerosil 380) In some embodiments, a formulation may include between about 0.05 and about 10 weight % anti-caking agents, e.g., between about 0.05 to 5 weight %, between about 0.05 and about 3 weight %, between about 0.05 and about 2 weight %, between about 0.05 and about 1 weight %, between about 0.05 and about 0.5 weight %, between about 0.05 and about 0.1 weight %, between about 0.1 and about 5 weight %, between about 0.1 and about 3 weight %, between about 0.1 and about 2 weight %, between about 0.1 and about 1 weight %, between about 0.1 and about 0.5 weight %, between about 0.5 and about 5 weight %, between about 0.5 and about 3 weight %, between about 0.5 and about 2 weight %, between about 0.5 and about 1 weight %, between about 1 to 3 weight %, between about 1 to 10 weight %, or between about 1 and about 5 weight %.

In some embodiments, a formulation may include a UV-blocking compound that can help protect the active ingredient from degradation due to UV irradiation. Examples of UV-blocking compounds include ingredients commonly found in sunscreens such as benzophenones, benzotriazoles, homosalates, alkyl cinnamates, salicylates such as octyl salicylate, dibenzoylmethanes, anthranilates, methyl benzylidenes, octyl triazones, 2-phenylbenzimidazole-5-sulfonic acid, octocrylene, triazines, cinnamates, cyanoacrylates, dicyano ethylenes, etocrilene, drometrizole trisiloxane, bisethylhexyloxyphenol methoxyphenol triazine, drometrizole, dioctyl butamido triazone, terephthalylidene dicamphor sulfonic acid and para-aminobenzoates as well as ester derivatives thereof, UV-absorbing metal oxides such as titanium dioxide, zinc oxide, and cerium oxide, and nickel organic compounds such as nickel bis(octylphenol) sulfide, etc. Additional examples of each of these classes of UV-blockers may be found in Kirk-Othmer, Encyclopedia of Chemical Technology. In some embodiments, a formulation may include between about 0.01 and about 2 weight % UV-blockers, e.g., between about 0.01 and about 1 weight %, between about 0.01 and about 0.5 weight %, between about 0.01 and about 0.2 weight %, between about 0.01 and about 0.1 weight %, between about 0.01 and about 0.05 weight %, between about 0.05 weight % and about 1 weight %, between about 0.05 and about 0.5 weight %, between about 0.05 and about 0.2 weight %, between about 0.05 and about 0.1 weight %, between about 0.1 and about 1 weight %, between about 0.1 and about 0.5 weight %, between about 0.1 and about 0.2 weight %, between about 0.2 and about 1 weight %, between about 0.2 and about 0.5 weight %, or between about 0.5 and about 1 weight %. In some embodiments, it is explicitly contemplated that a formulation of the present disclosure does not include a compound whose primary function is to act as a UV-blocker. In some embodiments, compounds included in a formulation may have some UV-blocking functionality, in addition to other, primary functionality, so UV-blocking is not a necessary condition for exclusion, however, formulation agents used primarily or exclusively as UV-blockers may be expressly omitted from the formulations.

In some embodiments, a formulation may include a disintegrant that can help a solid formulation break apart when added to water. Examples of suitable disintegrants include cross-linked polyvinyl pyrrolidone, modified cellulose gum, pregelatinized starch, cornstarch, modified corn starch (e.g., STARCH 1500) and sodium carboxymethyl starch (e.g., EXPLOTAB or PRIMOJEL), microcrystalline cellulose, sodium starch glycolate, sodium carboxymethyl cellulose, carmellose, carmellose calcium, carmellose sodium, croscarmellose sodium, carmellose calcium, carboxymethylstarch sodium, low-substituted hydroxypropyl cellulose, hydroxypropyl methylcellulose, hydroxypropyl cellulose, soy polysaccharides (e.g., EMCOSOY), alkylcellulose, hydroxyalkylcellulose, alginates (e.g., SATIALGINE), dextrans and poly(alkylene oxide) and an effervescent couple (e.g., citric or ascorbic acid plus bicarbonate), lactose, anhydrous dibasic calcium phosphate, dibasic calcium phosphate, magnesium aluminometasilicate, synthesized hydrotalcite, silicic anhydride and synthesized aluminum silicate. In some embodiments disintegrants can make up between about 1 and about 20 weight % of the formulation, e.g., between about 1 and about 15 weight %, between about 1 and about 10 weight %, between about 1 and about 8 weight %, between about 1 and about 6 weight %, between about 1 and about 4 weight %, between about 3 and about 20 weight %, between about 3 and about 15 weight %, between about 3 and about 10 weight %, between about 3 and about 8 weight %, between about 3 and about 6 weight %, between about 5 and about 15 weight %, between about 5 and about 10 weight %, between about 5 and about 8 weight %, or between about 10 and about 15 weight %.

Formulations

As described above, the nanoparticles of polymer-associated active ingredient can be formulated into different types of formulations for different applications. For example, the types of formulations can include wettable granules, wettable powders, and high solid liquid suspensions. Furthermore, as discussed above, formulation agents can include, but are not limited to dispersants, wetting agents, surfactants, anti-settling agents or thickeners, preservatives, anti-freezing agents, anti-foaming agents, anti-caking agents, inert fillers, and UV-blockers.

In some embodiments, a dispersion of polymer nanoparticles and active ingredient in a common solvent is dried (e.g., spray dried) to form a solid containing nanoparticles (optionally in aggregate form) of polymer-associated active ingredients. The spray dried solid can then be used as is or incorporated into a formulation containing other formulating agents to make a wettable granule (WG), wettable powder (WP), or a high solids liquid suspension (HSLS).

In some embodiments, active ingredient is milled in the presence of pre-formed polymer nanoparticles to form a solid containing nanoparticles (optionally in aggregate form) of polymer-associated active ingredients. The solid can then be used as is or incorporated into a formulation containing other formulating agents to make a wettable granule (WG), wettable powder (WP), or a high solids liquid suspension (HSLS). In some embodiments, the milling step may be performed in the presence of one or more formulating agents. In some embodiments, the milling step may be performed in the presence of an aqueous phase.

Wettable Granules (WG)

In some embodiments, the dried solid can be made into a formulation that is a wettable granule (WG) by adding other formulating agents and by extruding the formulation to form granules. In some embodiments, a WG formulation may be made by mixing together a dried (e.g., spray-dried, freeze dried, etc.) or milled solid comprising nanoparticles of polymer-associated active ingredient (or aggregates thereof), a wetting agent (e.g., a surfactant such as Sopropher 4D 384 or BSU) and/or a dispersant (e.g., a lignosulfonate such as Reax 88B, etc.) and an inert filler (e.g., lactose). In some embodiments a WG can be made using a wetting agent (e.g., a surfactant such as Sopropher 4D384 or BSU) and a dispersant (e.g., a lignosulfonate such as Reax 88B, etc.).

In some exemplary embodiments, described in more detail in the Examples section, the components of the WG formulation are all mixed in a vessel, moistened with about 30 to about 50% equivalent mass of water, and the resulting semi-solid is extruded to make granules. In some embodiments, the formulation of the final WG can be (by weight): 0-5% dispersant, 0-5% wetting agent, 5-80% nanoparticles of polymer-associated active ingredient (optionally in aggregate form), and inert filler to 100%. In some embodiments, the formulation of the final WG can be (by weight): 0.5-5% dispersant, 0.5%-5% wetting agent, 5-80% nanoparticles of polymer-associated active ingredient (optionally in aggregate form), and inert filler to 100%. As described above in the Formulating Agents and Nanoparticles of polymer-associated active ingredient sections, a wide variety of formulating agent(s) and various concentrations of nanoparticles (including aggregates), wetting agents, dispersants, fillers and other formulating agents can be used to prepare exemplary formulations, e.g. wettable granules.

In some embodiments, a WG formulation comprising nanoparticles of polymer-associated active ingredients (optionally in aggregate form) may be made by using a dispersion of polymer nanoparticles and active ingredient in a common solvent, preferably methanol. In some embodiments, a WG formulation can be made by adding the dispersion in common solvent into an aqueous solution containing a wetting agent (e.g., a surfactant such as Soprophor 4D 384 or BSU) and/or a dispersant (e.g., a lignosulfonate such as Reax 88B, etc.) and an inert filler (e.g., lactose), drying (freeze drying, spray drying, etc.) the resulting mixture to from a solid and then granulating the solid to obtain a WG formulation comprising nanoparticles of polymer-associated active ingredients (optionally in aggregate form). In some embodiments a WG can be made using a wetting agent (e.g., a surfactant such as Soprophor) and a dispersant (e.g., a lignosulfonate such as Reax 88B, etc.). As described above in the Formulating Agents section, a wide variety of formulating agent(s) and various concentrations of wetting agents, dispersants, fillers and other formulating agents can be used to prepare exemplary formulations, e.g. wettable granules.

In addition to the various polymer nanoparticles described above, exemplary polymer nanoparticles are made from a co-polymer of methacrylic acid and ethyl acrylate at a 90:10 mass ratio. In some embodiments, the polymer nanoparticles are made from a co-polymer of methacrylic acid and styrene at a 90:10 mass ratio. In some embodiments, the polymer nanoparticles are made from a co-polymer of methacrylic acid and butylmethacrylate at a 75:25 mass ratio. In some embodiments, the polymer nanoparticles are made from a co-polymer of acrylic acid and styrene at a 75:25 mass ratio. In some embodiments, the polymer nanoparticles are made from a co-polymer of acrylic acid and styrene at a 90:10 mass ratio. In some embodiments, the polymer nanoparticles are dispersed in a common solvent, in some cases at a concentration of 20 mg/mL or higher. As described above in the Nanoparticles of polymer-associated active ingredient section, many ratios of co-polymer constituents can be used.

In some exemplary embodiments, the active ingredient is selected from azoxystrobin, fenamidone, fluoxastrobin, kresoxim methyl, pyraclostrobin and trifloxystrobin. In some embodiments, the ratio of active ingredient to polymer nanoparticle is 1:1, 2:1, 3:1, 4:1 or 5:1, a range between these values or another range as listed above. As described above in the Nanoparticles of polymer-associated active ingredient section, many ratios of strobilurin to polymer can be used.

In some embodiments, the dispersion of polymer nanoparticles and active ingredient in a common solvent is slowly added to a vessel containing a second solvent, preferably water. In some embodiments, the second solvent is at least 20 times larger in volume than the common solvent containing the polymer nanoparticles and active ingredient. In some embodiments, the second solvent contains a dispersant, preferably but not limited to a lignosulfonate such as Reax 88B and/or a wetting agent, preferably but not limited to a surfactant such as sodium dodecylbenzene sulfonate and an inert filler, preferably but not limited to lactose.

In some embodiments, after the dispersion in a common solvent is mixed with the second solvent the solvents are removed by drying. In some embodiments, the solvents are removed by freeze drying. In some embodiments, the solvents are removed by spray drying. The resulting solid formulation is then moistened with about 30 to about 50% equivalent mass of water and is then extruded to form granules. In some exemplary embodiments, the granules are formed by hypodermic syringe extrusion. In some embodiments, the granules are formed through extrusion granulation, pan granulation, fluid bed granulation, spray drying granulation, or high shear granulation.

In some embodiments, the granules disperse in solution in 30 seconds or less. In some cases, the WG formulation has low friability. In some embodiments, the WG formulation has low dustiness. In some embodiments, when the WG formulation is dispersed in water, the dispersion results in nanoparticles with an average size within about 100 to about 500 nm, or in some cases, within about 100 to about 200 nm. In some embodiments, when the WG formulation is dispersed in water, the dispersion results in particles with an average size less than 100 nm. In some embodiments, a dispersion of the WG formulation in water creates minimal foam. In some embodiments, the WG formulation is stable after 1-2 months of continuous temperature cycling between −5° C. and 45° C. showing no visible signs of phase separation and can easily be dispersed in water at the use rate.

In some embodiments, the current disclosure provides methods of producing WGs comprising low melting-point actives via extrusion of the granules. In some embodiments, the active has a melting point of less than about 100° C., less than about 90° C., less than about 80° C., less than about 70° C., less than about 60° C., less than about 50° C. or less than about 40° C. It is surprising that wettable granules of low-melting point actives can be prepared via extrusion of the granules. As discussed above, the heat produced during extrusion generally leads to complications, such as separation of the active ingredient. In some embodiments, the active ingredient of the wettable granules of the current disclosure is picoxystrobin, pyraclostrobin, orysastrobin, metominostrobin or trifloxystrobin.

Wettable Powder (WP)

In some embodiments, the dried solid can be made into a formulation that is a wettable powder (WP). In some embodiments, a WP formulation comprising nanoparticles of polymer-associated active ingredients (optionally in aggregate form) can be made from a dried (e.g., spray dried, freeze dried, etc.) dispersion of polymer nanoparticles and active ingredient. In some embodiments, a WP formulation comprising nanoparticles of polymer-associated active ingredients (optionally in aggregate form) can be made from a milled solid comprising polymer nanoparticles of active ingredient. In some embodiments, a WP is made by mixing the dried solid with a dispersant and/or a wetting agent. In some embodiments, a WP is made by mixing the dried solid or milled solid with a dispersant and/or a wetting agent. In some embodiments, a WP is made by mixing the dried or milled solid with a dispersant and a wetting agent. In some embodiments, the formulation of the final WP can be (by weight): up to about 98% nanoparticles of polymer-associated active ingredients (including both the active ingredient and the polymer, optionally in aggregate form). In some embodiments, the WP formulation includes (by weight): 0-5% dispersant, 0-5% wetting agent, 5-98% nanoparticles of polymer-associated active ingredients (optionally in aggregate form), and inert filler to 100%. In some embodiments, the formulation of the final WP can be (by weight): 0.5-5% dispersant, 0.5%-5% wetting agent, 5-98% nanoparticles of polymer-associated active ingredients (optionally in aggregate form), and inert filler to 100%. As described above in the Formulating Agents and Nanoparticles of polymer-associated active ingredient sections, a wide variety of formulating agent(s) and various concentrations of nanoparticles (including aggregates), wetting agents, dispersants, fillers and other formulating agents can be used to prepare exemplary formulations, e.g. wettable granules.

In some embodiments, the formulation of the final WP can be (by weight): 0.5-5% dispersant, 0.5%-5% wetting agent, 0.1-10% thickener (e.g., fumed silica which, as noted above may serve multiple functions, and/or xanthan gum), 5-98% nanoparticles of polymer-associated active ingredients (optionally in aggregate form). As described above in the Formulating Agents section, a wide variety of formulating agent(s) and various concentrations of wetting agents, dispersants, fillers and other formulating agents can be used to prepare exemplary formulations, e.g. wettable powders.

In some exemplary embodiments, described in more detail below, a WP formulation comprising nanoparticles of polymer-associated active ingredients (optionally in aggregate form) may be made from a dispersion of polymer nanoparticles and active ingredient in a common solvent, preferably methanol. In some embodiments, the a WP formulation can be made by adding the dispersion in common solvent into a 1× Phosphate buffered saline (PBS) solution, and then drying (e.g., freeze drying, spray drying etc) the resulting mixture to form a solid powder. In some embodiments, a WP formulation can be made by adding the dispersion in common solvent into an aqueous solution containing a wetting agent (e.g., a surfactant such as sodium dodecylbenzene sulfonate) and/or a dispersant (e.g., a lignosulfonate such as Reax 88B, etc.) and optionally an inert filler (e.g., lactose), and then drying (e.g., freeze drying, spray drying, etc.) the resulting mixture to from a solid powder. In some embodiments a WP can be made using a wetting agent (e.g., a surfactant such as sodium dodecylbenzene sulfonate) and a dispersant (e.g., a lignosulfonate such as Reax 88B, etc.).

In some exemplary embodiments, also described in more detail below, the polymer nanoparticles are made from a co-polymer of methacrylic acid and ethyl acrylate at about a 90:10 mass ratio. In some embodiments, the polymer nanoparticles are dispersed in a common solvent, preferably at a concentration of 20 mg/mL. In some embodiments, the polymer nanoparticles are made from a co-polymer of methacrylic acid and styrene at about at a mass ratio of 75:25. In some embodiments, the polymer nanoparticles are made from a co-polymer of acrylic acid and styrene at about a 75:25 mass ratio. In some embodiments, the polymer nanoparticles are made from a co-polymer of acrylic acid and styrene at about a 90:10 mass ratio. In some embodiments, the active ingredient is azoxystrobin and is mixed into the polymer nanoparticle dispersion at a concentration of 20 mg/mL. As described above in the Nanoparticles of polymer-associated active ingredient section, many ratios of co-polymer constituents can be used.

In some embodiments, the dispersion of polymer nanoparticles and active ingredient is then slowly added into a vessel containing a second solvent, preferably water. In some embodiments, the second solvent is at least 20 times larger in volume than the common solvent containing the polymer nanoparticles and active ingredient. In some embodiments, the second solvent contains 1×PBS. In some embodiments, the second solvent contains a dispersant, preferably a lignosulfonate such as Reax 88B and/or a wetting agent, preferably a surfactant such as sodium dodecylbenzene sulfonate. In some embodiments a WP can be made using a wetting agent (e.g., a surfactant such as sodium dodecylbenzene sulfonate) and a dispersant (e.g., a lignosulfonate such as Reax 88B, etc.).

In some embodiments, after the dispersion of polymer nanoparticles and active ingredient in a common solvent is mixed with a second solvent containing dispersant and/or wetting agent, the final mixture is dried (e.g., freeze dried) to obtain a solid powdered formulation containing nanoparticles of polymer-associated active ingredients (optionally in aggregate form).

High Solids Liquid Suspension (HSLS)

One type of formulation that can be utilized according to the disclosure is a high solids liquid suspension. As described, such a formulation is generally characterized in that it is a liquid formulation that contains at least nanoparticles of polymer nanoparticles associated with active ingredient (includes potentially aggregates of the same).

In some embodiments, the formulation of the HSLS can be (by weight): between about 5 and about 80% nanoparticles of polymer-associated active ingredients (including both polymer and active ingredient, optionally in aggregate form), 0.5 and about 5% wetting agent and/or dispersant, between about 1 and about 10% anti-freezing agent, between about 0.2 and about 10% anti-settling agent or thickener, between about 0.1 and about 10% anti-foaming agent, between about 0.01 and about 0.1% preservative and water up to 100% As described above in the Formulating Agents and Nanoparticles of polymer-associated active ingredient sections, a wide variety of formulating agent(s) and various concentrations of nanoparticles (including aggregates), wetting agents, dispersants, fillers and other formulating agents can be used to prepare exemplary formulations, e.g., a HSLS.

In some exemplary embodiments, described in more detail below, the polymer nanoparticles are made from a co-polymer of methyl methacrylic acid and ethyl acrylate at a 90:10 mass ratio. In some embodiments, the polymer nanoparticles are dispersed in the common solvent, preferably at a concentration of 20 mg/mL. In some embodiments, the active ingredient is azoxystrobin, fenamidone, fluoxastrobin, kresoxim methyl, picoxystrobin, pyraclostrobin or trifloxystrobin and is mixed into the nanoparticle dispersion at a concentration of 20 mg/mL. As described above in the Nanoparticles of polymer-associated active ingredient section, many ratios of co-polymer constituents can be used.

In some embodiments, the dispersion of polymer nanoparticles and active ingredient in a common solvent is slowly added into a vessel containing a second solvent, preferably water. In some embodiments, the second solvent is at least 20 times larger in volume than the common solvent containing the polymer nanoparticles and active ingredient. In some embodiments, the second solvent contains a dispersant, preferably a lignosulfonate such as Reax 88B and/or a wetting agent, preferably a surfactant such as sodium dodecylbenzene sulfonate. In some embodiments a HSLS can be made using a wetting agent (e.g., a surfactant such as sodium dodecylbenzene sulfonate) and a dispersant (e.g., a lignosulfonate such as Reax 88B, etc.).

In some embodiments, the HSLS formulations of current disclosure have an active ingredient content of about 5 to about 40% by weight, e.g., about 5-about 40%, about 5-about 35%, about 5-about 30%, about 5-about 25%, about 5-about 20%, about 5-about 15%, about 5-about 10%, about 10-about 40%, about 10-about 35%, about 10-about 30%, about 10-about 25%, about 10 about 20%, about 10-about 15%, about 15-about 40%, about 15-about 35%, about 15-about 30%, about 15-about 25%, about 15-about 20%, about 20-about 40%, about 20-about 35%, about 20-about 30%, about 20-about 25%, about 25-about 40%, about 25-about 35%, about 25-about 30%, about 30-about 40% or about 35-about 40%. As described above in the Nanoparticles of polymer-associated active ingredient section, many ratios of strobilurin to polymer can be used.

In some embodiments the HSLS formulations of current disclosure have an active ingredient content of about 5%, about 10%, about 15%, about 20%, about 25%, about 30%, about 35% or about 40% by weight.

Methods of Making HSLS—Generally

In some embodiments, a HSLS comprising nanoparticles of polymer-associated active ingredient (optionally in aggregate form) can be made from a dispersion of polymer nanoparticles and active ingredient in a common solvent or from a dried form of the dispersion (e.g., spray dried). In some embodiments, a HSLS formulation comprising nanoparticles of polymer-associated active ingredients (optionally in aggregate form) can be made from a milled solid comprising polymer nanoparticles of active ingredient.

Methods of Making HSLS—Milling Methods

In some embodiments, a HSLS formulation comprising nanoparticles of polymer-associated active ingredients (optionally in aggregate form) can be prepared via milling. Several exemplary methods and the resulting HSLS formulations are described below and in the Examples. In some embodiments, a solid formulation of nanoparticles of polymer-associate active ingredient (optionally in aggregate form), prepared as described in this disclosure (e.g., via milling, spray drying etc.) may be further milled in the presence of one or more formulating agents and water. In some embodiments a HSLS can be made by milling a solid formulation nanoparticles of polymer-associated active ingredients in the presence water and one more of an anti-freezing agent, (optionally more than one of) a wetter and/or dispersant, an antifoaming agent, a preservative, and a thickening agent. Further, In some embodiments, the active ingredient and polymer nanoparticles are milled together to produce comprising nanoparticles of polymer-associated active ingredients, which may then be further milled according to the processes described below.

In some embodiments, the milling process is performed in separate phases (i.e., periods of time), with the optional addition of one or more formulating agent between each milling phase. One of ordinary skill in the art can adjust the length of each phase as is appropriate for a particular instance. In some embodiments, the contents of the milling vessel are cooled between one or more of milling phases (e.g., via placement of the milling jar in an ice bath). One of ordinary skill in the art can adjust the length of cooling period as is appropriate for a particular instance.

In some embodiments, a HSLS can be made by first milling a solid formulation of nanoparticles of polymer-associated active ingredients in the presence of (optionally more than one of) a wetter and/or dispersant in one milling vessel for a certain amount of time (e.g., about 30 minutes-about 1 day), then this mixture is transferred to another milling vessel containing water and optionally one or more of an anti-freezing agent, additional wetter and/or dispersant, an anti-freezing agent, an antifoaming agent, a preservative, a thickening agent, and milling the components together. As described above in the Formulating Agents section, a wide variety of additional formulating agent(s) and various concentrations of wetting agents, dispersants, fillers and other formulating agents can be used in preparation of exemplary formulations.

In some embodiments, a HSLS formulation comprising nanoparticles of polymer-associated active ingredients (optionally in aggregate form) can be prepared via milling pre-formed polymer nanoparticles and active ingredient in the presence of one or more formulating agents and water. In some embodiments, a HSLS can be made by milling preformed polymer nanoparticles and active ingredient in the presence of water and optionally one more of an anti-freezing agent, additional wetter and/or dispersant, an anti-freezing agent, an antifoaming agent, a preservative, and a thickening agent. Again, as described above in the Formulating Agents section, a wide variety of additional formulating agent(s) and various concentrations of wetting agents, dispersants, fillers and other formulating agents can be used in preparation of exemplary formulations.

And as in the embodiment described above in which nanoparticles of polymer-associated active ingredients are milled in a two milling vessel procedure, such a procedure can be used in preparing a HSLS from pre-formed polymer nanoparticles. In some embodiments such an HSLS can be made by first milling a solid formulation nanoparticles of polymer-associated active ingredients in the presence of (optionally more than one of) a wetter and/or dispersant in one milling vessel for a certain amount of time (e.g., about 30 minutes-about 1 day), transferring the milled components to another milling vessel containing water and optionally one or more of an anti-freezing agent, additional wetter and/or dispersant, an anti-freezing agent, an antifoaming agent, a preservative and a thickening agent.

Milling methods to produce HSLS formulations as described above may include any of those referred to in any other portion of the specification including the Examples below. Any type of mill noted in any portion of the specification may also be used to prepare HSLS formulations via milling.

Methods of Making HSLS—Mixing & Drying Methods

In some embodiments, a HSLS formulation is prepared without milling, but instead by mixing the components of the formulation. These methods may also include drying the formulations to increase the solids content of the formulation so that it is suitable as a HSLS. All of these methods are described in more detail below and exemplary methods are shown in the Examples.

In some embodiments, a HSLS formulation comprising nanoparticles of polymer-associated active ingredients (optionally in aggregate form) can be made from the dispersion of polymer nanoparticles and active ingredient in a common solvent, (e.g., methanol). In some embodiments, the dispersion is added to an aqueous solution containing a wetting agent and a dispersant, an anti-freezing agent (and optionally an anti-settling agent or thickener and a preservative). The mixture is then concentrated by removing solvent, e.g., by drying, until the desired high solids formulation is attained.

In some exemplary embodiments, after the dispersion of polymer nanoparticles and active ingredient in a common solvent is mixed with a second solvent containing a wetting agent and/or dispersant and an anti-freezing agent (optionally with an anti-settling agent or thickener and a preservative), the final mixture is concentrated by removing most of the common solvent and second solvent until a final formulation with a target solids content (e.g., at least 60% solids) is obtained. In some embodiments, the method used to concentrate the solution is vacuum evaporation. In some embodiments, a second solvent containing a wetting agent and/or dispersant and an anti-freezing agent (optionally with an anti-settling agent or thickener and a preservative) are added after the mixture has already been concentrated. As described above in the Nanoparticles of polymer-associated active ingredient section, many ranges of solids content can be achieved.

In some embodiments, the dispersion of polymer nanoparticles and active ingredient in a common solvent is added to a second solvent to form a solution of nanoparticles of polymer-associated active ingredients (optionally in aggregate form). The second solvent is typically miscible with the common solvent and is usually water, but in some embodiments, the second solvent can also be a mixture of water with a third solvent, usually an alcohol, preferably methanol or ethanol. In some embodiments, the second solvent or mixture of solvents is only partially miscible with the common solvent. In some embodiments, the second solvent or mixture of solvents is not miscible with the common solvent. In some embodiments, the HSLS formulation is stable after 1-2 months of continuous temperature cycling between −5° C. and 45° C. showing no visible signs of phase separation, remains flowable, and can easily be dispersed in water at the use rate.

In some embodiments, a HSLS is made by reconstituting the dried dispersion (e.g., freeze dried) of nanoparticles of polymer-associated active ingredients in water to obtain a formulation with a target solids content (e.g., at least 60% solids) is obtained and then adding an anti-freezing agent (and optionally a thickening agent and a preservative) to the final mixture. In some embodiments, a HSLS is made by reconstituting the milled (e.g., ball-milled) solid of nanoparticles of polymer-associated active ingredients in water to obtain a formulation with a target solids content (e.g., at least 60% solids) is obtained and then adding an anti-freezing agent (and optionally at least one thickening agent (e.g., fumed silica and/or xanthan gum), an antifoaming agent and a preservative) to the final mixture. In some embodiments, the HSLS is made by homogenizing all the components together. In some embodiments the HSLS is made by milling all the components together.

In some embodiments, a HSLS is made by mixing the dried dispersion (e.g., spray dried) with a wetting agent, preferably a surfactant such as sodium dodecylbenzene sulfonate, a solvent, preferably but not limited to water, and/or a dispersant, preferably, but not limited to a lignosulfonate such as Reax 88B, and an anti-freezing agent, preferably but not limited to ethylene glycol, in a high sheer mixer until a stable HSLS is obtained. In some embodiments a wetting agent, preferably a surfactant such as sodium dodecylbenzene sulfonate, a solvent, preferably but not limited to water, and a dispersant, preferably, but not limited to a lignosulfonate such as Reax 88B are included. In some embodiments, a preservative, preferably propionic acid and an anti-settling agent or thickener, preferably but not limited to fumed silica and/or a water dispersible agent like xanthan gum are also included.

Use of Low Melting Point Actives in HSLS Formulations

In some embodiments, the current disclosure provides methods of producing HSLS formulations comprising low melting-point actives. In some embodiments, the active has a melting point of less than about 100° C., less than about 90° C., less than about 80° C., less than about 70° C., less than about 60° C., less than about 50° C. or less than about 40° C. The preparation of traditional suspension concentrates of low melting-point actives is a non-trivial process. As discussed previously, typical suspension concentrate formulation involves milling the active ingredient to generate particles of about 1 to about 10 microns followed by dispersion of these particles in an aqueous phase in presence of surfactants. The use of standard granulation equipment melts low-melting point actives, complicating or precluding the size reduction process. It is thus useful that HSLS formulations of low-melting point actives may be prepared according to the current disclosure. It is also surprising that, in some embodiments, HSLS formulations can be prepared according to the present disclosure via milling of the active ingredient in the presence of pre-formed polymer nanoparticles. In some embodiments, the active ingredient of HSLS formulations of the current disclosure is picoxystrobin, pyraclostrobin, orysastrobin, metominostrobin or trifloxystrobin.

Efficacy and Application

General Applications and Efficacy

As noted previously and in the Examples, in some embodiments, the disclosure provides formulations of strobilurin compounds that have either improved curative, preventative, translocation and/or systemic fungicidal properties. In some embodiments, the strobilurin formulations of the present disclosure demonstrate improved preventative activity compared to commercial formulations of the same active ingredient, which suggests that they may be applied at lower effective rates in preventative applications. In some embodiments, the strobilurin formulations of the present disclosure demonstrate enhanced curative properties compared to commercial formulations of the same active ingredient, which suggests that they may be applied at lower effective rates in curative applications. Without wishing to be limited by any theory, it is thought that the enhanced curative properties are due to increased foliar penetration or translocation of strobilurins formulated according to the present disclosure compared to strobilurins of commercially available formulations. In some embodiments, the strobilurin formulations of the current disclosure can be applied at lower effective rates than commercial formulations for the control of fungal plant disease. In some embodiments, the strobilurin is azoxystrobin.

In general, different strobilurins are typically applied at different effective rates between 10-400 gram of active ingredient (e.g. strobilurin) per hectare depending on the efficacy of the strobilurin (e.g., absolute potency of the active and retention at the site of activity), as well as conditions related to the crop being treated, leaf type, environmental conditions, the species infesting the crop, infestation levels, and other factors. As discussed above, improvements in the formulation according to the current disclosure, such as increased UV stability, physical retention at the site of action, residual activity, systemic absorption, or enhanced curative or preventative activity can reduce the user rates. Some embodiments demonstrate improvements over typical commercial formulation, which suggests that lower rates of effective application could be used. In some embodiments, rates may range from between about 0.1 and about 400 g/hectare, preferably between about 0.1 and about 200 g/hectare, more preferably between about 0.1 and about 100 g/hectare, more preferably between about 0.1 and about 10 g/hectare or more preferably between about 0.1 and about 1 g/hectare. In some embodiments, rates may range from between about 1 g and about 400 g/hectare, preferably between about 1 and about 200 g/hectare, more preferably between about 1 and about 100 g/hectare, or more preferably between about 1 and about 10 g/hectare. In some embodiments, rates may be any of the rates or ranges of rates noted in any other portion of the specification.

General Application & Comparison to Current Commercial Formulations

In some embodiments, the disclosure provides methods of using formulations of nanoparticles of polymer-associated strobilurins. In some embodiments, the formulations are used to inoculate a target area of a plant. In some embodiments, the formulations are used to inoculate a part or several parts of the plant, e.g., the leaves, stem, roots, flowers, bark, buds, shoots, and/or sprouts.

In some embodiments, a formulation comprising nanoparticles of polymer-associated active ingredients and other formulating agents is added to water (e.g., in a spray tank) to make a dispersion that is about 10 to about 2,000 ppm in active ingredient. In some embodiments, the dispersion is about 10 to about 1,000 ppm, about 10 to about 500 ppm, about 10 to about 300 ppm, about 10 to about 200 ppm, about 10 to about 100 ppm, about 10 to about 50 ppm, about 10 to about 20 ppm, about 20 to about 2,000 ppm, about 20 to about 1,000 ppm, about 20 to about 500 ppm, about 20 to about 300 ppm, about 20 to about 200 ppm, about 20 to about 100 ppm, about 20 to about 50 ppm, about 50 to about 2,000 ppm, about 50 to about 1,000 ppm, about 50 to about 500 ppm, about 50 to about 300 ppm, about 50 to about 200 ppm, about 50 to about 100 ppm, about 100 to about 2,000 ppm, about 100 to about 1,000 ppm, about 100 to about 500 ppm, about 100 to about 300 ppm, about 100 to about 200 ppm, about 200 to about 2,000 ppm, about 200 to about 1,000 ppm, about 200 to about 500 ppm, about 200 to about 300 ppm, about 300 to about 2,000 ppm, about 300 to about 1,000 ppm, about 300 to about 500 ppm, about 500 to about 2,000 ppm, about 500 to about 1,000 ppm, about 1000 to about 2,000 ppm.

As used in the specification, inoculation of a plant with a formulation of the current disclosure may, in some embodiments, refer to inoculation of a plant with a dispersion (e.g., in water or an aqueous medium optionally further comprising other additive such as adjuvants, surfactants etc.) prepared from a formulation of the present disclosure as described above. It is to be understood that the term formulation may also encompass dispersions for applications as described (e.g., inoculation of a plant). It should also be understood that methods that describe the use of strobilurin formulations of the present disclosure e.g., "use of formulations of the present disclosure to inoculate a plant," "use of the formulations of the present disclosure to control fungal diseases" and the like, encompass the preparation of a dispersion of the active ingredient in water or an aqueous medium (optionally further comprising other additives such as adjuvants, surfactants etc.) for the purpose of inoculating a plant.

In some embodiments, a dispersion is produced and used to inoculate a plant with active ingredient at less than about 75% of a use rate listed on a label of a currently available commercial product of the same active ingredient. In some embodiments, a dispersion is produced to inoculate a plant with active ingredient at less than about 60% of a use rate listed on the label of a currently available commercial product of the same active ingredient. In some embodiments, a dispersion is produced to inoculate a plant with active ingredient at less than about 50% of a use rate listed on the label of a currently available commercial product of the same active ingredient. In some embodiments, a dispersion is produced to inoculate a plant with active ingredient at less than 40% of a use rate listed on the label of a currently available commercial product of the same active ingredient. In some embodiments, a dispersion is produced to inoculate a plant with active ingredient at less than 30% of a use rate listed on the label of a currently available commercial product of the same active ingredient. In some embodiments, a dispersion is produced to inoculate a plant with active ingredient at less than 20% of a use rate listed on the label of a currently available commercial product of the same active ingredient. In some embodiments, a dispersion is produced to inoculate a plant with active ingredient at less than 10% of a use rate listed on the labels of a currently available commercial product of the same active ingredient. In some embodiments, a dispersion is produced to inoculate a plant with active ingredient at less than 5% of the use rate listed on a label of a currently available commercial product of the same active ingredient. In some embodiments, the strobilurin formulations of the present disclosure are used to inoculate a plant at an active ingredient use rate that is about 75%, about 60%, about 50%, about 40%, about 30%, about 20% or about 10% of a use rate listed on the labels of currently available fungicide products. Fungicide labels can be referenced from commercial suppliers and are readily accessible and available.

As described in more detail below, labels of commercially available formulations often provide ranges of active ingredient use rates to control fungal disease. In some embodiments, formulations of the current disclosure may be used to control fungal disease at a range of active ingredient dose rates whose high and low values are about 75%, about 60%, about 50%, about 40%, about 30%, about 20% or about 10% of the high and low dose rates of a range listed on the label of a commercially available product of the same active ingredient. In some embodiments, the high and low dose rates of a formulation of the current disclosure are both lower than the high and low dose rate by the same percentage.

In preferred embodiments, the formulations of the current disclosure may be used to control fungal disease at an active ingredient use rate that is lower than the minimum rate of a range of rates listed on the label of a commercially available product. In some embodiments, a formulations of the current disclosure may be used to control fungal disease at an active ingredient use rate that is less than about 75%, less than about 60%, less than about 50%, less than about 40%, less than about 30%, less than about 20% or less than about 10% of the minimum use rate of a range of rates listed on the label of a commercially available product.

Low Concentration Application

In some cases, a strobilurin formulation is applied to the plant at a concentration below the strobilurin's solubility limit in water. Although the active ingredient is soluble in water at these low concentrations, the strobilurin's activity is still affected by the way it is formulated. This is surprising as it demonstrates that the strobilurin is still associated with the polymer particle even when applied below its solubility limit. At concentrations below the solubility limits it is expected that the strobilurins would behave the same, or at least in a very similar fashion, regardless of the formulations, especially with respect to biological functions described above. This is because the strobilurins are still hydrophobic and thus, thought to still have low soil mobility, lack systemic effects and display the traits of traditional strobilurin and traditional strobilurin formulations.

In some embodiments, however, a formulation with nanoparticles or aggregates of nanoparticles of polymer associated strobilurin compound is shown to be more active (e.g., have systemic or curative effects) than commercially available suspension concentrates of a strobilurin when applied at a use rate below the solubility limit. Comparative example is described below in the Examples section. In some embodiments, the strobilurin is azoxystrobin. In some embodiments, the polymer nanoparticles associated with the strobilurin compound is made from a copolymer of methacrylic acid and ethyl acrylate at a mole ratio of ~90:10 (MAA:EA) though other ratios, as described above, are applicable. In some embodiments, the formulation includes a wetter, dispersant and filler. In some embodiments, the formulation was applied with a foliar retention aid to enhance sticking to the plant surface. In some embodiments, the foliar retention aid is partially hydrolyzed poly(vinyl alcohol) such as the products marketed under the Gohsenol brand.

Improved Translocation of Active

In some embodiments, the disclosure provides formulations of strobilurin compounds that have improved translocation properties e.g., as compared to a commercially available concentrate of the same active ingredient (e.g., Amistar®). Though the specifics of a comparison test are described in an Example below, generally, the exemplary procedure is as follows: The basal portion of a corn leaf was inoculated with a dispersion of strobilurin compound prepared from a commercial strobilurin formulation or a formulation of the present disclosure. In an exemplary embodiment azoxystrobin in a HSLS formulation according to this disclosure was compared to Amistar®. The dispersions were prepared in 0.25 wt % induce solution at a specific strobilurin concentration (e.g., 200 or 500 ppm). After inoculation of the leaf the corn plant was placed in a growing chamber. Translocation was evaluated by harvesting the leaf 24 hours after application and cutting off the tip of the leaf (untreated part of the leaf) from its apical section. Evaluation and harvesting were performed 3 or 7 days after application. One of ordinary skill in the art can adjust the evaluation time (as well as other parameters including concentration and dilution) as is appropriate for a particular instance.

The amount of compound in the tip of the leaf was evaluated (e.g., via extraction with organic solvent and HPLC quantification). The amount of strobilurin in the tip (removed section) of the leaf is expressed as a percentage of the dry mass of the tip of the leaf. Leaves that had been inoculated with formulations prepared according to the present disclosure showed increased translocation compared to leaves inoculated with commercial formulations. In some embodiments, there was a larger amount of strobilurin compound in the tips of leaves inoculated with formulations of the present disclosure than leaves inoculated with commercial formulations. In some embodiments, the tips of leaves inoculated with formulations of the present disclosure contained more strobilurin (expressed as a percentage of the dry weight of cut, apical sections of the leaves) than leaves inoculated with commercially available strobilurin formulations.

Without wishing to be limited by any theory, in some embodiments, the enhanced translocation properties of strobilurins of the present disclosure are thought to be due in part to enhanced foliar penetration. Without wishing to be limited by any theory, the enhanced translocation properties of the present disclosure may also be due in part to improved adhesion specificity, smaller particle size and improved water dispersibility. As discussed above, many strobilurins suffer from weak curative activity because they are non-systemic (e.g., they do not translocate). Again without wishing to be limited, the improved curative activity of formulations of the present disclosure may be due to improved translocation properties. As discussed above, enhanced curative activity provides a number of advantages, such as the potential for application at reduced effective active ingredient use rates.

Rainfast Applications

In some embodiments, a strobilurin formulation is applied and demonstrates rainfast properties, in that the active ingredient (e.g., strobilurin) does not dissipate with rain, in comparison with commercially available formulations of the same active. Though the specifics of a comparison test are described in an Example below, generally, the exemplary procedure is as follows: a 1.7 cm cut disk of a cole plant leaf (cabbage at ca. 7 leaf stage) was inoculated with a strobilurin by dipping the disk into a dispersion containing either a commercial strobilurin formulation or a strobilurin formulation according to the disclosure at a specific use rate (e.g., 50 ppm strobilurin) along with 0.5% Spray Adjuvant (Supercharge) for 5 seconds and was allowed to air dry for 1-2 hours. In an exemplary embodiment, the formulation includes azoxystrobin in a HSLS formulation according to this disclosure. Rainfastness was evaluated by dipping inoculated leaf disks (as described in the Example below) into deionized water for 5 seconds, allowing the leaf to air dry for 2 hours. The amount of strobilurin that remains on the leaf is quantified. The amount of strobilurin that remains on the leaf is expressed as percentage biomass of the dried leaf. In some embodiments, strobilurin remains on the leaf after dipping into deionized water (rain treatment). In some embodiments, the formulations of the current disclosure show comparable or improved rainfast properties compared to leaves inoculated with commercial formulations.

Hard Water/Fertilizer Applications

As described below, most traditional formulations produce solid particles (floc) or a precipitate when mixed in with high salt, hard water or fertilizer solutions. Surprisingly, a dispersed solid formulation of a strobilurin (e.g., azoxystrobin) of the current disclosure was stable (e.g., components, azoxystrobin and the salt, remained disperse, i.e., no visible sedimentation or floc) when mixed with a concentrated/high salt solution (e.g., hard water, buffer, concentrated fertilizer formulation) for at least 3 hours. This was true even for waters with ionic strength as high as 8000 ppm $Mg^{2+}$ (a.k.a. CIPAC "G" hard water). It is important to note that for such a mixture to be useful for the end user, the mixture should remain stable (i.e., no formation of sediments and/or flocs) within at least about 30-40 minutes—which is typically the time it takes for the mixture to be applied to the plant. It is surprising that the formulations of the present disclosure are stable in such high-salt conditions. Because the polymers that are used in the nanoparticles of the present disclosure are negatively charged, a practitioner of the art would expect the formulations of the present disclosure to flocculate when mixed with such a high amount of divalent salt. Without being limited by theory, it is believed that the increased stability of the formulations of the present disclosure arises from the use of nanoparticulate polymers as the delivery system and that if standard non-nanoparticle polymers were used then flocculation would occur Traditional solid or liquid formulations are not stable under conditions of high ionic (i.e., a high salt solution) strength. Sources of increased ionic strength can include, for example, mineral ions that are present in the water that a formulation is dispersed in. For example, in many cases the water that is available to a farmer is taken from a high-salt ("hard water") source such as a well or aquifer. Water that a grower uses can be variably hard and is normally measured as $Ca^{2+}$ equivalents. Ranges of water salinity can be from ~0 ppm $Ca^{2+}$ equivalent (deionized water) to 8000 ppm $Ca^{2+}$ or more.

Other sources of increased ionic strength can include, for example, other chemicals or materials that dispersed in the spray tank water before or after the addition of the fungicide formulation. Examples of this include mineral additives such as micronutrients (which can include e.g., B, Cu, Mn, Fe, Cl, Mo, Zn, S) or traditional N—P—K fertilizers where the nitrogen, phosphorus, or potassium source is in an ionic form as well as other agro-chemicals (e.g., pesticides, herbicides, etc.). In some embodiments, the fertilizer can be 10-34-0 (N—P—K), optionally including one or more of sulfur, boron and another micronutrient. In some cases, the nitrogen source is in the form of urea or an agriculturally acceptable urea salt. The fertilizer can include e.g., ammonium phosphate or ammonium thiosulphate.

In some embodiments described below in the Examples, the formulations of the current disclosure were mixed with a concentrated/high salt solution. Though the specifics of the hard test are described in Examples below, generally, the exemplary procedure is as follows: Formulations described herein were mixed with different hard water standards, each with a different degree of hardness (e.g., CIPAC H standard water (in the example below: 634 ppm hardness, pH 6.0-7.0, $Ca^{2+}:Mg^{2+}=2.5:1$), CIPAC J standard water (6.34 ppm hardness, pH 6.0-7.0, $Ca^{2+}:Mg^{2+}=2.5:1$) and CIPAC G standard water (8000 ppm hardness, pH 6.0-7.0, $Mg^{2+}$)) at an active ingredient concentration of 200 ppm. In some embodiments, the formulations dispersed well and were stable for at least an hour, with no signs of the formation of flocs or sediments.

In some cases, the formulations of the present disclosure can be applied simultaneously with a high-salt solution or suspension such as a micronutrient solution, a fertilizer, pesticide, herbicide solution, or suspension (e.g., in furrow application). The ability to mix and apply strobilurins with other agricultural ingredients such as liquid fertilizers is very useful to growers, as it reduces the number of required trips across crop fields and the expenditure of resources for application. In some cases, the formulations of the present disclosure may be mixed with liquid fertilizers of high ionic strength. In some cases the fertilizer is a 10-34-0 fertilizer, optionally including one or more of sulfur, boron and another micronutrient. In some cases, the nitrogen source is in the form of urea or an agriculturally acceptable urea salt. In some embodiments, the liquid fertilizer comprises a glyphosate or an agriculturally acceptable salt of glyphosate (e.g., ammonium, isopropylamine, dimethylamine or potassium salt). In some embodiments, the liquid fertilizer may be in the form of a solution or a suspension. In some embodiments, formulations of the present disclosure are stable when mixed with liquid fertilizers of increased or high ionic strength (e.g., at any of the ionic strengths described below). In some embodiments, when mixed with liquid fertilizers formulations of the current disclosure show no signs of sedimentation or flocculation. In some embodiments, the strobilurin is azoxystrobin.

Other potential additives that might be added into a spray tank that are charged and can decrease the stability of an agrochemical formulation include charged surfactants or polymers, inert ingredients such as urea, or other similar ingredients.

In some embodiments, the present disclosure provides compositions of a formulation of nanoparticles of polymer-associated active ingredients that are redispersible in solutions with high ionic strength. In some embodiments, the present disclosure also provides compositions of a formulation of nanoparticles of polymer-associated active ingredients that can be redispersed in water and then have a high salt solution or solid salt added and maintain their stability. In some embodiments, the formulations of the present disclosure are stable when dispersed in or dispersed in water and then mixed with solutions with ionic strength corresponding to $Ca^{2+}$ equivalents of about 0 to about 1 ppm, about 0 to about 10 ppm, about 0 to about 100 ppm, about 0 to about 342 ppm, about 0 to about 500 ppm, about 0 to about 1000 ppm, about 0 to about 5000 ppm, about 0 to about 8000 ppm, about 0 to about 10000 ppm, about 1 to about 10 ppm, about 1 to about 100 ppm, about 1 to about 342 ppm, about 1 to about 500 ppm, about 1 to about 1000 ppm, about 1 to about 5000 ppm, about 1 to about 8000 ppm, about 1 to about 10000 ppm, about 10 to about 100 ppm, about 10 to about 342 ppm, about 10 to about 500 ppm, about 10 to about 1000 ppm, about 10 to about 5000 ppm, about 10 to about 8000 ppm, about 10 to about 10000 ppm, about 100 to about 342 ppm, about 100 to about 500 ppm, about 100 to about 1000 ppm, about 100 to about 5000 ppm, about 100 to about 8000 ppm, about 100 to about 10000 ppm, about 342 to about 500 ppm, about 342 to about 1000 ppm, about 342 to about 5000 ppm, about 342 to about 8000 ppm, about 342 to about 10000 ppm, about 500 to about 1000 ppm, about 500 to about 5000 ppm, about 500 to about 8000 ppm, about 500 to about 10000 ppm, about 1000 to about 5000 ppm, about 1000 to about 8000 ppm, about 1000 to about 10000 ppm, about 5000 to about 8000 ppm, about 5000 to about 10000 ppm, about 8000 to about 10000 ppm.

Protective Use

In some embodiments, the present disclosure provides formulations of strobilurins that may be used as protective fungicides (also referred to as protectants). In general, protective fungicides are used to prevent the establishment of a pathogenic fungal infection in a plant or a portion of a plant. It is therefore desirable for the protectant fungicide to be present on the plant or portion of the plant prior to its contact with the pathogen. When used as protective fungicides, the formulations of the present disclosure may be used to make dispersions of active ingredients as described above, at active ingredient concentrations that correspond to any of the values or ranges above in the Efficacy and Application or in other parts of this disclosure. In some embodiments, a dispersion is prepared and used to inoculate a plant with a protective fungicide at less than about 75% of a use rate listed on the label of a currently available commercial protective fungicide product of the same active ingredient. In some embodiments, a dispersion is prepared and used to inoculate a plant with a protective fungicide at less than about 60% of a use rate listed on the labels of a currently available commercial protective fungicide product of the same active ingredient. In some embodiments, a dispersion is prepared and used to inoculate a plant with a protective fungicide at less than about 50% of a use rate listed on the label of currently available commercial protective fungicide product. In some embodiments, a dispersion is prepared and used to inoculate a plant with a protective fungicide at less than about 40% of a use rate listed on the labels of currently available commercial protective fungicide products of the same active ingredient. In some embodiments, a dispersion is prepared and used to inoculate a plant with a protective fungicide at less than about 30% of a use rate listed on the label of currently available commercial protective fungicide products of the same active ingredient. In some embodiments, a dispersion is prepared and used to inoculate a plant with a protective fungicide at less than 20% of a use rate listed on a label of a currently available commercial protective fungicide product of the same active ingredient. In some embodiments, a dispersion is prepared and used to inoculate a plant with a protective fungicide at less than about 10% of a use rate listed on the label of a currently available commercial protective fungicide product of the same active ingredient. In some embodiments, a dispersion is prepared and used to inoculate a plant with a protective fungicide at less than 5% of a use rate listed on the label of currently available commercial protective fungicide products of the same active ingredient. In some embodiments, a strobilurin formulation of the current disclosure is used as a protective fungicide at an active ingredient use rate that is about 75%, about 60%, about 50%, about 40%, about 30%, about 20% or about 10% of the use rate listed on the label of a currently available protective fungicide product.

Labels of commercially available formulations often provide ranges of active ingredient use rates to control fungal disease. When used as protectant fungicides as described above, a formulation of the current disclosure may be used to inoculate plants at an active ingredient use rate that is less than about 75%, less than about 60%, less than about 50%, less than about 40%, less than about 30%, less than about 20% or less than about 10% of the minimum use rate of a range of use rates listed on the label of a commercially available product.

Curative Use

In some embodiments, the present disclosure provides formulations of strobilurins that have curative activity, and that may thus be used as curative fungicides. In general, fungicides with curative activity may be used to control established fungal infection in plants that are not yet showing visible symptoms of the infection. As such, fungicides with curative activity can be applied to plants after the establishment of infection. When used as curative fungicides, the formulations of the present disclosure may be used to make dispersions of active ingredients as described above, at active ingredient concentrations that correspond to any of the values or ranges above in the Efficacy and Application or in other parts of this disclosure. In some embodiments, a dispersion is prepared and used to inoculate a plant with a curative fungicide at less than about 75% of a use rate listed on the label of currently available commercial fungicide products of the same active ingredient. In some embodiments, a dispersion is prepared and used to inoculate a plant with a curative fungicide at less than about 60% of a use rate listed on the label of currently available commercial fungicide products of the same active ingredient. In some embodiments, a dispersion is prepared and used to inoculate a plant with a curative fungicide at less than about 50% of a use rate listed on the label of currently available commercial fungicide products of the same active ingredient. In some embodiments, a dispersion is prepared and used to inoculate a plant with a curative fungicide at less than about 40% of a use rate listed on the label of currently available commercial fungicide products of the same active ingredient. In some embodiments, a dispersion is prepared and used to inoculate a plant with a curative fungicide at less than about 30% of a use rate listed on the label of currently available commercial fungicide products of the same active ingredient. In some embodiments, a dispersion is prepared and used to inoculate a plant with a curative fungicide at less than about 20% of a use rate listed on the label of currently available commercial fungicide products of the same active ingredient. In some embodiments, a dispersion is prepared and used to inoculate a plant with a curative fungicide at less than about 10% of a use rate listed on the label of currently available commercial fungicide products of the same active ingredient.

Labels of commercially available formulations often provide ranges of active ingredient use rates to control fungal disease. When used as curative fungicides as described above, a formulations of the current disclosure may be used to inoculate plants at an active ingredient use rate that is less than about 75%, less than about 60%, less than about 50%, less than about 40%, less than about 30%, less than about 20% or less than about 10% of the minimum use rate of a range of use rates listed on a commercially available product's label.

Dual Activity (Protective & Curative Uses)/Plant Health Applications

In some embodiments, the present disclosure provides formulations of strobilurins that have both protective and curative activity. These formulations can be used as protective fungicides, curative fungicides, or as fungicides in both protective and curative applications. These formulations can be used at concentrations and use rates that correspond to any of the values or ranges of values noted above or in other portions of the Efficacy and Application Section.

In some embodiments, application of formulations of the present disclosure to plants (e.g., crop plants) of the present disclosure results in a yield increase (e.g., increased crop yield). In some embodiments, there is a yield increase compared to untreated crops. In some embodiments, there is an increase compared to crops that have been treated with a commercial formulation of the same active ingredient. In some embodiments, there is yield increase of about 2 to about 100%, e.g., 2-3%, 2-5%, 2-10%, 2-30%, 2-50%, 2-100%, 5-7%, 5-10%, 5-20%, 5-30%, 5-40%, 5-50%, 5-60%, 5-70%, 5-80%, 5-90%, 5-100%, 10-20%, 10-30%, 10-40%, 10-50%, 10-60%, 10-70%, 10-80%, 10-90%, 20-40%, 20-60%, 20-80%, 20-100%, 30-50%, 30-60%, 30-80%, 30-100%, 40-60%, 40-80%, 40-100%, 50-80%, 50-100%, 60-80%, 60-100%, 70-90%, 70-100% or 80-100%

In some embodiments, the use of the strobilurin formulations of the present disclosure results in a yield increase of about 2%, about 3%, about 4%, about 5%, about 6%, about 7%, about 10%, about 20%, about 30%, about 40%, about 50%, about 60%, about 70%, about 80%, about 90% or about 100%. In some embodiments, there is yield increase of greater than about 2%, greater than about 5%, greater than about 10%, greater than about 20%, greater than about 30%, greater than about 40%, greater than about 50%, greater than about 60%, greater than about 70%, greater than about 80%, greater than about 90% or greater than about 100%. In some embodiments, the use of the strobilurin formulations of the present disclosure in plant health applications results in a yield increase of greater than about 10%, greater than about 20%, greater than about 30%, about 40%, about 50%, about 60%, about 70%, about 80%, about 90% or about 100%. In some embodiments, there is an increase in yield of greater than about 10%, greater than about 20%, greater than about 30%, greater than about 40%, greater than about 50%, greater than about 60%, greater than about 70%, greater than about 80%, greater than about 90% or greater than about 100%. Yield increases may be relative to untreated control plants (e.g., plants that have not been treated with formulations of the present disclosure), or plants treated with currently available commercial products.

In some embodiments, inoculation of plants with formulations of the present disclosure provides an increased crop yield as described above, at an active ingredient use rates that are lower than the use rates listed on commercially available products of the same active ingredient. In some embodiments, the increased yield can correspond to any of the values or ranges of values noted above. In some embodiments, the increased yield is observed at an active ingredient use rate that is less than about 75%, less than 60%, less than 50%, less than 40%, less than 30%, less than 20% or less than 10% of a rate listed on the label of commercially available fungicide product of the same active ingredient. In some embodiments, the increased yield is observed at an active ingredient use rate that is about 75%, about 60%, about 50%, about 40%, about 30%, about 20% or about 10% of a rate listed on a label of a commercially available fungicide product of the same active ingredient. Labels of commercially available formulations often provide ranges of active ingredient use rates to inoculate plants. In some embodiments, inoculation of plants with a formulation of the present disclosure provides an increased crop yield at an active ingredient use rate that is lower than the minimum use rate of a range of use rates listed on the label of a commercially available product. In some embodiments inoculation of plants with a formulation of the present disclosure provides an increased crop yield at a use rate that is less than about 75%, less than about 60%, less than about 50%, less than about 40%, less than about 30%, less than about 20% or less than about 10% of the minimum use rate of a range of use rates listed on the label of a commercially available product.

Without wishing to be limited by any theory, in some embodiments, it is thought that increased yield is due enhanced plant health of plants treated with formulations of the present disclosure. As used herein, plant health refers to the overall condition of the plant, including its size, sturdiness, optimum maturity, consistency in growth pattern and reproductive activity. As mentioned above, optimizing and enhancing such factors is a goal of plant breeders. As used herein, increased or enhanced plant health can also refer to increased yield of one sample or set of crops (e.g., a crop field treated with fungicide) compared to another sample or set of the same crops (e.g., an untreated crop field).

The enhancement of plant health by applications of strobilurin fungicides is thought to be due to a number of factors, as discussed above. These include combating hidden and undiagnosed diseases, as well as and the triggering of plant growth regulators (the strobilurin greening effect, see D. W. Bartlett, J. M. Clough, J. R. Godwin, A. A. Hall, M. Hamer, and B. Parr-Dobrzanski. *Pest Manag. Sci.* 2002, 58. 649). In some embodiments, the strobilurin formulations of the present disclosure can be used to enhance plant health at an active ingredient use rate that is lower than the rate listed on the labels of currently available commercial curative fungicide products of the same active ingredient. In some embodiments, a strobilurin formulations of the present disclosure is used to inoculate a plant at an active ingredient use rate that is less than about 75%, less than about 60%, less than about 50%, less than about 40%, less than about 30%, less than about 20% or less than about 10% of a use rate listed on the label of a currently available fungicide product. In some embodiment, a strobilurin formulation of the present disclosure is used to inoculate a plant at an active ingredient use rate that is about 75%, about 60%, about 50%, about 40%, about 30%, about 20% or about 10% of a use rate listed on the label of a currently available fungicide product. Labels of commercially available formulations often provide ranges of active ingredient use rates to inoculate plants. In some embodiments, a formulation of the current disclosure is used to inoculate plants at an active ingredient use rate that is lower than the minimum use rate of a range of use rates listed on the label of a commercially available product. In some embodiments a formulation of the current disclosure is used to inoculate plants at a use rate that is less than about 75%, less than about 60%, less than about 50%, less than about 40%, less than about 30%, less than about 20% or less than about 10% of the minimum use rate of a range of use rates listed on the label of a commercially available product Without wishing to be limited by any theory, in some embodiments, it is thought that the formulations of the present disclosure can be used to enhance plant health at an active ingredient use rate that is lower than the rate listed on commercially available products of the same active ingredient due to their enhanced curative and preventative properties. Without wishing to be limited by any theory, it is though that in some embodiments, the enhanced curative properties are due to enhanced foliar penetration and/or translocation. Without wishing to be limited by any theory it is thought that in some embodiments, the formulations of the present disclosure are more effective at combating hidden disease because of their enhanced residual activity, which increases the window of opportunity for successful application timing.

Direct Soil & Seed Applications

In some embodiments, formulations of the current disclosure may be used to control fungal disease of plants (including seeds) by application to soil (inoculation of soil). The formulations of the current disclosure may be used to control fungal disease via application to the soil in which a plant is to be planted prior to planting (i.e., as pre-plant incorporated application). In some embodiments, the formulations of the present disclosure are used to control fungal disease via inoculation of the seed and soil at the time of seed planting (e.g., via an in-furrow application or T-banded application). The formulations of the current disclosure may also be applied to soil after planting but prior to emergence of the plant (i.e., as a pre-emergence application). In some embodiments, soil is inoculated with a formulation of the current disclosure via an aerosol spray or pouring.

In some embodiments, the strobilurin formulations of the current disclosure may be used to control fungal diseases in the aforementioned applications at an active ingredient use rate that is lower than the use rate listed on the labels of commercially available formulations of the same active ingredient, as described above. In some embodiments, a formulation of the present disclosure is used to control fungal disease at an active ingredient use rate that is less than about 75%, less than about 60%, less than about 50%, less than about 40%, less than about 30%, less than about 20% or less than about 10% of a use rate listed on the labels of currently available commercial strobilurin products of the same active ingredient. In cases in which labels of commercially available formulations provide ranges of active ingredient use rates to control fungal disease, in some embodiments, a formulations of the current disclosure are used to control fungal disease at an active ingredient use rate that is lower than the minimum use rate of the range of use rates listed on the commercially available product's label. In some embodiments a formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available product.

In some embodiments, the strobilurin formulations of the current disclosure can be used to control fungal disease when applied to seeds. In some embodiments, the formulations of the current disclosure are used to control fungal disease when applied to seeds at an active ingredient use rate that is less than the use rate of commercially available formulations of the same active ingredient. In some embodiments, a formulation of the present disclosure is used to control fungal diseases when applied to seeds at an active ingredient use rate that is less than about 75%, less than about 60%, less than about 50%, less than about 40%, less than about 30%, less than about 20% or less than about 10%, of a use rate listed on the label of a currently available commercial strobilurin product of the same active ingredient. In some embodiments, a formulation of the present disclosure are used to control fungal disease when applied to seeds at an active ingredient use rate that is about 75%, about 60%, about 50%, about 40%, about 30%, about 20% or about 10%, of a rate listed on the label of a currently available strobilurin product of the same active ingredient. In some embodiments, commercially available products provide ranges of active ingredient use rates to control fungal disease when applied to seeds. In some embodiments, the formulations of the current disclosure are used to control fungal disease when applied to seeds at an active ingredient use rate that is lower than the minimum use rate of a range of use rates listed on a commercially available product's label. In some embodiments a formulation of the current disclosure is used to control fungal disease when applied to seeds at a use rate that is less than about 75%, less than about 60%, less than about 50%, less than about 40%, less than about 30%, less than about 20% or less than about 10% of the minimum use rate of a range of use rates listed on the label of a commercially available product.

Increased Re-Application Interval

Due to their enhanced curative and preventative properties, in some embodiments, the formulations of the present disclosure can be applied at greater time intervals (i.e., the time between distinct inoculations) than currently available formulations of the same active ingredient. Inoculation intervals can be found on the labels of currently available commercial formulations and are readily accessible and available. In some embodiments, the formulations of the present disclosure are applied at an interval that is 1 day, 2 days, 3 days, 4 days, 5 days, 6 days, 7 days, 8 days, 9 days, 10 days, 11 days, 12 days, 13 days, 14 days or 15 days longer than commercial formulations of the same active ingredient. In some cases, commercial formulations are applied at intervals that correspond to a range of intervals (e.g., 7-14 days). In such cases, it is contemplated that the formulations of the present disclosure can be applied at a range of intervals whose shortest endpoint, longest endpoint, or both shortest and longest endpoint are longer than the corresponding endpoints of currently available commercial formulations by any of the values noted above. In some embodiments, the strobilurin formulations of the present disclosure can be applied at an intervals of 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days or 40 days. In some embodiments, the formulations of the present disclosure can be applied at a range from which the shortest and longest intervals (endpoints) are taken from any of the aforementioned values.

Specific Application (Plant & Fungi)

In some embodiments, the inoculation method is applied to individual plants or fungi, or to large groups of plants and fungi. In some embodiments, the formulation is inoculated to the target organism by means of dipping the target organism or part of the organism into the dispersion containing the formulation. In some embodiments, the formulation is inoculated to the target species (plant or fungi) by means of an aerosol spray. In some embodiments, the formulation is inoculated to the target species (plant) by spraying the dispersion directly onto the leaves, stem, bud, shoot or flowers of the plant. In some embodiments, the formulation is inoculated to the target species (plant) by pouring the dispersion directly onto the root zone of the plant. In some embodiments, the target organism (e.g., the plant on which fungus is to be controlled or the fungus is inoculated by means of dipping the plant or a part of parts of the target plant into a dispersion of active ingredients prepared as described above. Formulations of the current invention can also be applied in conjunction with irrigation systems and via water for irrigation.

The strobilurin formulations of the present disclosure can be used to control fungal disease of a variety of plants. In some embodiments, the plant is selected from the classes fabaceaae, brassicaceae, rosaceae, solanaceae, convolvulaceae, poaceae, amaranthaceae, laminaceae and apiaceae.

In some embodiments, the plant is selected from plants that are grown for turf, sod, seed (e.g., grasses grown for seed), pasture or ornamentals. In some embodiments, the plant is a crop, including but not limited to cereals (e.g., wheat, maize, including field corn and sweet corn, rice, barley, oats etc.), soybean, cole crops, tobacco, oil crops, cotton, fruits (e.g., pome fruits such as but not limited to apples and pears), vine crops (e.g., cucurbits), legume vegetables, bulb vegetables, rapeseed, potatoes, greenhouse crops, and all other crops on which strobilurins are known to control fungal disease. Lists of plants on which fungal diseases are controlled by specific commercially available strobilurin formulations can be found on their labels, which are readily accessible and available. (Examples of such products are given below).

In some embodiments, the formulations of the current disclosure are used to control fungal diseases in turf, ornamental and non-crop applications (uses). Examples of these applications can be found on the labels of currently available strobilurin formulations, such as the labels referenced in other portions of the specification. Non-limiting examples of turf, ornamental and non-crop applications in which the formulations of the present disclosure can be used include the control of fungal diseases of turf (e.g., lawns and sod) in residential areas, athletic fields, parks, and recreational areas such as golf courses. Formulations of the present disclosure may also be used to control fungal diseases of ornamentals (e.g., shrubs, ornamental trees, foliage plants etc.), including ornamentals in or around any of the aforementioned areas, as well as in greenhouses (e.g., those used for growth of ornamentals). Examples of fungi that can be controlled in turf, ornamental and non-crop applications, include those listed as fungi turf, ornamental and non-crop applications in any other portion of the specification or in any of the labels of currently available strobilurin products used to control fungi in turf, ornamental and non-crop applications (such as the those referenced in other portions of the specification).

In some embodiments, the fungus to be controlled by the formulations of the present disclosure is selected from the classes ascomycota, basidiomycota, deuteromycota, blastocladiomycota, chytridiomycota, glomeromycota and combinations thereof.

Examples of fungal diseases that can be controlled with formulations of the current disclosure include but are not limited to various blights, spots and rusts, rots, blasts and smuts and combinations thereof.

In some embodiments, the plant (e.g., crop) on which fungal disease can be controlled by formulations of the present disclosure may depend on, among other variables, the active ingredient, inclusion of other components into the formulation, and the particular application. Common commercial formulations frequently include labels and instructions describing the compatibility of actives, inclusion of additives, tank mixes with other products (e.g., surfactants) labeled fungi, instructions and restrictions for particular applications and uses as well as other information. Such labels and instructions pertinent to the formulations of the present disclosures and their application are also contemplated as part of the present disclosures. Labels are readily accessible from manufacturers' websites, or via centralized internet databases such as Greenbook (http://www.greenbook.net/) or the Crop Data Management Systems website (www.cdms.net).

In some embodiments, the strobilurin of the present disclosure is azoxystrobin, trifloxystrobin, pyraclostrobin, pyraclostrobin, or fluoxastrobin.

Specific Commercial Applications (Crop, Active, Dose, Application & Formulation)

As used herein, "a range of rates" listed on the label of a commercially available product refers to a rate range listed for the control of a pest or pests in a certain application (e.g. on a crop). For example, the labeled use rate for the control of *Puccina sorghi* on cotton by Quadris is 109-164 g/ha, which is a "range of rates."

Azoxystrobin

In various embodiments, the azoxystrobin formulations of the current disclosure may be used to control fungal diseases at active ingredient use rates that are lower than the use rates listed on the labels of commercially available azoxystrobin fungicides. In some embodiments, an azoxystrobin formulation of the current disclosure may be used to control fungal disease at a use rate that is less than about 75%, less than about 60%, less than about 50%, less than about 40%, less than about 30%, less than about 20% or less than about 10% of a use rate listed on the label of a commercially available azoxystrobin fungicide product.

Labels of commercially available azoxystrobin products often provide ranges of active ingredient use rates to control certain fungal diseases on certain plants (e.g., as shown in table 4, 109-282 g/ha for the control of aerial blight of soybean). In some embodiments, the azoxystrobin formulations of the current disclosure are used to control fungal disease at an active ingredient use rate that is lower than the minimum use rate of a range of use rates listed on the label of a commercially available azoxystrobin product. In some embodiments an azoxystrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available azoxystrobin product.

Azoxystrobin—Soybeans

Labelled use rates for the control of various fungal diseases of soybeans by Quadris® and Priori®, two commercially available azoxystrobin suspension concentrates, are provided in Table 4.

TABLE 4

Active ingredient use rates for the control of fungal diseases of soybeans by commercially available azoxystrobin products.

| Product | Target Fungi | Use Rate (g ai/ha) |
| --- | --- | --- |
| Quadris ® | Aerial blight (*Rhizoctonia solani*), Anthracnose (*Colletotrichum truncation*), *Alternaria* leaf spot (*Alternaria* spp.), Brown spot (*Septoria glycines*) Cercospora blight and leaf spot (*Cercospora kikuchii*), Frogeye leaf spot (*Cercospora sojina*), Pod and stem blight (*Diaporthe phaseolorum*), Rust (*Phakopsora* spp.) | 109-282 |
| | Soilborne diseases: Southern blight (*Sclerotium rolfsii*), Rhizoctonia solani (*Rhizoctonia solani*) | 9.7-19.3 g/1000 row meters |
| Priori ® | *Cercospora kikuchii, Phakopsora pachyrhizi, Septoria glycines* | 50 |

In some embodiments, the azoxystrobin formulations of the current disclosure are used to control fungal diseases of soybeans at an active ingredient use rate that is lower than the use rates listed on the label of commercially available azoxystrobin fungicides. In some embodiments, an azoxystrobin formulation of the current disclosure is used to control fungal diseases of soybeans at a use rate that is less than about 75% of a rate listed on the label of a commercially available azoxystrobin fungicide product. In some embodiments, an azoxystrobin formulation of the current disclosure is used to control fungal diseases of soybeans at a use rate that is less than about 60% of a rate listed on the label of a commercially available azoxystrobin fungicide product. In some embodiments, an azoxystrobin formulation of the current disclosure is used to control fungal diseases of soybeans at a use rate that is less than about 50% of a rate listed on the label of a commercially available azoxystrobin fungicide product. In some embodiments, an azoxystrobin formulation of the current disclosure is used to control fungal diseases of soybeans at a use rate that is less than about 40% of a rate listed on the label of a commercially available azoxystrobin fungicide product. In some embodiments, an azoxystrobin formulation of the current disclosure is used to control fungal diseases of soybeans at a use rate that is less than about 30% of a rate listed on the label of a commercially available azoxystrobin fungicide product. In some embodiments, an azoxystrobin formulation of the current disclosure is used to control fungal diseases of soybeans at a use rate that is less than about 20% of a rate listed on the label of a commercially available azoxystrobin fungicide product. In some embodiments, an azoxystrobin formulation of the current disclosure is used to control fungal diseases of soybeans at a use rate that is less than about 10% of a rate listed on the label of a commercially available azoxystrobin fungicide product.

In some embodiments, the azoxystrobin formulations of the current disclosure are used to control fungal disease of soybeans at an active ingredient use rate that is lower than the minimum use rate of a range of use rates listed on a commercially available product's label. In some embodiments azoxystrobin formulations of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available product.

In some embodiments, the azoxystrobin formulations of the present disclosure may be used to control fungal diseases of soybeans at an active ingredient use rate of about 82-about 212 g/ha, about 65-about 169 g/ha, about 54-about 141 g/ha, about 44-about 113 g/ha, about 33-about 85 g/ha, about 22-about 56 g/ha, or about 11-about 28 g/ha.

In some embodiments, the azoxystrobin formulations of the current disclosure may be used to control fungal diseases of soybeans at an active ingredient use rate of less than about 212 g/ha, less than about 169 g/ha, less than about 141 g/ha, less than about 113 g/ha, less than about 85 g/ha, less than about 82 g/ha, less than about 65 g/ha, less than about 56 g/ha, less than about 54 g/ha, less than about 44 g/ha, less than about 32 g/ha, less than about 28 g/ha, less than about 22 g/ha, or less than about 11 g/ha. In some embodiments, the azoxystrobin formulations of the current disclosure can be used to control fungal diseases of soybeans at an active ingredient use rates of less than about 50 g/ha, less than about 37.5 g/ha, less than about 30 g/ha, less than about 25 g/ha, less than about 20 g/ha, about 15 g/ha or less than about 10 g/ha.

Non-limiting examples of fungal diseases of soybeans that can be controlled with formulations of the present disclosure are Aerial blight (*Rhizoctonia solani*), Anthracnose (*Colletotrichum truncatum*), Alternaria leaf spot (*Alternaria* spp.), Brown spot (*Septoria glycines*), *Cercospora* blight and leaf spot (*Cercospora kikuchii*), Frogeye leaf spot (*Cercospora sojina*), Pod and stem blight (*Diaporthe phaseolorum*) and Rust (*Phakopsora* spp.).

In some embodiments, the azoxystrobin formulations of the current disclosure may be used to control soilborne fungal diseases of soybeans at an active ingredient use rate that is lower than the use rate listed on the label of commercially available azoxystrobin fungicides. In some embodiments, an azoxystrobin formulation of the current disclosure is used to control soilborne fungal diseases of soybeans at a use rate that is about 75%, about 60%, about 50%, about 40%, about 30%, about 20% or about 10% of a use rate listed on the label of commercially available azoxystrobin fungicides.

In some embodiments, the azoxystrobin formulations of the current disclosure may be used to control soilborne fungal diseases of soybeans at an active ingredient use rate that is lower than the minimum use rate of a range of use rates listed on the commercially available product's label. In some embodiments an azoxystrobin formulation of the current disclosure is used to control soilborne fungal diseases of soybeans at a use rate that is less than about 75%, less than about 60%, less than about 50%, less than about 40%, less than about 30%, less than about 20% or less than about 10% of the minimum use rate of a range of use rates listed on the label of a commercially available azoxystrobin product.

In various embodiments, the azoxystrobin formulations of the current disclosure may be used to control soilborne diseases of soybeans at active ingredient use rates of about 7.3-about 14.5 g per 1000 row meters, about 5.8-about 11.6 g per 1000 row meters, about 4.8-about 9.7 g per 1000 row meters, about 3.9-about 7.7 g per 1000 row meters, about 2.9-about 5.8 g per 1000 row meters, about 1.9-about 3.9 g per 1000 row meters or about 1.0-about 1.9 g per 1000 row meters. In some embodiments, the azoxystrobin formulations of the current disclosure may be used to control soilborne diseases of soybeans at active ingredient use rates of about less than about 1.0 g per 1000 row meters, less than about 1.9 g per 1000 row meters, less than about 2.9 g per 1000 row meters, less than about 3.9 g per 1000 row meters, less than about 4.8 g per 1000 row meters, less than about 5.8 g per 1000 row meters, less than about 7.3 g per 1000 row meters, less than about 7.7 g per 1000 row meters, less than about 9.7 g per 1000 row meters, less than about 11.6 g per 1000 row meters or less than about 14.5 g per 1000 row meters.

In various embodiments, the azoxystrobin formulations of the current disclosure may be used to control soilborne diseases of soybeans at active ingredient use rates of about 7.3-about 14.5 g per 1000 row meters, about 5.8-about 11.6 g per 1000 row meters, about 4.8-about 9.7 g per 1000 row meters, about 3.9-about 7.7 g per 1000 row meters, about 2.9-about 5.8 g per 1000 row meters, about 1.9-about 3.9 g per 1000 row meters or about 1.0-about 1.9 g per 1000 row meters.

In some embodiments, the azoxystrobin formulations of the current disclosure may be used to control soilborne diseases of soybeans at an active ingredient use rate of less than about 1.0 g per 1000 row meters, less than about 1.9 g per 1000 row meters, less than about 2.9 g per 1000 row meters, less than about 3.9 g per 1000 row meters, less than about 4.8 g per 1000 row meters, less than about 5.8 g per 1000 row meters, less than about 7.3 g per 1000 row meters, less than about 7.7 g per 1000 row meters, less than about 9.7 g per 1000 row meters, less than about 11.6 g per 1000 row meters or about less than about 14.5 g per 1000 row meters.

Non-limiting examples of the types of soilborne diseases of soybeans that can be controlled by azoxystrobin formulations of the present disclosure are *Rhizoctonia solani* and Southern blight (*Sclerotium rolfsii*).

In some embodiments, the azoxystrobin formulations of the current disclosure are used for plant health applications on soybean at a use rate that is lower than a use rate listed on the label of a commercially available azoxystrobin fungicide product. In some embodiments, the azoxystrobin formulations of the current disclosure are used for plant health applications on soybean at a use rate that is lower than the minimum use rate of a range of use rates listed on the label of a commercially available azoxystrobin fungicide product. In some embodiments, an azoxystrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available azoxystrobin fungicide product. When used for plant health applications, the azoxystrobin formulations of the present disclosure can be used at active ingredient rates that correspond to any of the values or ranges of values noted above for the control of fungal diseases on soybean.

In some embodiments, the use of the azoxystrobin formulations of the present disclosure in plant health applications on soybeans results in a yield increase (e.g., increased crop yield). In some embodiments, the yield increase corresponds to any of the values or ranges of values noted above for yield increases due to plant health applications.

Azoxystrobin—Cereals

In some embodiments, the azoxystrobin formulations of the present disclosure are used to control fungal diseases of cereals at an active ingredient use rate that is lower than the use rates listed on the label of commercially available azoxystrobin fungicides. In some embodiments, an azoxystrobin formulation of the current disclosure is used to control fungal diseases of cereals at a use rate that is 75%, 60%, 50%, 40%, 30%, 20%, or 10% of a use rate listed on the label of a commercially available azoxystrobin fungicide product.

Labels of commercially available azoxystrobin formulations often provide ranges of active ingredient use rates to control fungal disease of cereals. In some embodiments, the formulations of the current disclosure are used to control fungal disease at an active ingredient use rate that is lower than the minimum use rate of a range of use rates listed on the commercially available product's label. In some embodiments an azoxystrobin formulation of the current disclosure may be used to control fungal disease at a use rate that is less than about 75%, less than about 60%, less than about 50%, less than about 40%, less than about 30%, less than about 20% or less than about 10% of the minimum use rate of a range of use rates listed on the label of a commercially available product.

Examples of fungal diseases of cereals and corresponding active ingredient use rates for their control can be found on the labels of commercially available azoxystrobin fungicide products (e.g., Quadris® and Priori®). Examples of fungal diseases of cereals that can be controlled with formulations of the present disclosure include but are not limited to various blights, spots and rusts, rots, blasts and smuts.

In some embodiments, the azoxystrobin formulations of the current disclosure are used for plant health applications on cereals at a use rate that is lower than a use rate listed on the label of a commercially available azoxystrobin fungicide product. In some embodiments, the azoxystrobin formulations of the current disclosure are used for plant health applications on cereals at a use rate that is lower than the minimum use rate of a range of use rates listed on the label of a commercially available azoxystrobin fungicide product. In some embodiments, an azoxystrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available azoxystrobin fungicide product. When used for plant health applications, the azoxystrobin formulations of the present disclosure can be used at active ingredient rates that correspond to any of the values or ranges of values noted above for the control of fungal diseases on cereals.

Azoxystrobin—Cereals—Corn

Labelled use rates for the control of various fungal diseases of corn by Quadris, a commercially available azoxystrobin suspension concentrate, are provided in Table 5.

TABLE 5

| Product | Target Fungi | Use Rate (g ai/ha) |
|---|---|---|
| Quadris ® | Rust (*Puccinia sorghi*) | about 109-about 164 |
|  | Anthracnose leaf blight (*Colletotrichum graminicola*), Gray leaf spot (*Cercospora sorghi*), Northern corn leaf blight (*Setosphaeria turcica*), Northern corn leaf spot (*Cochliobolus carbonum*), Southern corn leaf blight (*Cochliobolus heterostrophus*), Eye spot (*Aureobasidium zeae*) | about 109-282 |
|  | Soilborne diseases: Southern blight (*Sclerotium rolfsii*), Rhizoctonia solani (*Rhizoctonia solani*) | 9.7-19.3 g/1000 row meters |

In some embodiments, the azoxystrobin formulations of the present disclosure are used to control fungal diseases of corn (including Field corn, pop corn, and sweet corn, as well as corn grown for seed production) at an active ingredient use rate that is lower than the use rate listed on the labels of commercially available azoxystrobin fungicides. In some embodiments, an azoxystrobin formulation of the current disclosure may be used to control fungal diseases of corn at a use rate that is less than 75%, less than 60%, less than 50%, less than 40%, less than 30%, less than 20%, or less than 10% of a use rate listed on the label of commercially available azoxystrobin fungicides.

In some embodiments, the azoxystrobin formulations of the current disclosure are used to control fungal disease of corn at an active ingredient use rate that is lower than the minimum use rate of a range of use rates listed on the labels of commercially available azoxystrobin products. In some embodiments an azoxystrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available azoxystrobin product.

In some embodiments, the azoxystrobin formulations of the current disclosure may be used to control fungal diseases of corn at an active ingredient use rate of about 82-about 212 g/ha, about 65-about 169 g/ha, about 54-about 141 g/ha, about 44-about 113 g/ha, about 33-about 85 g/ha, about 22-about 56 g/ha, or about 11-about 28 g/ha. In some embodiments, the azoxystrobin formulations of the current disclosure may be used to control fungal diseases of corn at an active ingredient use rate of about 82-about 123 g/ha, about 65-about 98 g/ha, about 55-about 82 g/ha, about 44-about 66 g/ha, about 33-about 49 g/ha, about 22-about 33 g/ha, or about 11-about 16 g/ha.

In some embodiments, the azoxystrobin formulations of the current disclosure may be used to control fungal diseases of corn at an active ingredient use rate of less than about 82 g/ha, less than about 65 g/ha, less than about 54 g/ha, less than about 44 g/ha, less than about 33 g/ha, less than about 22 g/ha, or less than about 11 g/ha. In some embodiments, the azoxystrobin formulations of the present disclosure may be used to control fungal diseases of corn at an active ingredient use rate of less than about 82 g/ha, less than about 65 g/ha, less than about 55 g/ha, less than about 44 g/ha, less than about 33 g/ha, less than about 22 g/ha, or less than about 11 g/ha.

Non-limiting examples of fungal diseases of corn that can be controlled with formulations of the present disclosure are Anthracnose leaf blight (*Colletotrichum graminicola*, Gray leaf spot (*Cercospora sorghi*), Northern corn leaf blight (*Setosphaeria turcica*), Northern corn leaf spot (*Cochliobolus carbonum*), Southern corn leaf blight (*Cochliobolus heterostrophus*) and Eye spot (*Aureobasidium zeae*).

In some embodiments, the azoxystrobin formulations of the present disclosure are used to control *Puccinia sorghi* at an active ingredient use rate of about 82-about 123 g/ha, about 65-about 98 g/ha, about 55-about 82 g/ha, about 44-about 66 g/ha, about 33-about 49 g/ha, about 22-about 33 g/ha, or about 11-about 16 g/ha.

In some embodiments, the azoxystrobin formulations of the current disclosure are used to control soilborne fungal diseases of corn at an active ingredient use rate that is lower than the use rate (or lower than the minimum use rate of a range of use rates) listed on the label of commercially available azoxystrobin fungicides. In some embodiments, a formulations of the current disclosure is used to control soilborne fungal diseases of corn at a use rate that is less than about 75%, less than about 60%, less than about 50%, less than about 40%, less than about 30%, less than about 20% or less than about 10% of a use rate listed on the label of a commercially available azoxystrobin fungicide product. In some embodiments, an azoxystrobin formulation of the current disclosure is used to control soilborne fungal diseases of corn at a use rate that is less than about 75%, less than about 60%, less than about 50%, less than about 40%, less than about 30%, less than about 20% or less than about 10% of the minimum use rate of a range of use rates listed on the label of a commercially available azoxystrobin fungicide product.

In various embodiments, the azoxystrobin formulations of the current disclosure may be used to control soilborne diseases of corn at active ingredient use rates of about 7.3-about 14.5 g per 1000 row meters, about 5.8-about 11.6 g per 1000 row meters, about 4.8-about 9.7 g per 1000 row meters, about 3.9-about 7.7 g per 1000 row meters, about 2.9-about 5.8 g per 1000 row meters, about 1.9-about 3.9 g per 1000 row meters or about 1.0-about 1.9 g per 1000 row meters. In some embodiments, the azoxystrobin formulations of the current disclosure may be used to control soilborne diseases of corn at active ingredient use rates of less than about 1.0 g per 1000 row meters, less than about 1.9 g per 1000 row meters, less than about 2.9 g per 1000 row meters, less than about 3.9 g per 1000 row meters, less than about 4.8 g per 1000 row meters, less than about 5.8 g per 1000 row meters, less than about 7.3 g per 1000 row meters, less than about 7.7 g per 1000 row meters, less than about 9.7 g per 1000 row meters, less than about 11.6 g per 1000 row meters or less than about 14.5 g per 1000 row meters.

Non-limiting examples of the types of soilborne diseases of corn that can be controlled by azoxystrobin formulations of the current disclosure are *Rhizoctonia* root and stalk rot (*Rhizoctonia solani*).

In some embodiments, the azoxystrobin formulations of the current disclosure are used for plant health applications on corn at a use rate that is lower than a use rate listed on the label of a commercially available azoxystrobin fungicide product. In some embodiments, the azoxystrobin formulations of the current disclosure are used for plant health applications on corn at a use rate that is lower than the minimum use rate of a range of use rates listed on the label of a commercially available azoxystrobin fungicide product. In some embodiments, an azoxystrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available azoxystrobin fungicide product. When used for plant health applications, the azoxystrobin formulations of the present disclosure can be used at active ingredient rates that correspond to any of the values or ranges of values noted above for the control of fungal diseases on corn.

Azoxystrobin—Cereals—Wheat

Labelled use rates for the control of various fungal diseases of wheat by Amistar® and Priori®, two commercially available azoxystrobin concentrates, are provided in Table 6.

TABLE 6

| Product | Target Fungi | Use Rate (g ai/ha) |
|---|---|---|
| Priori ® | *Bipolaris sorokiniana, Drechslera tritici-repentis, Puccinia triticina* | 50-100 |
| Amistar ® | Powdery mildew (*Erysiphe graminis*), *Septoria nodorum, Septoria* leaf blotch (*Septoria tritici*), *Drechslera tritici-repentis*, Yellow Rust (*Puccinia striiformis*), Brown Rust (*Puccinia recondita*) | 250 |

In some embodiments, the azoxystrobin formulations of the current disclosure are used to control fungal diseases of wheat at an active ingredient use rate that is lower than the use rate listed on the labels of commercially available azoxystrobin fungicides. In some embodiments, a formulation of the current disclosure is used to control fungal diseases of wheat at a use rate that is less than about 75%, less than about 60%, less than about 50%, less than about 40%, less than about 30%, less than about 20%, or less than about 10% of a use rate listed on the label of commercially available azoxystrobin fungicide products.

In some embodiments, the azoxystrobin formulations of the current disclosure are used to control fungal disease of wheat at an active ingredient use rate that is lower than the minimum use rate of a range of use rates listed on the label of a commercially available azoxystrobin product. In some embodiments an azoxystrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on a label of a commercially available azoxystrobin product.

In some embodiments, the azoxystrobin formulations of the current disclosure may be used to control fungal diseases of corn at an active ingredient use rate of about 37.5-about 75 g/ha, about 30-about 60 g/ha, about 25-about 50 g/ha, about 20-about 40 g/ha, about 15-about 30 g/ha, about 10-about 20 g/ha or about 5-about 10 g/ha.

In some embodiments, the azoxystrobin formulations of the current disclosure may be used to control fungal diseases of corn at an active ingredient use rate of less than about 37.5 g/ha, less than about 30 g/ha, less than about 25 g/ha, less than about 20 g/ha, less than about 15 g/ha, less than about 10 g/ha or less than about 5 g/ha.

In some embodiments, the azoxystrobin formulations of the present disclosure may be used to control fungal diseases of corn at an active ingredient use rate of less than about 187.5 g/ha, less than about 150 g/ha, less than about 125 g/ha, less than about 100 g/ha, less than about 75 g/ha, less than about 50 g/ha or less than about 25 g/ha.

Non-limiting examples of fungal diseases of wheat that can be controlled with formulations of the present disclosure are *Bipolaris sorokiniana*, tan spot (*Drechslera tritici-repentis*), and Wheat leaf rust (*Puccinia triticina*), and other fungal diseases listed in table X.

In some embodiments, the azoxystrobin formulations of the present disclosure are used for plant health applications on corn at a use rate that is lower than the use rate listed on the label of commercially available azoxystrobin fungicides. In some embodiment, the azoxystrobin formulations of the present disclosure are used at a rate that is 75%, 60%, 50%, 40%, 30%, 20% or 10% of the use rate listed on the labels of commercially available azoxystrobin fungicides. When used for plant health applications, the azoxystrobin formulations of the present disclosure can be used at an active ingredient use rate that corresponds to any of the values or ranges of values noted above for the control of fungal diseases on corn.

In some embodiments, the azoxystrobin formulations of the current disclosure are used for plant health applications on wheat at a use rate that is lower than a use rate listed on the label of a commercially available azoxystrobin fungicide product. In some embodiments, the azoxystrobin formulations of the current disclosure are used for plant health applications on wheat at a use rate that is lower than the minimum use rate of a range of use rates listed on the label of a commercially available azoxystrobin fungicide product. In some embodiments, an azoxystrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available azoxystrobin fungicide product. When used for plant health applications, the azoxystrobin formulations of the present disclosure can be used at active ingredient rates that correspond to any of the values or ranges of values noted above for the control of fungal diseases on wheat.

Azoxystrobin—Cereals—Rice

Labelled use rates for the control of various fungal diseases of rice by Quadris® and Priori®, two commercially available azoxystrobin concentrates, are provided in Table 7.

TABLE 7

| Product | Target Fungi | Use Rate (g ai/ha) |
|---|---|---|
| Quadris ® | Sheath blight (*Rhizoctonia solani*) | 164-228 |
| | Aggregate sheath spot (*Ceratobasidium oryzae-sativae* = *Rhizoctonia oryzae-sativae*), Black sheath rot (*Gaeumannomyces graminis* var. *graminis*), Sheath spot (*Rhizoctonia oryzae*), Stem rot (*Magnaporthe salvinii* = *Sclerotium oryzae* = *Nakateae sigmoidea*), Brown leaf spot (*Cochliobolus miyabeanus*), Leaf smut (*Entyloma oryzae*), Narrow brown leaf spot (*Cercospora janseana* = *Cercospora oryzae*), Kernel smut (*Tilletia barclayana* = *Neovossia barclayana*), Panicle blast (*Pyricularia grisea*) | 228-282 |
| Priori ® | *Bipolaris oryzae*, *Pyricularia grisea* | 100 |

In some embodiments, the azoxystrobin formulations of the current disclosure are used to control fungal diseases of rice at an active ingredient use rate that is lower than the use rate listed on the labels of commercially available azoxystrobin fungicides. In some embodiments, a formulation of the current disclosure is used to control fungal diseases of rice at a use rate that is less than about 75%, less than about 60%, less than about 50%, less than about 40%, less than about 30%, less than about 20%, or less than about 10% of a use rate listed on the label of commercially available azoxystrobin fungicide products.

In some embodiments, the azoxystrobin formulations of the current disclosure are used to control fungal disease of rice at an active ingredient use rate that is lower than the minimum use rate of a range of use rates listed on the label of a commercially available azoxystrobin product. In some embodiments an azoxystrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available azoxystrobin product.

In some embodiments, the azoxystrobin formulations of the current disclosure are used to control fungal diseases of rice at an active ingredient use rate of about 171-about 212 g/ha, about 137-about 169 g/ha, about 114-about 141 g/ha, about 91-about 113 g/ha, about 68-about 85 g/ha, about 46-about 56 g/ha or about 23-about 28 g/ha. In some embodiments, the azoxystrobin formulations of the present disclosure are used to control fungal diseases of rice at an active ingredient use rate of about 123-about 171 g/ha, about 98-about 137 g/ha, about 82-about 114 g/ha, about 66-about 91 g/ha, about 49-about 68 g/ha, about 33-about 46 g/ha or about 16-about 23 g/ha.

In some embodiments, the azoxystrobin formulations of the current disclosure are used to control fungal diseases of rice at an active ingredient use rate of less than about 171 g/ha, less than about 137 g/ha, less than about 114 g/ha, less than about 91 g/ha, less than about 68 g/ha, less than about 46 g/ha or less than about 23 g/ha. In some embodiments, the azoxystrobin formulations of the present disclosure are used to control fungal diseases of rice at an active ingredient use rate of less than about 123 g/ha, less than about 98 g/ha, less than about 82 g/ha, less than about 66 g/ha, less than about 49 g/ha, less than about 33 g/ha or less than about 16 g/ha.

In some embodiments, the azoxystrobin formulations of the present disclosure are used to control fungal diseases of rice at an active ingredient use rate of about 123-about 171 g/ha, about 98-about 137 g/ha, about 82-about 114 g/ha, about 66-about 91 g/ha, about 49-about 68 g/ha, about 33-about 46 g/ha or about 16-about 23 g/ha.

In some embodiments, the azoxystrobin formulations of the present disclosure are used to control fungal diseases of rice at an active ingredient use rate of less than about 123 g/ha, less than about 98 g/ha, less than about 82 g/ha, less than about 66 g/ha, less than about 49 g/ha, less than about 33 g/ha or less than about 16 g/ha.

In some embodiments, the azoxystrobin formulations of the current disclosure may be used to control fungal diseases of rice at an active ingredient use rates of less than about 75 g/ha, less than about 60 g/ha, less than about 50 g/ha, less than about 40 g/ha, less than about 30 g/ha, less than about 20 g/ha or less than about 10 g/ha.

Non-limiting examples of fungal diseases of rice that can be controlled with formulations of the present disclosure are Aggregate sheath spot (*Ceratobasidium oryzae-sativae=Rhizoctonia oryzae-sativae*), Black sheath rot (*Gaeumannomyces graminis* var. *graminis*), Sheath spot (*Rhizoctonia oryzae*), Stem rot (*Magnaporthe salvinii=Sclerotium oryzae=Nakateae sigmoidea*), Brown leaf spot (*Cochliobolus miyabeanus*), Leaf smut (*Entyloma oryzae*), Narrow brown leaf spot (*Cercospora janseana=Cercospora oryzae*), Kernel smut (*Tilletia barclayana=Neovossia barclayana*) Panicle blast (*Pyricularia grisea*) and *Bipolaris oryzae*.

In some embodiments, the azoxystrobin formulations of the current disclosure are used for plant health applications on rice at a use rate that is lower than a use rate listed on the label of a commercially available azoxystrobin fungicide product. In some embodiments, the azoxystrobin formulations of the current disclosure are used for plant health applications on rice at a use rate that is lower than the minimum use rate of a range of use rates listed on the label of a commercially available azoxystrobin fungicide product. In some embodiments, an azoxystrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available azoxystrobin fungicide product. When used for plant health applications, the azoxystrobin formulations of the present disclosure can be used at active ingredient rates that correspond to any of the values or ranges of values noted above for the control of fungal diseases on rice.

Azoxystrobin—Potatoes

Labelled use rates for the control of various fungal diseases of potatoes by Quadris®, a commercially available azoxystrobin suspension concentrate, are provided in Table 8.

TABLE 8

| Product | Target Fungi | Use Rate (g ai/ha) |
|---|---|---|
| Quadris ® | Early blight (*Alternaria solani*), Late blight (*Phytophthora infestans*), Black dot (*Colletotrichum coccodes*), Powdery mildew (*Erysiphe cichoracearum*) | 109-282 |
| | Soilborne Diseases Black scurf (*Rhizoctonia solani*), Silver scurf (*Helminthosporium solani*), Black dot (*Colletotrichum coccodes*) | 9.7-9.3 g/1000 row meters |

In some embodiments, the azoxystrobin formulations of the current disclosure are used to control fungal diseases of potatoes at an active ingredient use rate that is lower than the use rate listed on the labels of commercially available azoxystrobin fungicides. In some embodiments, a formulation of the current disclosure is used to control fungal diseases of potatoes at a use rate that is less than about 75%, less than about 60%, less than about 50%, less than about 40%, less than about 30%, less than about 20%, or less than about 10% of a use rate listed on the label of commercially available azoxystrobin fungicide products.

In some embodiments, the azoxystrobin formulations of the current disclosure are used to control fungal disease of potatoes at an active ingredient use rate that is lower than the minimum use rate of a range of use rates listed on the label of a commercially available azoxystrobin product. In some embodiments an azoxystrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available azoxystrobin product.

In some embodiments, the azoxystrobin formulations of the present disclosure are used to control fungal diseases of potatoes at an active ingredient use rate of about 82-about 212 g/ha, about 66-about 169 g/ha, about 55-about 141 g/ha, about 44-about 113 g/ha, about 33-about 85 g/ha, about 22-about 56 g/ha or about 11-about 28 g/ha.

In some embodiments, the azoxystrobin formulations of the present disclosure are used to control fungal diseases of potatoes at an active ingredient use rate of less than about 82 g/ha, less than about 66 g/ha, less than about 55 g/ha, less than about 44 g/ha, less than about 33 g/ha, less than about 22 g/ha or less than about 11 g/ha.

Non-limiting examples of fungal diseases of potatoes that can be controlled with formulations of the present disclosure are Early blight (*Alternaria solani*), Late blight (*Phytophthora infestans*), Black dot (*Colletotrichum coccodes*) and Powdery mildew (*Erysiphe cichoracearum*).

In some embodiments, the azoxystrobin formulations of the present disclosure may be used to control soilborne fungal diseases of potatoes at an active ingredient use rate that is lower than the use rate (or minimum rate of a range of use rates) listed on the label of a commercially available azoxystrobin fungicide product. In some embodiments, the formulations of the current disclosure are used to control soilborne fungal diseases of potatoes at a use rate that is less than about 75%, about 60%, about 50%, about 40%, about 30%, about 20% or about 10% of the use rate (or minimum use rate of a range of use rates) listed on the label of a commercially available azoxystrobin fungicide product.

In various embodiments, the azoxystrobin formulations of the current disclosure may be used to control soilborne diseases of potatoes at active ingredient use rates of about 7.3-about 14.5 g per 1000 row meters, about 5.8-about 11.6 g per 1000 row meters, about 4.8-about 9.7 g per 1000 row meters, about 3.9-about 7.7 g per 1000 row meters, about 2.9-about 5.8 g per 1000 row meters, about 1.9-about 3.9 g per 1000 row meters or about 1.0-about 1.9 g per 1000 row meters. In various embodiments, the azoxystrobin formulations of the current disclosure may be used to control soilborne diseases of potatoes at active ingredient use rates of less than about 7.3 g per 1000 row meters, less than about 5.8 g per 1000 row meters, less than about 4.8 g per 1000 row meters, less than about 3.9 g per 1000 row meters, less than about 2.9 g per 1000 row meters, less than about 1.9 g per 1000 row meters or less than about 1.0 g per 1000 row meters.

Non-limiting examples of the types of soilborne diseases of potatoes that can be controlled by azoxystrobin formulations of the present disclosure are Black scurf (*Rhizoctonia solani*), Silver scurf (*Helminthosporium solani*), Black dot (*Colletotrichum coccodes*).

In some embodiments, the azoxystrobin formulations of the current disclosure are used for plant health applications on potatoes at a use rate that is lower than a use rate listed on the label of a commercially available azoxystrobin fungicide product. In some embodiments, the azoxystrobin formulations of the current disclosure are used for plant health applications on potatoes at a use rate that is lower than the minimum use rate of a range of use rates listed on the label of a commercially available azoxystrobin fungicide product. In some embodiments, an azoxystrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available azoxystrobin fungicide product. When used for plant health applications, the azoxystrobin formulations of the present disclosure can be used at active ingredient rates that correspond to any of the values or ranges of values noted above for the control of fungal diseases on potatoes.

Azoxystrobin—Turf, Ornamental and Other Applications

In some embodiments, the azoxystrobin formulations of the present disclosure are used to control fungal diseases of turf, ornamental, and landscape plants, sod and turf grasses grown for seed. In some embodiments, the formulations of the present disclosure are used to control fungal disease of the aforementioned plants at an active ingredient use rate that is lower than the use rate listed on the label of commercially available azoxystrobin fungicides. In some embodiments, the formulations of the current disclosure are used to control fungal diseases of turf, ornamental and landscape plants at a use rate that is less than about 75%, about 60%, about 50%, about 40%, about 30%, about 20%, or about 10% of the use rate listed on commercially available azoxystrobin fungicides.

In some embodiments, the azoxystrobin formulations of the current disclosure are used to control fungal disease of turf, ornamental, and landscape plants, sod and turf grasses grown for seed at an active ingredient use rate that is lower than the minimum use rate of a range of use rates listed on the label of a commercially available azoxystrobin product. In some embodiments an azoxystrobin formulation of the current disclosure is used to control fungal disease of the aforementioned plants at a use rate that is less than about 75%, less than about 60%, less than about 50%, less than about 40%, less than about 30%, less than about 20% or less than about 10% of the minimum use rate of a range of use rates listed on the label of a commercially available azoxystrobin product.

Examples of the aforementioned plants on which fungal disease can be controlled by formulations of the present disclosure can be found on the labels of commercially available azoxystrobin fungicides (e.g., Heritage® etc.).

In some embodiments, the azoxystrobin formulations of the present disclosure are used for plant health applications on the aforementioned plants at a use rate that is lower than the use rate (or minimum use rate of a range of use rates) listed on the label of a commercially available azoxystrobin fungicide product (e.g., Heritage®). In some embodiments, the azoxystrobin formulations of the current disclosure are used at a rate that is less than about 75%, about 60%, about 50%, about 40%, about 30%, about 20% or about 10% of the use rate (or minimum use rate of a range of use rates) listed on the label of a commercially available azoxystrobin fungicide product. When used for plant health applications, the azoxystrobin formulations of the current disclosure can be used at active ingredient rates that correspond to any of the values or ranges of values noted above for the control of fungal diseases on turf, ornamental, and landscape plants, sod and turf grasses grown for seed.

Pyraclostrobin

In various embodiments, the pyraclostrobin formulations of the current disclosure may be used to control fungal diseases at active ingredient use rates that are lower than the use rates listed on the labels of commercially available pyraclostrobin fungicides. In some embodiments, a pyraclostrobin formulation of the current disclosure may be used to control fungal disease at a use rate that is less than about 75%, less than about 60%, less than about 50%, less than about 40%, less than about 30%, less than about 20% or less than about 10% of a use rate listed on the label of a commercially available pyraclostrobin fungicide product.

Labels of commercially available pyraclostrobin products often provide ranges of active ingredient use rates to control certain fungal diseases on certain plants (e.g., crops). In some embodiments, the pyraclostrobin formulations of the current disclosure are used to control fungal disease at an active ingredient use rate that is lower than the minimum use rate of a range of use rates listed on the label of a commercially available pyraclostrobin product. In some embodiments a pyraclostrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available product.

Pyraclostrobin—Cereals

In some embodiments, the pyraclostrobin formulations of the current disclosure are used to control fungal diseases of cereals at an active ingredient use rate that is lower than the use rate listed on the labels of commercially available pyraclostrobin fungicides. In some embodiments, a formulation of the current disclosure is used to control fungal diseases of cereals at a use rate that is less than about 75%, less than about 60%, less than about 50%, less than about 40%, less than about 30%, less than about 20%, or less than about 10% of a use rate listed on the label of commercially available pyraclostrobin fungicide products.

In some embodiments, the pyraclostrobin formulations of the current disclosure are used to control fungal disease of cereals at an active ingredient use rate that is lower than the minimum use rate of a range of use rates listed on the label of a commercially available pyraclostrobin product. In some embodiments an pyraclostrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available pyraclostrobin product.

Examples of fungal diseases of cereals and corresponding active ingredient use rates for their control can be found on the labels of commercially available pyraclostrobin fungicide products (e.g., Headline®). Examples of fungal diseases of cereals that can be controlled with formulations of the present disclosure include but are not limited to various blights, spots and rusts, rots, blasts and smuts.

In some embodiments, the pyraclostrobin formulations of the current disclosure are used for plant health applications on cereals at a use rate that is lower than a use rate listed on the label of a commercially available pyraclostrobin fungicide product. In some embodiments, the pyraclostrobin formulations of the current disclosure are used for plant health applications on cereals at a use rate that is lower than the minimum use rate of a range of use rates listed on the label of commercially available pyraclostrobin fungicide product. In some embodiments, a pyraclostrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available pyraclostrobin fungicide product. When used for plant health applications, the pyraclostrobin formulations of the present disclosure can be used at active ingredient rates that correspond to any of the values or ranges of values noted above for the control of fungal diseases on cereals.

Pyraclostrobin—Cereals—Wheat

Labelled use rates for the control of various fungal diseases of wheat by Headline®, Comet® and Comet 200®, three commercially available pyraclostrobin emulsion concentrates, are provided in Table 9.

TABLE 9

| Product | Target Fungi | Use Rate (g ai/ha) |
|---|---|---|
| Headline ® | Black Spot, Leaf Rust, Powdery Mildew, *Septoria* Leaf And Glume Blotch, Spot Blotch, Stem Rust, Stripe Rust, Tan Spot (Yellow Leaf Spot) | 110-165 |

TABLE 9-continued

| Product | Target Fungi | Use Rate (g ai/ha) |
|---|---|---|
| Comet ® | Drecheslera tritici-repentis, Pucciniatriticina, Bipolaris sorokiniana, Leptosphaeria nodorum, Septoria tritici | 150-200 |
| Comet 200 ® | Septoria tritici, Septoria nodorum, Yellow rust, brown rust | 250 |

In some embodiments, the pyraclostrobin formulations of the current disclosure are used to control fungal diseases of wheat at an active ingredient use rate that is lower than the use rate listed on the labels of commercially available pyraclostrobin fungicides. In some embodiments, a pyraclostrobin formulation of the current disclosure is used to control fungal diseases of wheat at a use rate that is less than about 75%, less than about 60%, less than about 50%, less than about 40%, less than about 30%, less than about 20%, or less than about 10% of a use rate listed on the label of a commercially available pyraclostrobin fungicide product.

In some embodiments, the pyraclostrobin formulations of the current disclosure are used to control fungal disease of wheat at an active ingredient use rate that is lower than the minimum use rate of a range of use rates listed on the label of a commercially available pyraclostrobin product. In some embodiments a pyraclostrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available pyraclostrobin product.

In some embodiments, the pyraclostrobin formulations of the present disclosure are used to control fungal diseases of wheat at an active ingredient use rate of about 82-about 124 g/ha, about 66-about 99 g/ha, about 55-about 82 g/ha, about 44-about 66 g/ha, about 33-about 49 g/ha, about 22-about 33 g/ha or about 11-about 16 g/ha. In some embodiments, the pyraclostrobin formulations of the present disclosure are used to control fungal diseases of wheat at an active ingredient use rate of about 112.5-about 150 g/ha, about 90-about 120 g/ha, about 75-about 100 g/ha, about 60-about 80 g/ha, about 45-about 60 g/ha, about 30-about 40 g/ha or about 15-about 20 g/ha.

In some embodiments, the pyraclostrobin formulations of the present disclosure are used to control fungal diseases of wheat at an active ingredient use rate of less than about 82 g/ha, less than about 66 g/ha, less than about 55 g/ha, less than about 44 g/ha, less than about 33 g/ha, less than about 22 g/ha or less than about 11 g/ha. In some embodiments, the pyraclostrobin formulations of the present disclosure are used to control fungal diseases of wheat at an active ingredient use rate of less than about 112.5 150 g/ha, less than about 90 g/ha, less than about 75 g/ha, less than about 60 g/ha, less than about 45 g/ha, less than about 30 g/ha or less than about 15 g/ha.

In some embodiments, the pyraclostrobin formulations of the current disclosure can be used to control fungal diseases of wheat at an active ingredient use rates of about less than about 187.5 g/ha, less than about 150 g/ha, less than about 125 g/ha, less than about 100 g/ha, less than about 75 g/ha, less than about 50 g/ha, or less than about 25 g/ha.

Non-limiting examples of fungal diseases of wheat that can be controlled with formulations of the present disclosure include those listed in Table 9, above.

In some embodiments, the pyraclostrobin formulations of the current disclosure are used for plant health applications on wheat at a use rate that is lower than a use rate listed on the label of a commercially available pyraclostrobin fungicide product. In some embodiments, the pyraclostrobin formulations of the current disclosure are used for plant health applications on wheat at a use rate that is lower than the minimum use rate of a range of use rates listed on the label of a commercially available pyraclostrobin fungicide product. In some embodiments, a pyraclostrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available pyraclostrobin fungicide product. When used for plant health applications, the pyraclostrobin formulations of the present disclosure can be used at active ingredient rates that correspond to any of the values or ranges of values noted above for the control of fungal diseases on wheat.

Pyraclostrobin—Cereals—Corn

Labelled use rates for the control of various fungal diseases of corn by Headline®, Comet® and Comet 200®, there commercially available pyraclostrobin emulsion concentrates, are provided in Table 10.

TABLE 10

| Product | Target Fungi | Use Rate (g ai/ha) |
|---|---|---|
| Headline ® | On corn (all types, including field, sweet, pop, field corn, and corn grown for seed production): Anthracnose, Gray Leaf Spot, Northern Corn Leaf Blight, Physoderma Brown Spot, Common Rust, Southern Rust, Southern Corn Leaf Blight, Yellow Leaf Blight | 110-220 |
| Comet ® | Puccinia polysora, Phaeosphaeria maydis | 150 |

In some embodiments, the pyraclostrobin formulations of the current disclosure are used to control fungal diseases of corn at an active ingredient use rate that is lower than the use rate listed on the labels of commercially available pyraclostrobin fungicides. In some embodiments, a pyraclostrobin formulation of the current disclosure is used to control fungal diseases of corn at a use rate that is less than about 75%, less than about 60%, less than about 50%, less than about 40%, less than about 30%, less than about 20%, or less than about 10% of a use rate listed on the label of a commercially available pyraclostrobin fungicide product.

In some embodiments, the pyraclostrobin formulations of the current disclosure are used to control fungal disease of corn at an active ingredient use rate that is lower than the minimum use rate of a range of use rates listed on the label of a commercially available pyraclostrobin product. In some embodiments a pyraclostrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available pyraclostrobin product.

In some embodiments, the pyraclostrobin formulations of the present disclosure are used to control fungal diseases of corn at an active ingredient use rate of about 82-about 165 g/ha, about 66-about 132 g/ha, about 55-about 110 g/ha, about 44-about 88 g/ha, about 33-about 66 g/ha, about 22-about 44 g/ha or about 11-about 22 g/ha.

In some embodiments, the pyraclostrobin formulations of the present disclosure are used to control fungal diseases of corn at an active ingredient use rate of less than about 82 g/ha, less than about 66 g/ha, less than about 55 g/ha, less than about 44 g/ha, less than about 33 g/ha, less than about 22 44 g/ha or less than about 11 g/ha.

In some embodiments, the pyraclostrobin formulations of the current disclosure can be used to control fungal diseases of corn at an active ingredient use rates of less than about 112.5 g/ha, less than about 90 g/ha, less than about 75 g/ha, less than about 60 g/ha, less than about 45 g/ha, less than about 30 g/ha, or less than about 15 g/ha.

Non-limiting examples of fungal diseases of corn that can be controlled with pyraclostrobin formulations of the present disclosure include those listed in Table 10, above.

In some embodiments, the pyraclostrobin formulations of the current disclosure are used for plant health applications on corn at a use rate that is lower than a use rate listed on the label of a commercially available pyraclostrobin fungicide product. In some embodiments, the pyraclostrobin formulations of the current disclosure are used for plant health applications on corn at a use rate that is lower than the minimum use rate of a range of use rates listed on the label of a commercially available pyraclostrobin fungicide product. In some embodiments, a pyraclostrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available pyraclostrobin fungicide product. When used for plant health applications, the pyraclostrobin formulations of the present disclosure can be used at active ingredient rates that correspond to any of the values or ranges of values noted above for the control of fungal diseases on corn.

Pyraclostrobin—Soybean

Labelled use rates for the control of various fungal diseases of soybean by Headline®, and Comet®, two commercially available pyraclostrobin emulsion concentrates, are provided in Table 11.

TABLE 11

| Product | Target Fungi | Use Rate (g ai/ha) |
| --- | --- | --- |
| Headline ® | *Alternaria* Leaf Spot, Anthracnose, Asian Soybean Rust, Brown Spot, *Cercospora* Blight, Frogeye Leaf Spot, Pod and Stem Blight, *Rhizoctonia* Aerial Blight | 110-220 |
| | Suppression only: Southern blight | 220 |
| Comet ® | *Mycrosphaera diffusa, Cercospora kikuchii, Septoria glycines, Corynespora cassiicola* | 75 |

In some embodiments, the pyraclostrobin formulations of the current disclosure are used to control fungal diseases of soybean at an active ingredient use rate that is lower than the use rate listed on the labels of commercially available pyraclostrobin fungicides. In some embodiments, a pyraclostrobin formulation of the current disclosure is used to control fungal diseases of soybean at a use rate that is less than about 75%, less than about 60%, less than about 50%, less than about 40%, less than about 30%, less than about 20%, or less than about 10% of a use rate listed on the label of a commercially available pyraclostrobin fungicide product.

In some embodiments, the pyraclostrobin formulations of the current disclosure are used to control fungal disease of soybean at an active ingredient use rate that is lower than the minimum use rate of a range of use rates listed on the label of a commercially available pyraclostrobin product. In some embodiments a pyraclostrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available pyraclostrobin product.

In some embodiments, the pyraclostrobin formulations of the present disclosure are used to control fungal diseases of soybean at an active ingredient use rate of about 82-about 165 g/ha, about 66-about 132 g/ha, about 55-about 110 g/ha, about 44-about 88 g/ha, about 33-about 66 g/ha, about 22-about 44 g/ha or about 11-about 22 g/ha.

In some embodiments, the pyraclostrobin formulations of the present disclosure are used to control fungal diseases of soybean at an active ingredient use rate of less than about 82 g/ha, less than about 66 g/ha, less than about 55 g/ha, less than about 44 g/ha, less than about 33 g/ha, less than about 22 g/ha or less than about 11 g/ha.

In some embodiments, the pyraclostrobin formulations of the present disclosure can be used to control fungal diseases of soybean at an active ingredient use rate of less than about 165 g/ha, less than about 131 g/ha, less than about 110 g/ha, less than about 88 g/ha, less than about 66 g/ha, less than about 44 g/ha, or less than about 22 g/ha. In some embodiments, the pyraclostrobin formulations of the current disclosure can be used to control fungal diseases of soybean at an active ingredient use rate of less than about 56 g/ha, less than about 45 g/ha, less than about 37.5 g/ha, less than about 30 g/ha, less than about 22.5 g/ha, less than about 15 g/ha, or less than about 7.5 g/ha.

Non-limiting examples of fungal diseases of soybeans that can be controlled with formulations of the present disclosure include those listed in Table 11, above.

In some embodiments, the pyraclostrobin formulations of the current disclosure are used for plant health applications on soybean at a use rate that is lower than a use rate listed on the label of a commercially available pyraclostrobin fungicide product. In some embodiments, the pyraclostrobin formulations of the current disclosure are used for plant health applications on soybean at a use rate that is lower than the minimum use rate of a range of use rates listed on the label of a commercially available pyraclostrobin fungicide product. In some embodiments, a pyraclostrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available pyraclostrobin fungicide product. When used for plant health applications, the pyraclostrobin formulations of the present disclosure can be used at active ingredient rates that correspond to any of the values or ranges of values noted above for the control of fungal diseases on soybean.

Pyraclostrobin—Cucurbits

Labelled use rates for the control of various fungal diseases of Cucurbits (vine crops) by Cabrio® and Comet®, a commercially available pyraclostrobin water-dispersible granule, are provided in Table 12.

TABLE 12

| Product | Cucurbit Vegetables Labelled | Target Fungi | Use Rate (g ai/ha) |
| --- | --- | --- | --- |
| Cabrio ® EG | Cantaloupe, Chayote, Chinese Waxgourd, Citron Melon, Cucumber, Edible Gourds, Gherkin, Muskmelon, Pumpkin, Summer Squash, Watermelon, Winter Squash, Zucchini, *Mormordica* Spp. (Such As Balsam Pear, Balsam Apple, Bitter Melon, Chinese Cucumber) | Downey mildew | 112-168 |
|  |  | *Alternaria* Blight, Anthracnose, *Cercospora* Leaf Spot, Gummy Stem Blight, *Plectosporium* Blight, Powdery Mildew, Target Leaf Blight | 68-224 |
| Comet ® | Melon, watermelon | *Sphaerotheca fuliginea*, *Pseudoperonospora cubensis* | 100 |

In some embodiments, the pyraclostrobin formulations of the current disclosure are used to control fungal diseases of Cucurbits at an active ingredient use rate that is lower than the use rate listed on the labels of commercially available pyraclostrobin fungicides. In some embodiments, a pyraclostrobin formulation of the current disclosure is used to control fungal diseases of Cucurbits at a use rate that is less than about 75%, less than about 60%, less than about 50%, less than about 40%, less than about 30%, less than about 20%, or less than about 10% of a use rate listed on the label of a commercially available pyraclostrobin fungicide product.

In some embodiments, the pyraclostrobin formulations of the current disclosure are used to control fungal disease of Cucurbits at an active ingredient use rate that is lower than the minimum use rate of a range of use rates listed on the label of a commercially available pyraclostrobin product. In some embodiments a pyraclostrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available pyraclostrobin product.

In some embodiments, the pyraclostrobin formulations of the present disclosure may be used to control fungal diseases of Cucurbits at an active ingredient use rate of about 84-about 126 g/ha, about 67-about 101 g/ha, about 56-about 84 g/ha, about 45-about 67 g/ha, about 34-about 50 g/ha, about 22-about 34 g/ha or about 11-about 17 g/ha. In some embodiments, the pyraclostrobin formulations of the present disclosure may be used to control fungal diseases of Cucurbits at an active ingredient use rate of about 126-about 168 g/ha, about 101-about 135 g/ha, about 84-about 112 g/ha, about 67-about 90 g/ha, about 50-about 67 g/ha, about 34-about 45 g/ha or about 17-about 22 g/ha.

In some embodiments, the pyraclostrobin formulations of the present disclosure may be used to control fungal diseases of Cucurbits at an active ingredient use rate of less than about 84 g/ha, less than about 67 g/ha, less than about 56 g/ha, less than about 45 g/ha, less than about 34 g/ha, less than about 22 g/ha or less than about 11 g/ha. In some embodiments, the pyraclostrobin formulations of the present disclosure may be used to control fungal diseases of Cucurbits at an active ingredient use rate of less than about 126 g/ha, less than about 101 g/ha, less than about 84 g/ha, less than about 67 90 g/ha, less than about 50 g/ha, less than about 34 g/ha or less than about 17 g/ha.

In some embodiments, the pyraclostrobin formulations of the current disclosure can be used to control fungal diseases of Cucurbits at an active ingredient use rate of less than about 112.5 g/ha, less than about 90 g/ha, less than about 75 g/ha, less than about 60 g/ha, less than about 45 g/ha, less than about 30 g/ha, or less than about 15 g/ha.

Non-limiting examples of fungal diseases of Cucurbits that can be controlled with formulations of the present disclosure include those listed in Table 12, above.

In some embodiments, the pyraclostrobin formulations of the current disclosure are used for plant health applications on Cucurbits at a use rate that is lower than a use rate listed on the label of a commercially available pyraclostrobin fungicide product. In some embodiments, the pyraclostrobin formulations of the current disclosure are used for plant health applications on Cucurbits at a use rate that is lower than the minimum use rate of a range of use rates listed on the label of a commercially available pyraclostrobin fungicide product. In some embodiments, a pyraclostrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available pyraclostrobin fungicide product. When used for plant health applications, the pyraclostrobin formulations of the present disclosure can be used at active ingredient rates that correspond to any of the values or ranges of values noted above for the control of fungal diseases on Cucurbits.

Trifloxystrobin

In various embodiments, the trifloxystrobin formulations of the current disclosure may be used to control fungal diseases at active ingredient use rates that are lower than the use rates listed on the labels of commercially available trifloxystrobin fungicides. In some embodiments, a trifloxystrobin formulation of the current disclosure may be used to control fungal disease at a use rate that is less than about 75%, less than about 60%, less than about 50%, less than about 40%, less than about 30%, less than about 20% or less than about 10% of a use rate listed on the label of a commercially available trifloxystrobin fungicide product.

Labels of commercially available trifloxystrobin products often provide ranges of active ingredient use rates to control certain fungal diseases on certain plants (e.g., crops). In some embodiments, the trifloxystrobin formulations of the current disclosure are used to control fungal disease at an active ingredient use rate that is lower than the minimum use rate of a range of use rates listed on the label of a commercially available trifloxystrobin product. In some embodiments a trifloxystrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available product.

Trifloxystrobin—Cereals

In some embodiments, the trifloxystrobin formulations of the current disclosure are used to control fungal diseases of cereals at an active ingredient use rate that is lower than the use rate listed on the labels of commercially available azoxystrobin fungicides. In some embodiments, a trifloxystrobin formulation of the current disclosure is used to control fungal diseases of cereals at a use rate that is less than about 75%, less than about 60%, less than about 50%, less than about 40%, less than about 30%, less than about 20%, or less than about 10% of a use rate listed on the label of a commercially available trifloxystrobin fungicide product.

In some embodiments, the trifloxystrobin formulations of the current disclosure are used to control fungal disease of cereals at an active ingredient use rate that is lower than the minimum use rate of a range of use rates listed on the label of a commercially available trifloxystrobin product. In some embodiments a trifloxystrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available trifloxystrobin product.

Examples of fungal diseases of cereals and corresponding active ingredient use rates for their control can be found on the labels of commercially available trifloxystrobin fungicide products. Examples of fungal diseases of cereals that can be controlled with formulations of the present disclosure include but are not limited to various fungal diseases of cereal noted in other portions of the specification.

In some embodiments, the trifloxystrobin formulations of the current disclosure are used for plant health applications on Cereals at a use rate that is lower than a use rate listed on the label of a commercially available trifloxystrobin fungicide product. In some embodiments, the trifloxystrobin formulations of the current disclosure are used for plant health applications on Cereals at a use rate that is lower than the minimum use rate of a range of use rates listed on the label of commercially available trifloxystrobin fungicide product. In some embodiments, a trifloxystrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available trifloxystrobin fungicide product. When used for plant health applications, the trifloxystrobin formulations of the present disclosure can be used at active ingredient rates that correspond to any of the values or ranges of values noted above for the control of fungal diseases on Cereals.

Trifloxystrobin—Cereals—Rice

Labelled use rates for the control of various fungal diseases of rice by Gem™ a commercially trifloxystrobin fungicide, are provided in Table 13.

TABLE 13

| Product | Target Fungi | Use Rate (g ai/ha) |
| --- | --- | --- |
| Gem ™ | Sheath Blight (*Rhizoctonia solani*) | 139-172 |
|  | Rice Blast (*Pyricularia grisea*) | 113-172 |

In some embodiments, the trifloxystrobin formulations of the current disclosure are used to control fungal diseases of rice at an active ingredient use rate that is lower than the use rate listed on the labels of commercially available trifloxystrobin fungicides. In some embodiments, a trifloxystrobin formulation of the current disclosure is used to control fungal diseases of rice at a use rate that is less than about 75%, less than about 60%, less than about 50%, less than about 40%, less than about 30%, less than about 20%, or less than about 10% of a use rate listed on the label of a commercially available trifloxystrobin fungicide product.

In some embodiments, the trifloxystrobin formulations of the current disclosure are used to control fungal disease of rice at an active ingredient use rate that is lower than the minimum use rate of a range of use rates listed on the label of a commercially available trifloxystrobin product. In some embodiments a trifloxystrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available trifloxystrobin product.

In some embodiments, the trifloxystrobin formulations of the present disclosure may be used to control fungal diseases of rice at an active ingredient use rate of about 104-about 129 g/ha, about 83-about 103 g/ha, about 69-about 86 g/ha, about 56-about 69 g/ha, about 42-about 51 g/ha, about 28-about 34 g/ha or about 14-about 17 g/ha. In some embodiments, the trifloxystrobin formulations of the present disclosure may be used to control fungal diseases of rice at an active ingredient use rate of about 85-about 129 g/ha, about 68-about 103 g/ha, about 57-about 86 g/ha, about 45-about 69 g/ha, about 34-about 51 g/ha, about 23-about 34 g/ha or about 11-about 17 g/ha.

In some embodiments, the trifloxystrobin formulations of the present disclosure may be used to control fungal diseases of rice at an active ingredient use rate of less than about 104-about 129 g/ha, less than about 83 g/ha, less than about 69 g/ha, less than about 56 g/ha, less than about 42 g/ha, less than about 28 g/ha or less than about 14 g/ha. In some embodiments, the trifloxystrobin formulations of the present disclosure may be used to control fungal diseases of rice at an active ingredient use rate of less than about 85 g/ha, less than about 68 g/ha, less than about 57 g/ha, less than about 45 g/ha, less than about 34 g/ha, less than about 23 g/ha or less than about 11 g/ha.

In some embodiments, the trifloxystrobin formulations of the current disclosure are used for plant health applications on rice at a use rate that is lower than a use rate listed on the label of a commercially available trifloxystrobin fungicide product. In some embodiments, the trifloxystrobin formulations of the current disclosure are used for plant health applications on rice at a use rate that is lower than the minimum use rate of a range of use rates listed on the label of commercially available trifloxystrobin fungicide product. In some embodiments, a trifloxystrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available trifloxystrobin fungicide product. When used for plant health applications, the trifloxystrobin formulations of the present disclosure can be used at active ingredient rates that correspond to any of the values or ranges of values noted above for the control of fungal diseases on rice.

Trifloxystrobin—Cereals—Corn

In some embodiments, the trifloxystrobin formulations of the current disclosure are used to control fungal diseases of corn at an active ingredient use rate that is lower than the use rate listed on the labels of commercially available trifloxystrobin fungicides. In some embodiments, a trifloxystrobin formulation of the current disclosure is used to control fungal diseases of corn at a use rate that is less than about 75%, less than about 60%, less than about 50%, less than about 40%, less than about 30%, less than about 20%, or less than about 10% of a use rate listed on the label of a commercially available trifloxystrobin fungicide product.

In some embodiments, the trifloxystrobin formulations of the current disclosure are used to control fungal disease of corn at an active ingredient use rate that is lower than the minimum use rate of a range of use rates listed on the label of a commercially available trifloxystrobin product. In some embodiments a trifloxystrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available trifloxystrobin product.

Examples of fungal diseases of corn that can be controlled with trifloxystrobin of the present disclosure include but are not limited to various fungal diseases of corn noted in any other portion of the specification.

In some embodiments, the trifloxystrobin formulations of the current disclosure are used for plant health applications on corn at a use rate that is lower than a use rate listed on the label of a commercially available trifloxystrobin fungicide product. In some embodiments, the trifloxystrobin formulations of the current disclosure are used for plant health applications on corn at a use rate that is lower than the minimum use rate of a range of use rates listed on the label of commercially available trifloxystrobin fungicide product. In some embodiments, a trifloxystrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available trifloxystrobin fungicide product. When used for plant health applications, the trifloxystrobin formulations of the present disclosure can be used at active ingredient rates that correspond to any of the values or ranges of values noted above for the control of fungal diseases on corn.

Trifloxystrobin—Soybean

In some embodiments, the trifloxystrobin formulations of the current disclosure are used to control fungal diseases of soybean at an active ingredient use rate that is lower than the use rate listed on the labels of commercially available trifloxystrobin fungicides. In some embodiments, a trifloxystrobin formulation of the current disclosure is used to control fungal diseases of soybean at a use rate that is less than about 75%, less than about 60%, less than about 50%, less than about 40%, less than about 30%, less than about 20%, or less than about 10% of a use rate listed on the label of a commercially available trifloxystrobin fungicide product.

In some embodiments, the trifloxystrobin formulations of the current disclosure are used to control fungal disease of soybean at an active ingredient use rate that is lower than the minimum use rate of a range of use rates listed on the label of a commercially available trifloxystrobin product. In some embodiments a trifloxystrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available trifloxystrobin product.

Examples of fungal diseases of soybean and corresponding active ingredient use rates for their control can be found on the labels of commercially available trifloxystrobin fungicide products. Examples of fungal diseases of soybean that can be controlled with formulations of the present disclosure include but are not limited to various fungal diseases of soybean noted in any other portion of the specification.

In some embodiments, the trifloxystrobin formulations of the current disclosure are used for plant health applications on soybean at a use rate that is lower than a use rate listed on the label of a commercially available trifloxystrobin fungicide product. In some embodiments, the trifloxystrobin formulations of the current disclosure are used for plant health applications on soybean at a use rate that is lower than the minimum use rate of a range of use rates listed on the label of commercially available trifloxystrobin fungicide product. In some embodiments, a trifloxystrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available trifloxystrobin fungicide product. When used for plant health applications, the trifloxystrobin formulations of the present disclosure can be used at active ingredient rates that correspond to any of the values or ranges of values noted above for the control of fungal diseases on soybean.

Trifloxystrobin—Pome Fruit

Labelled use rates for the control of various fungal diseases of Pome Fruit by Flint® and Flint® 500 WG two commercially available trifloxystrobin wettable granule products are provided in Table 14.

TABLE 14

| Product | Pome Fruits Labelled | Target Fungi | Use Rate (g ai/ha) |
|---|---|---|---|
| Flint ® | Apples, Pears, Crabapples, Loquat, Mayhaw, Quince | Scab (*Venturia* spp.) | Preventative: 70 Post-infection: 88 |
| | | Cedar Apple Rust (*Gymnosporangium juniperi-virginianae*), Powdery Mildew (*Podosphaera leucotricha*), Powdery Mildew (*Podosphaera leucotricha*) | 70-88 |
| | | Bitter Rot (*Glomerella cingulata*) | 105 |
| | | White Rot (*Botryosphaeria dothidea*) | 53 |
| Flint ® 500 WG | Apples | Scab (*Venturia inaequalis*) | 37.5-60 |

In some embodiments, the trifloxystrobin formulations of the current disclosure are used to control fungal diseases of pome fruits (including but not limited to apples, crabapples, pears, loquat, mayhaw, quince) at an active ingredient use rate that is lower than the use rate listed on the labels of commercially available trifloxystrobin fungicides. In some embodiments, a trifloxystrobin formulation of the current disclosure is used to control fungal diseases of pome fruits at a use rate that is less than about 75%, less than about 60%, less than about 50%, less than about 40%, less than about 30%, less than about 20%, or less than about 10% of a use rate listed on the label of a commercially available trifloxystrobin fungicide product.

In some embodiments, the trifloxystrobin formulations of the current disclosure are used to control fungal disease of pome fruits (including but not limited to apples, crabapples, pears, loquat, mayhaw, quince) at an active ingredient use rate that is lower than the minimum use rate of a range of use rates listed on the label of a commercially available trifloxystrobin product. In some embodiments a trifloxystrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available trifloxystrobin product.

In some embodiments, the trifloxystrobin formulations of the present disclosure are used to control fungal diseases of pome fruits at an active ingredient use rate of about 53-about 66 g/ha, about 42-about 53 g/ha, about 35-about 44 g/ha, about 28-about 35 g/ha, about 21-about 26 g/ha, about 14-about 18 g/ha or about 7-about 9 g/ha. In some embodiments, the trifloxystrobin formulations of the present disclosure are used to control fungal diseases of pome fruits at an active ingredient use rate of about 28-about 45 g/ha, about 22.5-about 36 g/ha, about 19-about 30 g/ha, about 15-about 24 g/ha, about 11-about 18 g/ha, about 7.5-about 12 g/ha or about 4-about 6 g/ha.

In some embodiments, the trifloxystrobin formulations of the present disclosure are used to control fungal diseases of pome fruits at an active ingredient use rate of less than about 53 g/ha, less than about 42 g/ha, less than about 35 g/ha, less than about 28 g/ha, less than about 21 g/ha, less than about 14 g/ha or less than about 7 g/ha. In some embodiments, the trifloxystrobin formulations of the present disclosure are used to control fungal diseases of pome fruits at an active ingredient use rate of less than about 28 g/ha, less than about 22.5 g/ha, less than about 19 g/ha, less than about 15 24 g/ha, less than about 11 g/ha, less than about 7.5 g/ha or less than about 4 g/ha.

In some embodiments, the trifloxystrobin formulations of the current disclosure can be used to control fungal diseases of pome fruits at an active ingredient use rate of less than about 39 g/ha, less than about 32 g/ha, less than about 26 g/ha, less than about 21 g/ha, less than about 16 g/ha, less than about 11 g/ha, or less than about 5 g/ha. In some embodiments, the trifloxystrobin formulations of the current disclosure can be used to control fungal diseases of pome fruits at an active ingredient use rate of less than about 52.5 g/ha, less than about 42 g/ha, less than about 35 g/ha, less than about 28 g/ha, less than about 21 g/ha, less than about 14 g/ha, or less than about 7 g/ha. In some embodiments, the trifloxystrobin formulations of the current disclosure can be used to control fungal diseases of pome fruits at an active ingredient use rate of less than about 66 g/ha, less than about 53 g/ha, less than about 44 g/ha, less than about 35 g/ha, less than about 26 g/ha, less than about 18 g/ha, or less than about 9 g/ha. In some embodiments, the trifloxystrobin formulations of the current disclosure can be used to control fungal diseases of pome fruits at an active ingredient use rate of less than about 78 g/ha, less than about 63 g/ha, less than about 53 g/ha, less than about 42 g/ha, less than about 32 g/ha, less than about 21 g/ha, or less than about 11 g/ha.

Non-limiting examples of fungal diseases of pome fruits that can be controlled with trifloxystrobin formulations of the present disclosure include those listed in Table 14, above.

In some embodiments, the trifloxystrobin formulations of the current disclosure are used for plant health applications on pome fruit at a use rate that is lower than a use rate listed on the label of a commercially available trifloxystrobin fungicide product. In some embodiments, the trifloxystrobin formulations of the current disclosure are used for plant health applications on pome fruit at a use rate that is lower than the minimum use rate of a range of use rates listed on the label of commercially available trifloxystrobin fungicide product. In some embodiments, a trifloxystrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available trifloxystrobin fungicide product. When used for plant health applications, the trifloxystrobin formulations of the present disclosure can be used at active ingredient rates that correspond to any of the values or ranges of values noted above for the control of fungal diseases on pome fruit.

Trifloxystrobin—Vine Fruits

In some embodiments, the trifloxystrobin formulations of the current disclosure are used to control fungal diseases of vine fruits (e.g., strawberries, grapes) at an active ingredient use rate that is lower than the use rate listed on the labels of commercially available trifloxystrobin fungicides. In some embodiments, a trifloxystrobin formulation of the current disclosure is used to control fungal diseases of vine fruits at a use rate that is less than about 75%, less than about 60%, less than about 50%, less than about 40%, less than about 30%, less than about 20%, or less than about 10% of a use rate listed on the label of a commercially available trifloxystrobin fungicide product.

In some embodiments, the trifloxystrobin formulations of the current disclosure are used to control fungal disease vine fruits (e.g., strawberries, grapes) at an active ingredient use rate that is lower than the minimum use rate of a range of use rates listed on the label of a commercially available trifloxystrobin product. In some embodiments a trifloxystrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available trifloxystrobin product.

Examples of fungal diseases of vine fruits corresponding active ingredient use rates for their control can be found on the labels of commercially available trifloxystrobin fungicide products.

In some embodiments, the trifloxystrobin formulations of the current disclosure are used for plant health applications on vine fruit at a use rate that is lower than a use rate listed on the label of a commercially available trifloxystrobin fungicide product. In some embodiments, the trifloxystrobin formulations of the current disclosure are used for plant health applications on vine fruit at a use rate that is lower than the minimum use rate of a range of use rates listed on the label of commercially available trifloxystrobin fungicide product. In some embodiments, a trifloxystrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available trifloxystrobin fungicide product. When used for plant health applications, the trifloxystrobin formulations of the present disclosure can be used at active ingredient rates that correspond to any of the values or ranges of values noted above for the control of fungal diseases on vine fruits.

Trifloxystrobin—Vine Fruits—Grapes

Labelled use rates for the control of various fungal diseases of Grapes by Flint® and Flint® 500 WG a commercially available trifloxystrobin wettable granule product, are provided in Table 15.

TABLE 15

| Product | Target Fungi | Use Rate (g ai/ha) |
|---|---|---|
| Flint ® | Powdery Mildew (*Uncinula necator*), *Botrytis* Bunch Rot (*Botrytis cinerea*), Phomopsis Cane and Leaf Spot (*Phomopsis viticola*), Black Rot (*Guignardia bidwellii*), Downy Mildew (*Plasmopara viticola*) | 53, 70, 105 or 140 depending on target disease, disease pressure, application interval etc. |

In some embodiments, the trifloxystrobin formulations of the current disclosure are used to control fungal diseases of grapes at an active ingredient use rate that is lower than the use rate listed on the labels of commercially available trifloxystrobin fungicides. In some embodiments, a trifloxystrobin formulation of the current disclosure is used to control fungal diseases of grapes at a use rate that is less than about 75%, less than about 60%, less than about 50%, less than about 40%, less than about 30%, less than about 20%, or less than about 10% of a use rate listed on the label of a commercially available trifloxystrobin fungicide product.

In some embodiments, the trifloxystrobin formulations of the current disclosure are used to control fungal disease grapes at an active ingredient use rate that is lower than the minimum use rate of a range of use rates listed on the label of a commercially available trifloxystrobin product. In some embodiments a trifloxystrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available trifloxystrobin product.

In some embodiments, the trifloxystrobin formulations of the current disclosure can be used to control fungal diseases of grapes an active ingredient use rate of about less than about 39 g/ha, less than about 32 g/ha, less than about 26 g/ha, less than about 21 g/ha, less than about 16 g/ha, less than about 11 g/ha, or less than about 5 g/ha. In some embodiments, the trifloxystrobin formulations of the current disclosure can be used to control fungal diseases of grapes an active ingredient use rate of less than about 53 g/ha, less than about 42 g/ha, less than about 35 g/ha, less than about 28 g/ha, less than about 21 g/ha, less than about 14 g/ha, or less than about 7 g/ha. In some embodiments, the trifloxystrobin formulations of the current disclosure can be used to control fungal diseases of grapes an active ingredient use rate of less than about 79 g/ha, less than about 63 g/ha, less than about 53 g/ha, less than about 42 g/ha, less than about 32 g/ha, less than about 21 g/ha, or less than about 11 g/ha. In some embodiments, the trifloxystrobin formulations of the current disclosure can be used to control fungal diseases of grapes an active ingredient use rate of less than about 105 g/ha, less than about 84 g/ha, less than about 70 g/ha, less than about 56 g/ha, less than about 42 g/ha, less than about 28 g/ha, or less than about 14 g/ha.

Non-limiting examples of fungal diseases of pome fruits that can be controlled with trifloxystrobin formulations of the present disclosure include those listed in Table 15, above.

In some embodiments, the trifloxystrobin formulations of the current disclosure are used for plant health applications on grapes at a use rate that is lower than a use rate listed on the label of a commercially available trifloxystrobin fungicide product. In some embodiments, the trifloxystrobin formulations of the current disclosure are used for plant health applications on grapes at a use rate that is lower than the minimum use rate of a range of use rates listed on the label of commercially available trifloxystrobin fungicide product. In some embodiments, a trifloxystrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available trifloxystrobin fungicide product. When used for plant health applications, the trifloxystrobin formulations of the present disclosure can be used at active ingredient rates that correspond to any of the values or ranges of values noted above for the control of fungal diseases on grapes.

Fluoxastrobin

In various embodiments, the fluoxastrobin formulations of the current disclosure may be used to control fungal diseases at active ingredient use rates that are lower than the use rates listed on the labels of commercially available fluoxastrobin fungicides. In some embodiments, a fluoxastrobin formulation of the current disclosure may be used to control fungal disease at a use rate that is less than about 75%, less than about 60%, less than about 50%, less than about 40%, less than about 30%, less than about 20% or less than about 10% of a use rate listed on the label of a commercially available fluoxastrobin fungicide product.

Labels of commercially available fluoxastrobin products often provide ranges of active ingredient use rates to control certain fungal diseases on certain plants (e.g., crops). In some embodiments, the fluoxastrobin formulations of the current disclosure are used to control fungal disease at an active ingredient use rate that is lower than the minimum use rate of a range of use rates listed on the label of a commercially available fluoxastrobin product. In some embodiments a fluoxastrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available product.

Fluoxastrobin—Cereals

In some embodiments, the fluoxastrobin formulations of the current disclosure are used to control fungal diseases of cereals at an active ingredient use rate that is lower than the use rate listed on the labels of commercially available fluoxastrobin fungicides. In some embodiments, a fluoxastrobin formulation of the current disclosure is used to control fungal diseases of cereals at a use rate that is less than about 75%, less than about 60%, less than about 50%, less than about 40%, less than about 30%, less than about 20%, or less than about 10% of a use rate listed on the label of a commercially available fluoxastrobin fungicide product.

In some embodiments, the fluoxastrobin formulations of the current disclosure are used to control fungal disease of cereals at an active ingredient use rate that is lower than the minimum use rate of a range of use rates listed on the label of a commercially available fluoxastrobin product. In some embodiments a fluoxastrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available fluoxastrobin product.

Examples of fungal diseases of cereals and corresponding active ingredient use rates for their control can be found on the labels of commercially available fluoxastrobin fungicide products. Examples of fungal diseases of cereals that can be controlled with formulations of the present disclosure include but are not limited to various fungal diseases of cereals noted in any other portion of the specification.

In some embodiments, the fluoxastrobin formulations of the current disclosure are used for plant health applications on cereals at a use rate that is lower than a use rate listed on the label of a commercially available fluoxastrobin fungicide product. In some embodiments, the fluoxastrobin formulations of the current disclosure are used for plant health applications on cereals at a use rate that is lower than the minimum use rate of a range of use rates listed on the label of commercially available fluoxastrobin fungicide product. In some embodiments, a fluoxastrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available fluoxastrobin fungicide product. When used for plant health applications, the fluoxastrobin formulations of the present disclosure can be used at active ingredient rates that correspond to any of the values or ranges of values noted above for the control of fungal diseases on cereals.

Picoxystrobin

In various embodiments, the picoxystrobin formulations of the current disclosure may be used to control fungal diseases at active ingredient use rates that are lower than the use rates listed on the labels of commercially available picoxystrobin fungicides. In some embodiments, a picoxystrobin formulation of the current disclosure may be used to control fungal disease at a use rate that is less than about 75%, less than about 60%, less than about 50%, less than about 40%, less than about 30%, less than about 20% or less than about 10% of a use rate listed on the label of a commercially available picoxystrobin fungicide product.

Labels of commercially available picoxystrobin products often provide ranges of active ingredient use rates to control certain fungal diseases on certain plants (e.g., crops). In some embodiments, the picoxystrobin formulations of the current disclosure are used to control fungal disease at an active ingredient use rate that is lower than the minimum use rate of a range of use rates listed on the label of a commercially available picoxystrobin product. In some embodiments a picoxystrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available product.

Picoxystrobin—Soybean

Labelled use rates for the control of various fungal diseases of soybean by Oranis® a commercially available picoxystrobin suspension concentrate, are provided in Table 16.

TABLE 16

| Product | Target Fungi | Use Rate (g ai/ha) |
| --- | --- | --- |
| Oranis ® | *Phakopsora pachyrhizi, Cercospora kikuchii, Septoria glycines* | 50-62.5 |

In some embodiments, the picoxystrobin formulations of the current disclosure are used to control fungal diseases of soybean at an active ingredient use rate that is lower than the use rate listed on the labels of commercially available picoxystrobin fungicides. In some embodiments, a picoxystrobin formulation of the current disclosure is used to control fungal diseases of soybean at a use rate that is less than about 75%, less than about 60%, less than about 50%, less than about 40%, less than about 30%, less than about 20%, or less than about 10% of a use rate listed on the label of a commercially available picoxystrobin fungicide product.

In some embodiments, the picoxystrobin formulations of the current disclosure are used to control fungal disease of soybean at an active ingredient use rate that is lower than the minimum use rate of a range of use rates listed on the label of a commercially available picoxystrobin product. In some embodiments a picoxystrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available picoxystrobin product.

In some embodiments, the picoxystrobin formulations of the present disclosure are used to control fungal diseases of soybean at an active ingredient use rate of about 37.5-about 50 g/ha, about 30-about 37.5 g/ha, about 25-about 31 g/ha, about 20-about 25 g/ha, about 15-about 19 g/ha, about 10-about 12.5 g/ha or about 5-about 6 g/ha.

In some embodiments, the picoxystrobin formulations of the present disclosure are used to control fungal diseases of soybean at an active ingredient use rate of less than about 37.5 g/ha, less than about 30 g/ha, less than about 25 g/ha, less than about 20 g/ha, less than about 15 g/ha, less than about 10 g/ha or less than about 5 g/ha.

Non-limiting examples of fungal diseases of soybeans that can be controlled with picoxystrobin formulations of the present disclosure include those listed in Table 16, above.

In some embodiments, the picoxystrobin formulations of the current disclosure are used for plant health applications on soybean at a use rate that is lower than a use rate listed on the label of a commercially available picoxystrobin fungicide product. In some embodiments, the picoxystrobin formulations of the current disclosure are used for plant health applications on soybean at a use rate that is lower than the minimum use rate of a range of use rates listed on the label of commercially available picoxystrobin fungicide product. In some embodiments, a picoxystrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available picoxystrobin fungicide product. When used for plant health applications, the picoxystrobin formulations of the present disclosure can be used at active ingredient rates that correspond to any of the values or ranges of values noted above for the control of fungal diseases on soybean.

Picoxystrobin—Cereals

Labelled use rates for the control of various fungal diseases of cereals by Acanto® a commercially available picoxystrobin suspension concentrate, are provided in Table 17.

TABLE 17

| Product | Cereal | Target Fungi | Use Rate (g ai/ha) |
|---|---|---|---|
| Acanto ® | Wheat | Powdery Mildew, *Septoria* leaf and glume blotch, , *Drechslera tritici-repentis*-leaf blotch, Leaf Rust, Yellow Rust | 250 |
| | Barley | Powdery Mildew, net blotch, Leaf Spot Disease, Dwarf Rust | 250 |
| | Rye | Powdery Mildew, Leaf Spot Disease, Brown Rust | 250 |
| | Triticale | *Septoria*-species | 250 |

In some embodiments, the picoxystrobin formulations of the current disclosure are used to control fungal diseases of cereals at an active ingredient use rate that is lower than the use rate listed on the labels of commercially available picoxystrobin fungicides. In some embodiments, a picoxystrobin formulation of the current disclosure is used to control fungal diseases of cereals at a use rate that is less than about 75%, less than about 60%, less than about 50%, less than about 40%, less than about 30%, less than about 20%, or less than about 10% of a use rate listed on the label of a commercially available picoxystrobin fungicide product.

In some embodiments, the picoxystrobin formulations of the current disclosure are used to control fungal disease of cereals at an active ingredient use rate that is lower than the minimum use rate of a range of use rates listed on the label of a commercially available picoxystrobin product. In some embodiments a picoxystrobin formulation of the current disclosure is used to control fungal disease at a use rate that is less than about 75%, less than about 60%, less than about 50%, less than about 40%, less than about 30%, less than about 20% or less than about 10% of the minimum use rate of a range of use rates listed on the label of a commercially available picoxystrobin product.

In some embodiments, the picoxystrobin formulations of the present disclosure are used to control fungal diseases of cereals at an active ingredient use rate of less than about 187.5 g/ha, less than about 150 g/ha, less than about 125 g/ha, less than about 100 g/ha, less than about 75 g/ha, less than about 50 g/ha or less than about 25 g/ha.

Non-limiting examples of fungal diseases of cereals that can be controlled with picoxystrobin formulations of the present disclosure include those listed in Table 17, above.

In some embodiments, the picoxystrobin formulations of the current disclosure are used for plant health applications on cereals at a use rate that is lower than a use rate listed on the label of a commercially available picoxystrobin fungicide product. In some embodiments, the picoxystrobin formulations of the current disclosure are used for plant health applications on cereals at a use rate that is lower than the minimum use rate of a range of use rates listed on the label of commercially available picoxystrobin fungicide product. In some embodiments, a picoxystrobin formulation of the current disclosure is used at a rate that is less than about 75%, about 60%, about 50%, about 40%, about 30%, about 20% or about 10% of the use rate (or the minimum use rate of a range of use rates) listed on the label of a commercially available picoxystrobin fungicide product. When used for plant health applications, the picoxystrobin formulations of the present disclosure can be used at active ingredient rates that correspond to any of the values or ranges of values noted above for the control of fungal diseases on cereals.

EXAMPLES

I: Preparation and Solid Formation of Nanoparticles of Polymer-Associated Active Ingredients Example 1: Preparation of 1 g of Polymer Nanoparticles from Poly (Methacrylic Acid-Co-Ethyl Acrylate) (p(MAA-co-EA))

1 g of polymer nanoparticles derived from p(MAA-co-EA) was made as follows. Briefly, 1 g solid p(MAA-co-EA) (MAA:EA=90:10 or 80:20, MW 450K-800K) was dissolved in 500 mL of deionized water in a 3 L beaker using an overhead stirrer, and pH was maintained at ~7 with 1M NaOH. The solution was stirred overnight to fully dissolve the solid. The next day, 500 mL of 3M NaCl was added to the solution under vigorous stirring. After addition, the solution was left to stir at 500 rpm for another hour. At this stage, the solution viscosity drops indicating the formation of collapsed polymers. The solution was then transferred to a 3 L recrystallization dish equipped with a magnetic stir bar. This solution was exposed to 4-254 nm UV germicidal lamps (G25T8) for 2 hours under constant stirring. After 2 hours, the solution was removed from the UV source and the ions were removed using diafiltration. The resulting retentate was then freeze dried to obtain a powder of the polymer nanoparticles. Alternatively, the retentate could also be spray dried to obtain a powder of the polymer nanoparticles. A particle size of 20-50 nm was measured via dynamic light scattering of a solution of either the collected freeze-dried or spray dried solid re-dispersed in 0.1M NaCl solution, pH adjusted to ~6.8 and stirred overnight.

The polarity of the microenvironment of the nanoparticles was investigated according to the method outlined in *Photochem. Photobiol.* 1982, 35:17. Briefly, 10 uL of a 0.1 mg/mL solution of pyrene in $CH_2Cl_2$ was placed in a 20 ml scintillation vial and the liquid was swirled around to coat the bottom of the vial. The solvent was allowed to evaporate under a fume hood. 10 ml of a 1 mg/mL dispersion of polymer nanoparticles in deionized water (pH adjusted to ~4.5) was added in to the vial with the dried out pyrene solution and was stirred for 48 hours in the dark. Emission spectra were then measured on a Perkin Elmer LS 55 Luminescence Spectrometer using an excitation wavelength of 340 nm, having slit widths for both excitation and emission at 2.5 nm. The emission intensity of the first ($I_1$, ~373 nm) and third ($I_3$, ~384 nm) vibronic bands were recorded and the ratio ($I_1/I_3$) calculated giving a ratio of ~1.18 indicating that the polymer nanoparticles prepared according to Example 1 has a microenvironment similar to the polarity/hydrophobicity of methanol (see table in *Photochem. Photobiol.* 1982, 35:17 for a complete tabulation of the ratios of $I_1/I_3$ and the corresponding microenvironment polarity.)

The same procedure was used to make polymer nanoparticles from different polyelectrolyte copolymers and polyelectrolyte homopolymers. Examples of other polyelectrolyte copolymers: poly(methacrylic acid (MAA)-co-styrene(S)) (MAA:S=75:25, MW 450K-800K), poly(acrylic acid (AA)-co-styrene(S)) (AA:S=75:25, MW 450K-800K).

Example 2: Formation of a Solid Formulation of Nanoparticles or Aggregates of Nanoparticles of Polymer-Associated Azoxystrobin Via Spray Drying Directly from Common Solvent Using p(MAA-co-EA) Nanoparticles 5 g of polymer nanoparticles derived from p(MAA-co-EA) were made according the procedure outlined in Example 1. The 5 g of polymer powder was dispersed in 250 mL technical grade methanol in a 500 mL glass beaker until a clear solution was formed, and was then filtered through coarse filter paper to remove any undispersed solids. 5 g of technical grade azoxystrobin was added to the filtered dispersion. The resulting solution was clear, and was stirred at 500 rpm using a magnetic stir bar on a stirrer hot plate for one hour. This solution was then spray dried on a Buchi mini Spray dryer B290 with inlet temperature set at 170° C., aspirator gas flow rate of approximately 35 m³/h, feed rate of approximately 7 mL/min and air of flow 601 L/hr. The solid was collected from the collector receptacle of the spray dryer. A volume average dynamic light scattering (DLS) particle size of ~300 nm was measured for the solid re-dispersed either in deionized water or CIPAC D hard water at 400 ppm (solids). DLS particle size was measured using a Malvern Zetasizer ZS.

Example 3: Formation of a Solid Formulation of Nanoparticles or Aggregates of Nanoparticles of Polymer-Associated Azoxystrobin from an Aqueous Dispersion Using p(MAA-co-EA) Polymer Nanoparticles 500 mg of polymer nanoparticles derived from p(MAA-co-EA) was made according to the procedure outlined in Example 1. The solid was dispersed in 25 mL technical grade methanol in a 50 mL glass beaker until a clear solution was formed, and was then filtered through coarse filter paper to remove any undispersed solids. 500 mg of technical grade azoxystrobin was then added to the filtered dispersion. The resulting solution was clear, and was stirred at 500 rpm using a magnetic stir bar on a stirrer hot plate for one hour. 0.250 L of deionized water was then placed in a 1 L glass beaker and was stirred at 500 rpm using an overhead mixer. The methanol solution containing the nanoparticles and azoxystrobin was then slowly dripped into the stirred water at a rate of ~1-2 mL/min using a peristaltic pump. After all the methanol has been added, the resulting milky solution was then left to mix for another 20 mins. The resulting solution was then freeze dried to obtain a solid formulation of azoxystrobin. The solid was redispersible in water at a concentration of ~200 ppm active ingredient. A volume average DLS particles size of ~300 nm was measured for the solid re-dispersed in deionized water at 400 ppm total solids in the measured dispersion. DLS particle size was measured using a Malvern Zeta sizer ZS.

Example 4: Formation of a Solid Formulation of Nanoparticles or Aggregates of Nanoparticles of Polymer-Associated Azoxystrobin from an Aqueous Dispersion Using p(MAA-co-EA) Polymer Nanoparticles at a 1:3 Active to Polymer Ratio 500 mg of polymer nanoparticles derived from p(MAA-co-EA) was made according to the procedure outlined in Example 1. The solid was dispersed in 25 mL technical grade methanol in a 50 mL glass beaker until a clear solution was formed, and was then filtered through coarse filter paper to remove any undispersed solids. 167 mg of technical grade azoxystrobin was then added to the filtered dispersion. The resulting solution was clear, and was stirred at 500 rpm using a magnetic stir bar on a stirrer hot plate for one hour. 0.250 L of deionized water was then placed in a 1 L glass beaker and was stirred at 500 rpm using an overhead mixer. The methanol solution containing the nanoparticles and azoxystrobin was then slowly dripped into the stirred water at a rate of ~1-2 mL/min using a peristaltic pump. After all the methanol has been added, the resulting milky solution was then left to mix for another 20 mins. The resulting solution was then freeze dried to obtain a solid formulation of azoxystrobin. The solid was redispersible in water at a concentration of ~200 ppm active ingredient. A volume average DLS particles size of ~300 nm was measured for the solid re-dispersed in deionized water at 400 ppm total solids in the measured dispersion. DLS particle size was measured using a Malvern Zeta sizer ZS.

Example 5: Formation of a Solid Formulation of Nanoparticles or Aggregates of Nanoparticles of Polymer-Associated Azoxystrobin from an Aqueous Dispersion Containing Phosphate Buffered Saline (PBS)

A 3% azoxystrobin solid formulation was made as follows: 300 mg of polymer nanoparticles derived from poly (acrylic acid (AA)-co-styrene(S)) (AA:S=75:25 by mass, MW 450K-800K) was made according to the procedure outlined in Example 1. The solid was dispersed in 15 mL technical grade methanol in a 50 mL glass beaker until a clear solution was formed, and was then filtered through coarse filter paper to remove any undispersed solids. 300 mg of technical grade azoxystrobin was then added to the filtered dispersion. The resulting solution was clear, and was stirred at 500 rpm using a magnetic stir bar on a stirrer hot plate for one hour. 1 L of PBS buffer (Invitrogen, 1×, pH 7.4) was then placed in a 2 L glass beaker and was stirred at 500 rpm using an overhead mixer. The methanol solution containing the nanoparticles and azoxystrobin was then slowly fed into the stirred buffer at a rate of ~1-2 mL/min using a peristaltic pump. The feeding tube was submerged under the buffer during the entire addition process. After all the methanol has been added, the resulting milky solution was then left to mix for another 20 mins. The solution was then concentrated by removing water/solvent using a rotary evaporator to about ½ its initial volume. The concentrated solution was then freeze dried to obtain a solid formulation of azoxystrobin. The solid was redispersible in water at a concentration of ~200 ppm active ingredient. A volume average DLS particles size of ~300 nm was measured for the solid re-dispersed in deionized water at 400 ppm total solids in the measured dispersion. DLS particle size was measured using a Malvern Zetasizer ZS. Similar solid formulations were made using polymer nanoparticles derived from poly (methacrylic acid (MAA)-co-styrene(S)) (MAA:S=75:25, MW 450K-800K) and p(MAA-co-EA) (MAA:EA=90:10 or 80:20, MW 450K-800K).

Example 6: Formation of a Solid Formulation of Nanoparticles or Aggregates of Nanoparticles of Polymer-Associated Azoxystrobin from a Dispersion Containing Phosphate Buffered Saline (PBS). [Nanoparticles Derived from p(AA-co-S); 1:1 Ratio of Azoxystrobin:Nanoparticles]

A 5.4% azoxystrobin solid formulation was made as follows: Polymer nanoparticles derived from poly(acrylic acid-co-styrene) (acrylic acid:styrene=75:25 by mass) were prepared according to the procedure outlined in Example 1. 0.6 g of the polymer nanoparticles and 0.6 g of technical grade azoxystrobin were added to 30 mL of technical grade methanol in a 50 mL beaker. The resultant clear methanol mixture was stirred for 30 minutes. The mixture was then added to 1170 g of 1×PBS buffer (Phosphate Buffered Saline, 1×, Gibco) through a feed tube that was submerged in the PBS solution at a rate of 5 mL/min using a peristaltic pump. The PBS solution was stirred at 500 rpm throughout the course of the addition. The resulting mixture was cloudy/translucent in appearance. The mixture was freeze dried to give a solid. When this solid was dispersed in RO water at a concentration of 200 ppm of azoxystrobin, the Z-average DLS particle size was 416 nm. DLS particle size was measured using a Malvern Zetasizer ZS.

Example 7: Formation of a Solid Formulation of Nanoparticles or Aggregates of Nanoparticles of Polymer-Associated Azoxystrobin from an Aqueous Dispersion Containing Phosphate Buffered Saline (PBS) at 3:2 Polymer Nanoparticle:Azoxystrobin Ratio A 3% azoxystrobin solid formulation was made as follows: 450 mg of polymer nanoparticles derived from poly (acrylic acid (AA)-co-styrene(S)) (AA:S=75:25, MW 450K-800K) was made according to the procedure outlined in Example 1. The solid was dispersed in 15 mL technical grade methanol in a 50 mL glass beaker until a clear solution was formed, and was then filtered through coarse filter paper to remove any undispersed solids. 300 mg of technical grade azoxystrobin was then added to the filtered dispersion. The resulting solution was clear, and was stirred at 500 rpm using a magnetic stir bar on a stirrer hot plate for one hour. 1 L of PBS buffer (Invitrogen, 1×, pH 7.4) was then placed in a 2 L glass beaker and was stirred at 500 rpm using an overhead mixer. The methanol solution containing the nanoparticles and azoxystrobin was then slowly fed into the stirred buffer at a rate of ~1-2 mL/min using a peristaltic pump. The feeding tube was submerged under the buffer during the entire addition process. After all the methanol has been added, the resulting milky solution was then left to mix for another 20 mins. The resulting solution was then freeze dried to obtain a solid formulation of azoxystrobin. The solid was redispersible in water at a concentration of ~200 ppm active ingredient. A volume average DLS particles size of ~300 nm was measured for the solid re-dispersed in deionized water at 400 ppm total solids in the measured dispersion. DLS particle size was measured using a Malvern Zeta sizer ZS.

Example 8: Formation of a Solid Formulation of Nanoparticles or Aggregates of Nanoparticles of Polymer-Associated Azoxystrobin from an Aqueous Dispersion Containing 0.05M NaCl Solution and a Dispersing Agent A 40% azoxystrobin solid formulation was made as follows: 300 mg of polymer nanoparticles derived from poly(methacrylic acid (MAA)-co-styrene(S)) (MAA:S=75:25, MW 450K-800K) was made according to the procedure outlined in Example 1. The solid was dispersed in 15 mL technical grade methanol in a 50 mL glass beaker until a clear solution was formed, and was then filtered through coarse filter paper to remove any undispersed solids. 300 mg of technical grade azoxystrobin was then added to the filtered dispersion. The resulting solution was clear, and was stirred at 500 rpm using a magnetic stir bar on a stirrer hot plate for one hour. 1 L of deionized water was then placed in a 2 L glass beaker and was stirred at 500 rpm using an overhead mixer. To this, 40 mg of Soprophor BSU and 120 mg of NaCl was added. The methanol solution containing the nanoparticles and azoxystrobin was then slowly fed into the stirred buffer at a rate of ~1-2 mL/min using a peristaltic pump. The feeding tube was submerged under the buffer during the entire addition process. After all the methanol has been added, the resulting milky solution was then left to mix for another 20 mins. The resulting solution was then freeze dried to obtain a solid formulation of azoxystrobin. The solid was redispersible in water at a concentration of ~200 ppm active ingredient. A volume average DLS particles size of ~300 nm was measured for the solid re-dispersed in deionized water at 400 ppm total solids in the measured dispersion. DLS particle size was measured using a Malvern Zetasizer ZS. Similar solid formulations were made using polymer nanoparticles derived from poly(acrylic acid (AA)-co-styrene(S)) (AA:S=75:25, MW 450K-800K) and p(MAA-co-EA) (MAA:EA=90:10 or 80:20, MW 450K-800K).

Example 9: Differential Scanning Calorimetry (DSC) Analysis of a Solid Formulation of Nanoparticles or Aggregates of Nanoparticles of Polymer-Associated Azoxystrobin Thermal analysis (DSC) was done using a Perkin Elmer Diamond Differential Scanning Calorimeter under $N_2$ atmosphere. The thermal behavior of 6.05 mg of azoxystrobin was analyzed in an Aluminum sample pan from $H2^O$ to 160° C. at a temperature ramp rate of 5° C./min. Similarly, the thermal behavior of 5.3 mg of a solid formulation prepared according to Example 4 was analyzed in an Aluminum pan from 25° C. to 160° C. at a temperature ramp rate of 5° C./min. Heat flow (mW/° C.) for both samples is shown in FIG. 1. No melting point is observed for the solid formulation of azoxystrobin prepared according to Example 4 compared to pure unformulated azoxystrobin which has an endothermic (melting) peak at 121° C.

II: Formulations

Example 10: Formation of a WP Formulation from an Aqueous Dispersion of Nanoparticles or Aggregates of Nanoparticles of Polymer-Associated Azoxystrobin A 24% azoxystrobin solid formulation was made as follows: 500 mg of polymer nanoparticles derived from p(MAA-co-EA) was made according to the procedure outlined in Example 1. The solid was dispersed in 25 mL technical grade methanol in a 50 mL glass beaker until a clear solution was formed, and was then filtered through coarse filter paper to remove any undispersed solids. 500 mg of technical grade azoxystrobin was then added to the filtered dispersion. The resulting solution was clear, and was stirred at 500 rpm using a magnetic stir bar on a stirrer hot plate for one hour. 250 mL of deionized water was then placed in a 500 mL glass beaker and was stirred at 500 rpm using an overhead mixer. To this, 1.0 g of lactose, 30 mg of Reax88B, and 30 mg of Soprophor 4D 384 were added. The methanol solution containing the polymer nanoparticles and azoxystrobin was then slowly dripped into the water at a rate of ~1-5 mL/min using a peristaltic pump. After all the methanol solution had been added, the resulting milky solution was then left to mix for another 20 mins. The solution was then concentrated by removing solvent (both water and methanol) using a rotary evaporator until ~30-40% of the original volume was left. The concentrated mixture was freeze dried to obtain a dry powder. No visible phase separation was observed in the solid after several freeze thaw cycles (−5° C. to 45° C.). The cycled WP was redispersible in CIPAC-D hard water and had a dispersed particle size of 300 nm at 200 ppm active concentration with native solution pH at 5.6. The same powder was made using nanoparticles derived from a homopolymer of acrylic acid (MW 345K).

Example 11: Formation of a WP Formulation from an Aqueous Dispersion of Nanoparticles or Aggregates of Nanoparticles of Polymer-Associated Azoxystrobin. [Nanoparticles Derived from p(MAA-co-S); 1:1 Ratio of Azoxystrobin:Nanoparticles]

A 24% azoxystrobin solid formulation was made as follows: Polymer nanoparticles derived from p(MAA-co-S) (MAA:S=75:25 by mass) were prepared according to the procedure outlined in Example 1. 1.5 g of the polymer nanoparticles and 1.5 g of technical grade azoxystrobin were added to 75 mL of technical grade methanol in a 150 mL beaker. The resulting clear yellow mixture was stirred for 30 mins. 750 g RO water, 3000 mg lactose, 90 mg Reax 88B and 90 mg Soprophor 4D384 were added to a 1 L beaker and the resulting aqueous solution was stirred at 500 rpm for 30 minutes. The methanol mixture was then added to the aqueous solution by means of a peristaltic pump at a rate of 5 mL/min though a feed tube submerged in the stirred aqueous solution. The aqueous mixture was stirred at 500 rpm throughout the entire addition process. After addition, the resulting mixture was cloudy/translucent and yellow in appearance. The resulting mixture was then freeze dried to give a solid. 2.01 g of the freeze dried solid was mixed with 81 mg D-sorbitol using a spatula to form a homogenous powder. The solid mixture was placed in 2 dram glass vial and was vortexed for 10 mins. When this solid was dispersed in RO water at a concentration of 200 ppm azoxystrobin, the Z-average DLS particle was 186 nm. DLS particle size was measured using a Malvern Zetasizer.

Example 12: Formation of a WP Formulation of Nanoparticles or Aggregates of Nanoparticles of Polymer Associated Azoxystrobin. [Nanoparticles Derived from p(MAA-co-S); 1:1 Ratio of Azoxystrobin:Nanoparticles] in a High Salt Solution A 28% azoxystrobin solid formulation was made as follows: Polymer nanoparticles derived from p(MAA-co-S) (MAA:S=75:25 by mass) were prepared according to the procedure outlined in Example 1. 1.5 g of the polymer nanoparticles and 1.5 g of technical grade azoxystrobin were added to 75 mL of technical grade methanol in a 150 mL beaker. The resulting clear yellow mixture was stirred for 30 mins. 750 g RO water, 90 mg Reax 88B and 12.5 mL NaCl (3M solution) were added to a 1 L beaker and the resulting aqueous solution was stirred at 500 RPM for 30 mins. The methanol mixture was then added to the aqueous mixture by means of a peristaltic pump at a rate of 5 mL/min though a feed tube submerged in the stirred aqueous mixture. The aqueous mixture was stirred at 500 rpm throughout the entire addition process. The resulting mixture was cloudy/translucent and yellow in appearance. The resulting mixture was then freeze dried to give a solid. When this solid was dispersed in RO water at a concentration of 200 ppm azoxystrobin, the Z-average DLS particle was 274 nm. DLS particle size was measured using a Malvern Zetasizer ZS.

Example 13: Formation of WG Formulation from a Liquid Dispersion of Nanoparticles or Aggregates of Nanoparticles of Polymer-Associated Azoxystrobin 10 g of a solid formulation was prepared according to Example 3 using p(MAA-co-EA). 10 g of the freeze-dried powder was then placed in a beaker. To this solid, about 2.5-3.0 of water was slowly added under constant mixing until the resulting mixture had a dough-like consistency. The dough-like mixture was then extruded into 15 cm strips though the orifice of a 5 mL disposable hypodermic syringe. The extruded strips were allowed to dry for 1 hour and were then cut into 2-5 mm granules. The WG formulation had minimal dustiness, and visible phase separation was observed in the solid after several freeze thaw cycles (−5° C. to 45° C.). The cycled WP was redispersible in CIPAC-D hard water and had a dispersed particle size of 300 nm at 200 ppm active concentration. No phase separation of the active ingredient occurred after several temperature cycles between 25° C. and 54° C.

Example 14: Preparation of a HSLS Formulation from a Solid Formulation of Nanoparticles or Aggregates of Nanoparticles of Polymer-Associated Azoxystrobin Via Ball-Milling [Nanoparticles Derived from p(MAA-co-EA); 3:1 Ratio of Azoxystrobin:Nanoparticles]

A 15% HSLS of azoxystrobin was prepared as follows. 1 g of polymer nanoparticles derived from poly(MAA-co-EA) [MAA:EA=75:25 by mass; prepared according to Example 1] and 3 g of technical grade azoxystrobin were added to 200 ml of methanol, and the resulting dispersion was spray dried according to the procedure outlined in Example 2. 1.5 g of the resulting spray dried powder was placed in a 16 mL brown glass vial (vial 1) along with 0.075 g Geropon T77, 0.375 g of Geropon TA/72 and 10 g of stainless steel beads (20-30 mesh). The vial was covered, secured to a vortex, and shaken at 80% power for approximately 30 mins. 0.5025 g propylene glycol, 0.3 g FG-10 (DOW® Corning, 10% active anti-foam ingredient silicone emulsion), 0.02 g Proxel BD-20 (biocide, Industrial Microbiostat, 19.3% active biocide ingredient, Arch Chemicals Inc.), and 4.69 g RO water were added into a separate 16 mL vial (vial 2). The vial was covered, secured to a vortex, and shaken at 80% power for approximately 30 mins. The contents of vial 2 were poured into vial 1. The resulting mixture was secured to a vortex and shaken at 80% power for 5 days. When the resulting formulation was diluted in RO water at a concentration of 200 ppm azoxystrobin, the Z-average DLS particle size was 306 nm. DLS particle size was measured using a Malvern Zeta sizer ZS.

Example 15: Preparation of a HSLS Formulation from a Solid Formulation of Nanoparticles or Aggregates of Nanoparticles of Polymer-Associated Azoxystrobin Via Ball-Milling [Nanoparticles Derived from p(MAA-co-S); 3:1 Ratio of Azoxystrobin:Nanoparticles]

A 15.7% HSLS of azoxystrobin was prepared as follows. 1 g of polymer nanoparticles derived from derived from poly(MAA-co-S) [MAA:S=75:25 by weight] and 3 g of technical grade azoxystrobin were added to 200 mL of methanol, and the resulting dispersion was spray-dried according to the procedure outlined in Example 2. 1.5 g of the resulting spray dried powder was placed in a 16 mL brown glass vial (vial 1) along with 0.075 g Geropon T77, 0.375 g of Geropon TA/72 and 10 g of stainless steel beads (20-30 mesh). The vial was covered, secured to a vortex, and shaken at 80% power for approximately 30 mins. 0.5025 g propylene glycol, 0.3 g FG-10 (DOW® Corning, 10% active anti-foam ingredient silicone emulsion), 0.02 g Proxel BD-20 (biocide, Industrial Microbiostat, 19.3% active biocide ingredient, Arch Chemicals Inc.), and 4.69 g RO water were added into a separate 16 mL vial (vial 2). The vial was covered, secured to a vortex, and shaken at 80% power for approximately 30 mins. The contents of vial 2 were poured into vial 1. The resulting mixture was secured on a vortex and shaken at 80% power for 5 days. When the resulting formulation was diluted in RO water at a concentration of 200 ppm azoxystrobin, the Z-average DLS particle size is 351 nm. DLS particle size was measured using a Malvern Zetasizer ZS.

Example 16: Preparation of a HSLS Formulation from a Solid Formulation of Nanoparticles or Aggregates of Nanoparticles of Polymer-Associated Azoxystrobin Via Ball-Milling [Nanoparticles Derived from p(MAA-co-BUMA); 2:1 Ratio of Azoxystrobin:Nanoparticles]

A 16% HSLS of azoxystrobin was prepared as follows. 1 g of polymer nanoparticles derived from derived from poly(MAA-co-BUMA) [MAA:BUMA=75:25 by weight; BUMA=Butyl methacrylate] and 2 g of technical grade azoxystrobin were added to 200 mL of methanol, and the resulting dispersion was spray-dried according to the procedure outlined in Example 2. 2 g of the resulting spray dried powder was placed in a 36 mL brown glass vial (vial 1) along with 0.089 g Geropon T77, 0.445 g of Geropon TA/72 and 10 g of stainless steel beads (20-30 mesh). The vial was covered, secured to a vortex, and shaken at 80% power for approximately 30 mins. 0.608 g propylene glycol, 0.362 g FG-10 (DOW® Corning, 10% active anti-foam ingredient silicone emulsion), 0.023 g Proxel BD-20 (biocide, Industrial Microbiostat, 19.3% active biocide ingredient, Arch Chemicals Inc.), 0.356 g Xanthan gum solution (5% aqueous Xanthan gum prepared form Kelzan® M, CP Kelco U.S., Inc.), and 3.77 g RO (Reverse-osmosis purified) were added to a separate 36 mL vial (vial 2). The vial was covered, secured to a vortex, and shaken at 80% power for approximately 30 mins. The contents of vial 2 were poured into vial 1. The resulting mixture was secured on a vortex and shaken at 80% power for 2 days. When the resulting formulation was diluted in RO water at a concentration of 200 ppm azoxystrobin, the Z-average DLS particle size is 243 nm. DLS particle size was measured using a Malvern Zetasizer ZS.

Example 17: Preparation of a HSLS Formulation from a Solid Formulation of Nanoparticles or Aggregates of Nanoparticles of Polymer-Associated Azoxystrobin Via Ball-Milling [Nanoparticles Derived from p(MAA-co-EA); 2:1 Ratio of Azoxystrobin:Nanoparticles]

A 15% HSLS of azoxystrobin was prepared as follows. 1 g of polymer nanoparticles derived from derived from poly(MAA-co-EA) [MAA:EA=90:10 by weight] and 2 g of technical grade azoxystrobin were added to 200 mL of methanol, and the resulting dispersion was spray-dried according to the procedure outlined in Example 2. 2 g of the resulting spray dried powder was placed in a 36 mL brown glass vial (vial 1) along with 0.089 g Geropon T77, 0.445 g of Geropon TA/72, 1.482 g PVA (polyvinyl alcohol 13-23K MW, Gohsenol) and 10 g of stainless steel beads (20-30 mesh). The vial was covered, secured to a vortex, and shaken at 80% power for approximately 30 mins. 0.596 g propylene glycol, 0.356 g FG-10 (DOW® Corning, 10% active anti-foam ingredient silicone emulsion), 0.023 g Proxel BD-20 (biocide, Industrial Microbiostat, 19.3% active biocide ingredient, Arch Chemicals Inc.), and 3.0 g RO (Reverse-osmosis purified) water were added into a separate 36 mL vial (vial 2). The vial was covered, secured to a vortex, and shaken at 80% power for approximately 30 mins. The contents of vial 2 were poured into vial 1. The resulting mixture was secured on a vortex and shaken at 80% power for 3 days. When the resulting formulation was diluted in RO water at a concentration of 200 ppm azoxystrobin, the Z-average DLS particle size is 257 nm. DLS particle size was measured using a Malvern Zetasizer ZS.

Example 18: Preparation of a HSLS Formulation from a Solid Formulation of Nanoparticles or Aggregates of Nanoparticles of Polymer-Associated Azoxystrobin Via Ball-Milling [Nanoparticles Derived from p(MAA-co-EA); 4:1 Ratio of Azoxystrobin:Nanoparticles]

A 17% HSLS of azoxystrobin was prepared as follows. 1 g of polymer nanoparticles derived from poly(MAA-co-EA) [MAA:EA=90:10 by weight, prepared according to Example 1] and 4 g of technical grade azoxystrobin were added to 200 mL of methanol, and the resulting dispersion was spray-dried according to the procedure outlined in example 2. 2 g of the resulting spray dried powder was placed in a 36 mL brown glass vial (vial 1) along with 0.107 g Geropon T77, 0.533 g of Geropon TA/72, 2.133 g Silwet L-77 solution (10% aqueous solution) and 10 g of stainless steel beads (20-30 mesh). The vial was covered, secured to a vortex, and shaken at 80% power for approximately 30 mins. 0.715 g propylene glycol, 0.427 g FG-10 (DOW® Corning, 10% active anti-foam ingredient silicone emulsion), 0.031 g of Proxel BD-20 (biocide, Industrial Microbiostat, 19.3% active biocide ingredient, Arch Chemicals Inc.), 0.436 g Xanthan gum solution (5% aqueous Xanthan gum prepared form Kelzan® M, CP Kelco U.S., Inc.), and 4.5 g RO (Reverse-osmosis purified) water were added into a separate 36 mL vial (vial 2). The vial was covered, secured to a vortex, and shaken at 80% power for approximately 30 mins. The contents of vial 2 were poured into vial 1. The resulting mixture was secured on a vortex and shaken at 80% power for 4 days. When the resulting formulation was diluted in RO water at a concentration of 200 ppm azoxystrobin, the Z-average DLS particle size was 225 nm. DLS particle size was measured using a Malvern Zetasizer ZS.

III Formulation Testing

Example 19: Lab-Scale Trial to Evaluate Translocation Properties of Azoxystrobin Formulations of the Present Disclosure and Commercially Available Azoxystrobin Formulations in Corn The translocation of azoxystrobin in formulations prepared according to the present disclosure was compared to the commercially available azoxystrobin formulation Amistar®. Dispersions of Amistar® and various formulations of the present disclosure were prepared in 0.25 wt % Enhance solution (prepared in RO water) at azoxystrobin concentrations of 200 or 500 ppm.

The following outlines the procedure for a single translocation experiment:

Corn plants (corn variety: Sunnyvee) were planted and placed in a growth chamber. 12-16 days after planting, the basal region of the newest fully emerged leaf of a corn plant was treated with an azoxystrobin dispersion. Prior to treatment, the boundaries of the basal treatment area of the leaf were defined with a red paint pen. Ten 0.5 µL drops of the azoxystrobin formulation were then pipetted onto the upper surface of the basal treatment area (not on central vein). The drops were then allowed to dry (drying is complete within 1 hour), and the plant was placed back into a growth chamber. The treated leaf was harvested 24 hours later by cutting it at its base. The tip of the leaf was cut from the apical section (ca. 1.5 cm above the treatment boundary line), allowed to dry and placed in a glass vial. The dried leaf tips were weighed, and the amount of azoxystrobin in the leaf tip was determined by extracting the tip with 4 mL of acetone and quantifying the amount of extracted active via HPLC.

Three replicate treatments were performed for each of the dispersions investigated (reported values correspond to averages). Control leaf treatments of deionized water and deionized water+Enhance (0.25%) were also performed Table 18 and Table 19 demonstrate the translocation properties of dispersions of various formulations at 200 and 500 ppm azoxystrobin, respectively.

TABLE 18

Results of translocation trials of several azoxystrobin formulations dispersed in 0.25 wt % Enhance solution at 200 ppm azoxystrobin.

| Formulation | Treatment Concentration (ppm) | wt % ($\times 10^{-3}$) azoxystrobin in leaf biomass (SD) | azoxystrobin in leaf biomass (µg) (SD) |
|---|---|---|---|
| Amistar® | 200 (have left these numbers because might merge tables later) | 2 (1) | 0.12 (0.07) |
| Example 6 | 200 | 7 (1) | 0.38 (0.04) |
| Example 11 | 200 | 3 (1) | 0.27 (0.07) |
| Example 12 | 200 | 5 (1) | 0.4 (0.1) |
| Example 14 | 200 | 3 (1) | 0.21 (0.03) |

SD = standard deviation (values in parentheses).

TABLE 19

Results of translocation trials of several formulations dispersed 0.25 wt % Enhance solution at 500 ppm azoxystrobin.

| Formulation | Treatment Concentration (ppm) | wt % ($\times 10^{-3}$) azoxystrobin in leaf biomass (SD) | azoxystrobin in leaf biomass (µg) |
|---|---|---|---|
| Amistar® (control for Example 15, below) | 500 (have left these numbers because might merge tables later) | 2 (1) | 0.13 (0.05) |
| Example 15 | 500 | 3 (2) | 0.2 (0.1) |
| Amistar® (control for Example 16-Example 18, below) | 500 | 1.1 (0.2) | 0.09 (0.06) |
| Example 16 | 500 | 4.8 (0.07) | 0.21 (0.02) |
| Example 17 | 500 | 3 (1) | 0.2 (0.1) |
| Example 18 | 500 | 2.4 (0.8) | 0.12 (0.03) |

SD = standard deviation (values in parentheses).

Example 20: High-Salt Stability/Compatibility and of Formulations Prepared According to the Present Disclosure The redispersibility of azoxystrobin formulation of the present disclosure was tested by dispersing formulations prepared according to Example 15 and Example 17 in CIPAC H hard water (634 ppm hardness) at an active ingredient concentration of 200 ppm. The formulations dispersed well and were stable, with no signs of the formation of flocs. When dispersed in CIPAC H hard water under these conditions, the Z-average DLS particle size of the formulation of Example 15 was 237 nm, and that of Example 17 was 450 nm. As described in other Examples, other formulations of the present disclosure are redispersible solutions of varying hardness (e.g., other CIPAC standard waters).

Example 21: Stability Tests of Formulations of the Present Disclosure

The stability of formulations of the current disclosure prepared according to Example 15 and Example 17 was evaluated under two sets of conditions. Briefly, formulations were kept in an environment chamber (Thermotron S-1.2C) for two weeks with alternating temperatures of ~5° C. and 45° C. Each temperature was programmed for a 24-hour cycling process. After the two-week temperature cycling process was complete, the formulations were redispersed in CIPAC H hard water (634 ppm hardness) at an active ingredient concentration of 200 ppm, and the Z-average particle size was measured by DLS. The formulations suspended well, with slightly increased particle size compared to measured particle sizes prior to cycling. The formulations were also maintained at a constant temperature of 54° C. in an oven for one week, and then dispersed in CIPAC H water as described above. The formulations suspended well, with slightly increased Z-average particle sizes compared to sizes prior to incubation at 54° C. As described in other Examples, other formulations of the current disclosure are stable under a variety of test conditions (e.g., temperature cycling).

Example 22: Leaf Dip Bioassay to Test for Rainfastness of Azoxystrobin Formulations Prepared According to the Current Disclosure The rainfastness of formulations of azoxystrobin prepared according to the current disclosure and commercially available Amistar® was evaluated via a leaf dip assay.

1.7 cm leaf disks were cut from leaves of organically grown cabbage (ca. 7 leaf stage) and were inoculated with dispersions prepared from formulations of the present disclosure or Amistar. The inoculating dispersions were prepared at 50 ppm azoxystrobin in an aqueous solution containing 0.5% Supercharge Spray Adjuvant. Leaves were then dipped into the inoculating dispersions for 5 seconds and then placed on a rack and allowed to air dry completely (1-2 hours) (No Rain). To test for rainfastness, some of the inoculated leaves were then dipped in deionized water for 5 seconds, and were allowed to air dry for 2 more hours (Rain treatment). The dried leaf tips were weighed, and the amount of azoxystrobin on the surface was determined by extracting the leaves with 3 mL of acetone and quantifying the amount of extracted active via HPLC.

Three replicate treatments were performed for each of the investigated (reported values correspond to averages). The results are presented in Table 20, with the amount of azoxystrobin reported as percentage dry biomass of the dried leaf. Control leaf treatments of deionized water and deionized water+Supercharge (0.5%) were also performed.

The formulations of the current disclosure have are sufficiently rainfast to retain azoxystrobin on the leaf after subjection to "Rain" conditions.

TABLE 20

Evaluation of rainfastness of azoxystrobin formulations

| Formulation | Treatment Type | wt % ($\times 10^{-3}$) azoxystrobin in leaf biomass (SD) |
|---|---|---|
| Amistar ® | No Rain | 14 (4) |
|  | Rain | 11 (3) |
| Example 15 | No Rain | 11 (3) |
|  | Rain | 17 (1) |
| Example 16 | No Rain | 11 (1) |
|  | Rain | 21 (4) |
| Example 17 | No Rain | 15 (7) |
|  | Rain | 13 (1) |

Example 23: Stability and Dispersibility of HSLS Formulations in CIPAC G, H and J Standard Waters HSLS formulations prepared according to Example 14, Example 15, Example 16, Example 17 and Example 18 were dispersed in CIPAC G standard water (8000 ppm hardness, pH 6.0-7.0, $Mg^{2+}$) at a concentration of 200 ppm azoxystrobin. The resulting dispersion were stable (no visible aggregation/flocculation) for at least 1 hour. Dispersions prepared using CIPAC H standard water (634 ppm hardness, pH6.0-7.0, $Ca^{2+}:Mg^{2+}=2.5:1$) and CIPAC J standard water (634 ppm hardness, pH6.0-7.0, $Ca^{2+}:Mg^{2+}=2.5:1$) also resulted in dispersions that were stable (no visible aggregation/flocculation) for at least an hour.

The invention claimed is:

1. A liquid formulation comprising:
   nanoparticles comprising a polymer and a strobilurin compound with an average diameter of between about 1 nm and about 500 nm; wherein the polymer is a polyelectrolyte copolymer comprised of between about 50 weight percent and about 95 weight percent methacrylic acid monomers and between about 50 weight percent and about 5 weight percent ethyl acrylate or styrene monomers and the strobilurin compound is associated with the polymer;
   between about 0.5 weight percent and about 5 weight percent of a naphthalene sulfonate condensate dispersant;
   between about 0.5 weight percent and about 5 weight percent of a sodium dodecylbenzene sulfonate wetting agent;
   between about 0.1 weight percent and about 1 weight percent of an anti-foaming agent;
   between about 0.01 weight percent and about 0.1 weight percent a preservative; and
   water;
      wherein the nanoparticles comprise between about 1 weight percent and about 50 weight percent of the formulation.

2. The liquid formulation of claim 1, wherein the strobilurin compound comprises between about 5 weight percent and about 30 weight percent of the formulation.

3. The liquid formulation of claim 1, wherein a ratio of a weight percent of the strobilurin compound to a weight percent of the polymer is between about 1:1 to 6:1.

4. The liquid formulation of claim 1, wherein the nanoparticles have a melting point of less than 80° C.

5. The liquid formulation of claim 1, wherein the strobilurin compound is selected from the group consisting of azoxystrobin, picoxystrobin, pyraclostrobin, orysastrobin, metominostrobin, fluoxastrobin and trifloxystrobin.

6. The liquid formulation of claim 1, further comprising a thickener.

7. The liquid formulation of claim 6, wherein the thickener comprises between about 0.05 weight percent and about 5 weight percent of the formulation.

8. The liquid formulation of claim 1, further comprising an anti-freeze agent.

9. The liquid formulation of claim 8, wherein the anti-freeze agent comprises between about 1 weight percent and about 10 weight percent of the formulation.

10. The liquid formulation of claim 1, further comprising an additional pesticidal compound.

11. The liquid formulation of claim 10, wherein the additional pesticidal compound is a fungicide.

12. The liquid formulation of claim 10, wherein the additional pesticide comprises between about 5 weight percent and about 30 weight percent of the formulation.

13. The liquid formulation of claim 1, where the polymer is a poly(methacrylic acid-co-ethyl acrylate) polymer.

14. The liquid formulation of claim 1, further comprising a liquid fertilizer.

15. The liquid formulation of claim 14, wherein the fertilizer comprises at least one of the elements selected from the group consisting of boron, copper, manganese, iron, chorine, molybdenum, zinc sulfur, nitrogen, phosphorus and potassium.

16. The liquid formulation of claim 1, wherein the polymer is cross-linked.

17. A method of controlling fungi comprising applying the liquid formulation of claim 1 to a plant, a location near a plant, or to soil where a seed is or will be planted.

18. The method of claim 17, wherein the liquid formulation is applied to a corn plant at a concentration of between about 11 and about 109 grams of the strobilurin compound per hectare, and the fungi are selected from the group consisting of Rust (*Puccinia sorghi*), anthracnose leaf blight (*Colletotrichum graminicola*), Gray leaf spot (*Cercospora sorghi*), Northern corn leaf blight (*Setosphaeria turcica*), Northern corn leaf spot (*Cochliobolus carbonum*), Southern corn leaf blight (*Cochliobolus heterostrophus*) and Eye spot (*Aureobasidium zeae*).

19. The method of claim 17, wherein the liquid formulation is applied to a soybean plant at a concentration of between about 11 and about 109 grams of the strobilurin compound per hectare, and the fungi are selected from the group consisting of Aerial blight (*Rhizoctonia solani*), Anthracnose (*Colletotrichum truncatum*), Alternaria leaf spot (*Alternaria* spp.), Brown spot (*Septoria glycines*) Cercospora blight and leaf spot (*Cercospora kikuchii*), Frogeye leaf spot (*Cercospora sojina*), Pod and stem blight (*Diaporthe phaseolorum*), and the strobilurin compound is azoxystrobin.

* * * * *

UNITED STATES PATENT AND TRADEMARK OFFICE
CERTIFICATE OF CORRECTION

PATENT NO. : 10,206,391 B2  
APPLICATION NO. : 14/367473  
DATED : February 19, 2019  
INVENTOR(S) : Fugang Li et al.

Page 1 of 1

It is certified that error appears in the above-identified patent and that said Letters Patent is hereby corrected as shown below:

On the Title Page

In the inventor list:
Please insert --; Darren J. Anderson, Toronto (CA)-- after "Henry Galas, Toronto (CA)"

Signed and Sealed this
Sixteenth Day of July, 2019

Andrei Iancu
*Director of the United States Patent and Trademark Office*